United States Patent [19]

Iizuka et al.

[11] Patent Number: 5,469,850
[45] Date of Patent: Nov. 28, 1995

[54] ULTRASONIC DIAGNOSTIC SYSTEM

[75] Inventors: Miyuki Iizuka; Akira Shiba, both of Kawasaki, Japan

[73] Assignee: Fujitsu Limited, Kawasaki, Japan

[21] Appl. No.: 405,237

[22] Filed: Mar. 16, 1995

[30] Foreign Application Priority Data

May 27, 1994 [JP] Japan ..................................... 6-115030
Nov. 30, 1994 [JP] Japan ..................................... 6-297071
Feb. 7, 1995 [JP] Japan ..................................... 7-019378

[51] Int. Cl.$^6$ ....................................................... A61B 8/00
[52] U.S. Cl. ................... 128/660.07; 73/602; 73/861.25
[58] Field of Search ......................... 128/660.05, 660.06, 128/660.07, 660.08, 660.09, 661.01, 661.04, 661.10, 916, 661.09; 73/602, 607, 861.25

[56] References Cited

U.S. PATENT DOCUMENTS 4,662,222  5/1987  Johnson ..................................... 73/602
5,357,964 10/1994  Spivey et al. ........................ 128/661.09
5,415,171  5/1995  Goh et al. ........................... 128/660.07

Primary Examiner—George Manuel
Attorney, Agent, or Firm—Staas & Halsey

[57] ABSTRACT

An ultrasonic diagnostic system incorporates therein a technique of extracting an outline of the tissue within the subject. The ultrasonic diagnostic system is functionally capable of objectively extracting the outline of the tissue without a manual work, or with only a simple manual work. A gradient on each point of a tomographic image is evaluated, a scalar quantity representative of the magnitude of the gradient is evaluated, a maximal point of the scalar quantity is evaluated, and the outline of the tissue is extracted on the basis of the maximal point thus evaluated. When the outline is extracted, an arithmetic effective domain is determined beforehand so that the outline is extracted only within the determined arithmetic effective domain. Further, a movement of the subject, which extends through a plurality of frames, is detected to vary the outline on the basis of the movement detected.

41 Claims, 41 Drawing Sheets

| -n | -n+1 | ...... | -1 | 0 | 1 | ...... | n-1 | n |

(2n+1) × (2n+1)

| -n | -n+1 | ...... | -1 | 0 | 1 | ...... | n-1 | n |
|---|---|---|---|---|---|---|---|---|
| ...... | ...... | ...... | ...... | ...... | ...... | ...... | ...... | ...... |
| -n | -n+1 | ...... | -1 | 0 | 1 | ...... | n-1 | n |
| ...... | ...... | ...... | ...... | ...... | ...... | ...... | ...... | ...... |
| -n | -n+1 | ...... | -1 | 0 | 1 | ...... | n-1 | n |

(2n+1) × (2n+1)

| -n | ... | -n | ... | -n |
|---|---|---|---|---|
| -n+1 | ... | -n+1 | ... | -n+1 |
| ...... | ... | ...... | ... | ...... |
| -1 | ... | -1 | ... | -1 |
| 0 | ... | 0 | ... | 0 |
| 1 | ... | 1 | ... | 1 |
| ...... | ... | ...... | ... | ...... |
| n-1 | ... | n-1 | ... | n-1 |
| n | ... | n | ... | n |

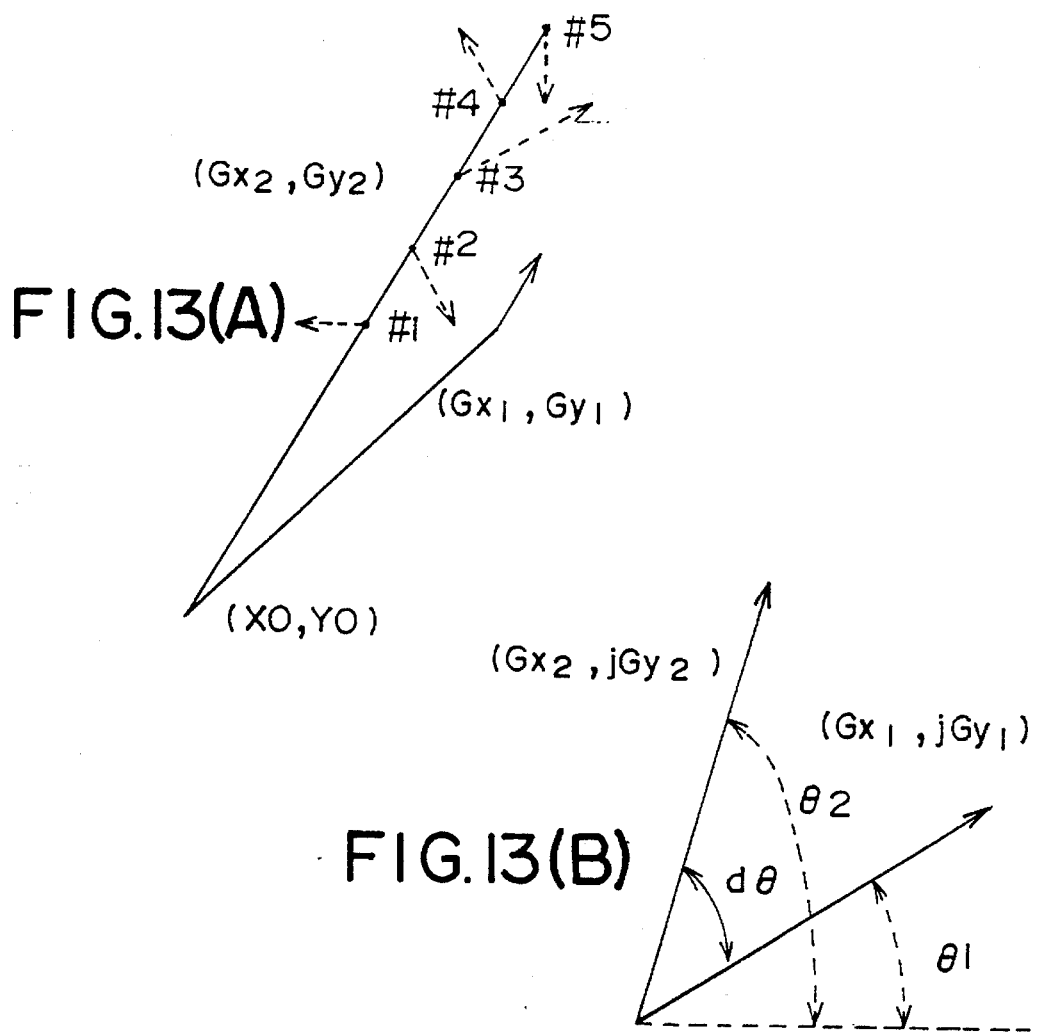
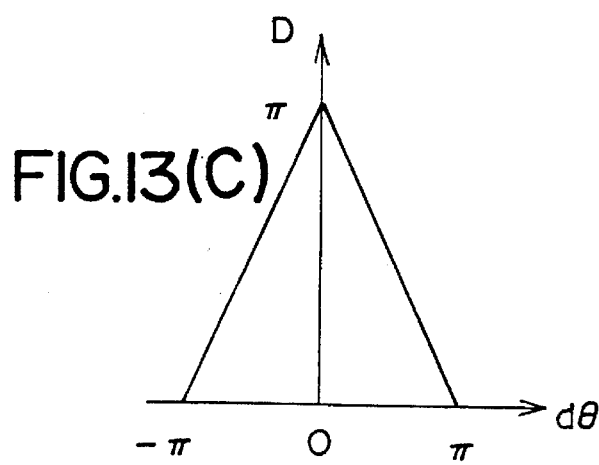

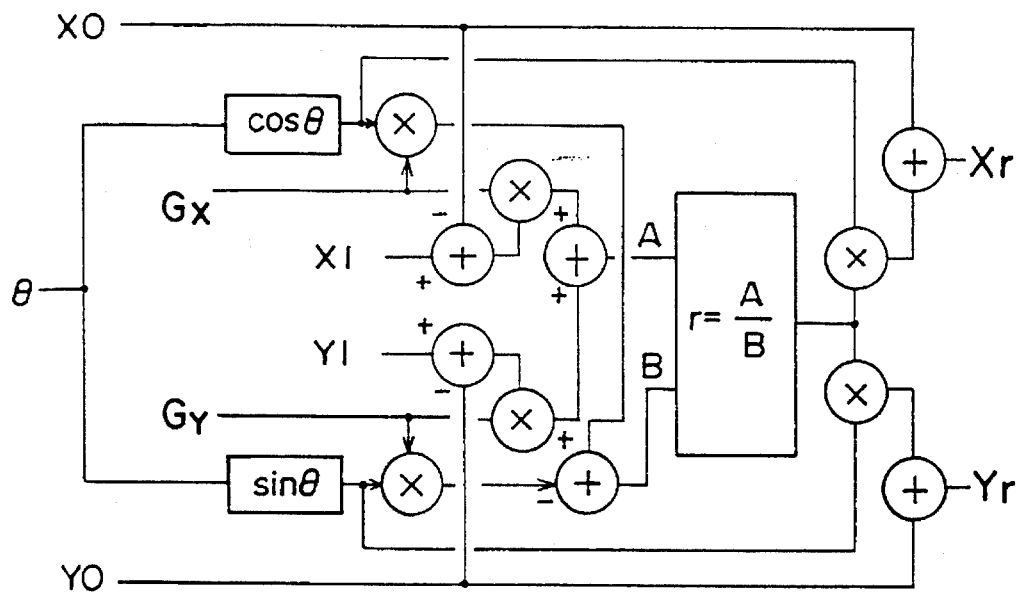
F I G. 16
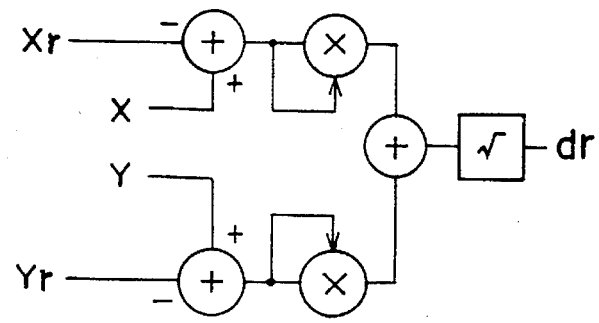
F I G. 17

CANDIDATE POINTS △

CANDIDATE POINTS OF BOTH EDGES ▲

OUTLINE □

CANDIDATE POINTS ○ OF PRECEDING FRAME

CANDIDATE POINTS △ OF CURRENT FRAME

OMITTING POINTS ● AND EDGE POINTS ▲

OUTLINE □

BINARY IMAGE

```
x x . . . . . . x x x
x . . x x x . . . x x
. . x x x x x . . . x
. . x x x x x x . . .
. . x x . . x x . . .
. . x x x + x x . . .
. . x x x . . x . . .
. . x x x x x x . . .
. . x x . . . x . . .
. . . . . x . . . . .
. . x x x x x . . . .
```

LABELLING IMAGE

```
0 0 . . . . . 2 2 2
0 . . 1 1 1 . . . 2 2
. . 1 1 1 1 1 . . . 2
. . 1 1 1 1 1 1 . . .
. . 1 1 . . 1 1 . . .
. . 1 1 1 + 1 1 . . .
. . 1 1 1 . . 1 . . .
. . 1 1 1 1 1 1 . . .
. . 1 1 . . . 1 . . .
. . . . . 3 . . . . .
. . 3 3 3 3 3 . . . .
```

BOUNDARY LINE

BOUNDARY POINTS □ AND CONTOUR POINTS △

CORRECTED CONTOUR POINTS ▲

OUTLINE

BOUNDARY POINTS ☐ AND BLOOD FLOW SECTION ●

BLOOD FLOW SECTION WITHIN BOUNDARY

OUTLINE

ULTRASONIC DIAGNOSTIC SYSTEM

BACKGROUND OF THE INVENTION

1. Field of the Invention

The present invention relates to an ultrasonic diagnostic system in which a tomographic image of the subject according to the ultrasounds is obtained, and more particularly to an ultrasonic diagnostic system which incorporates therein the technique for extracting the outline of a tissue within the subject.

2. Description of the Related Art

Hitherto, there has been used an ultrasonic diagnostic system in which ultrasonic beams are transmitted into the inside of the subject and the ultrasounds reflected from the inside of the subject are received to obtain received signals, so that a tomographic image of the subject is displayed on the basis of the received signals for diagnosis of diseases of the viscera and the like of the human body. Recently, in order to more facilitate the diagnosis of diseases, it is required that the outline of the tissue appearing on the tomographic image, for example, the left ventricle of the heart, is extracted and displayed, or area of a domain surrounded by such an outline and volume of the tissue estimated from the outline are displayed.

To extract the outline, simply, as shown in FIG. 45, an operator may trace, with for example a light-pen 2, the tomographic image displayed on a display unit 1 along the outline of a desired tissue. Thus, it is possible to extract the outline through the locus of the light-pen 2.

Further, as shown in FIG. 46, there has been proposed a technique in which a domain 3 is designated in such a manner that a desired tissue is surrounded using, for example, a track ball, a mouse or the like, and image data within the designated domain is binarized with a suitable threshold to extract an outline (Tosikazu Yagi, et al. "Measurement of sectional area of left ventricle and volume of left ventricle according to acoustic quantification method; Influence of set site for domain of concern", pp.517–518, Literature of No. 63 Meeting of Japan Ultrasonic Medical Institute, published on November, 1993).

However, according to the former involved in the method in which the outline is traced by a person, there is a need to carefully trace the tomographic image so as to prevent the locus by the light-pen or the like from being out of the outline. In addition, in case of the left ventricle which is the tissue of which an outline is to be obtained, there will be a need to repeatedly perform such a tracing operation for a lot of tomographic images over a pulse of movement of the heart in its entirety. This often involves inaccuracy in data lacking objectivity in spite of the fact that it is troublesome, and thus it is far from practical use.

Further, also in the later involved in the method in which an outlined domain 3 is designated and image data within the designated domain is binarized, thereby extracting an outline, there is a need to carefully perform the designation of the domain for each tomographic image, since the heart is always beating and repeats the expansion and contraction. For example, as shown in FIG. 46(A), if the inside of the domain 3 includes not only the left ventricle 4 but also the left atrium and the right ventricle, or as shown in FIG. 46(B), if a part of the left ventricle 4 is out of the domain 3, there will be evaluated erroneous values in both the area and the volume of the left ventricle 4. In order to avoid this problem, there is a need to carefully surround only the left ventricle 4 in its entirety through a manual work. Thus, the problem involving troublesomeness is not solved, while it is less troublesome than tracing the outline. Further, according to the method in which image data within the designated domain 3 is binarized to extract an outline, a luminance (the size of image data) is varied in accordance with the affect due to the noise and the like, and the place. Thus, it happens that a contour lacking a continuity as a two-dimensional image, or a contour forming no closed surface is extracted.

In view of the foregoing, it is an object of the present invention to provide an ultrasonic diagnostic system that are functionally capable of objectively extracting an outline of the tissue without a manual work, or with a simple manual work.

It is another object of the present invention to provide an ultrasonic diagnostic system having such a function that the mere input of outlines as to a small number of frames permits outlines as to a large number of frames to be extracted.

SUMMARY OF THE INVENTION

To attain the above-mentioned objects of the invention, according to the first ultrasonic diagnostic system of the present invention, there is provided an ultrasonic diagnostic system wherein ultrasonic waves reflected within a subject are received, whereby image data corresponding to each point inside a tomographic surface spreading within the subject is obtained, said system comprising:

(1) gradient arithmetic means for evaluating gradients of the image data on a plurality of points within the tomographic surface;

(2) scalar quantity arithmetic means for evaluating scalar quantities each corresponding to an associated one of said gradients on the plurality of points within the tomographic surface;

(3) maximal point arithmetic means for evaluating a plurality of maximal points within the tomographic surface so that said scalar quantities assume each a maximal value; and (4) outline extracting means for determining an outline of a predetermined tissue within the subject on the basis of said plurality of maximal points.

In the system as mentioned above, it is preferable that (5) said maximal point arithmetic means evaluates said maximal points on a plurality of assigned lines extending inside the tomographic surface on the basis of a variation of said scalar quantity in a direction along each of said plurality of assigned lines, and that said maximal point arithmetic means adopts, as said plurality of assigned lines, a plurality of assigned lines extending radially inside the tomographic surface taking a predetermined central point within the tomographic surface as a starting point.

Further, in a case where the maximal point arithmetic means evaluates said maximal points on a plurality of assigned lines extending inside the tomographic surface, as recited in the above item (5), it is preferable that (6) said maximal point arithmetic means comprises means for sequentially performing arithmetic on a difference between the scalar quantities on a plurality of points adjacent to each other along said assigned line to detect a variable point at which a sign of the difference is varied, means for correcting the scalar quantity on the variable point on the basis of the scalar quantity on a point near to the variable point, and means for deciding whether the variable point is to be extracted as the maximal point on the basis of a sign of the difference on the variable point when the scalar quantity corrected on the variable point is used.

In the system as mentioned above, it is acceptable that, for example, (7) the gradient arithmetic means is arranged to perform a differentiation in two directions mutually different inside the tomographic surface.

(8) It is preferable that said gradient arithmetic means is arranged to perform a two-dimensional differentiating operation using a differentiating filter having a width between 0.5 times and twice as long as a width of one which is narrower in width with respect to a differentiating direction than that of another of two tissues contacting with said outline to be extracted, said two tissues appearing on the tomographic surface.

Further, in the system as mentioned above, it is preferable that (9) the scalar quantity arithmetic means recited in the above item (2) is arranged to evaluate, as said scalar quantity, at least one selected from among an absolute value of the gradient, a function taking the absolute value as its variable, a sum of absolute values of the gradient as to components with respect to mutually different two directions on the tomographic surface, a function taking said sum as its variable.

In the system as mentioned above, when the outline is determined using the outline extracting means recited in the above item (4), it is preferable that the outline extracting means has (4–1) characteristic quantity arithmetic means for evaluating characteristic quantity representative of a probability such that said maximal points are points on said outline, and said outline extracting means is arranged to extract the points on said outline from among said maximal points on the basis of said characteristic quantity and determine said outline through coupling the points on said outline.

When the maximal point arithmetic means recited in the above item (3) satisfies the conditions of the above item (5), in other words, when the maximal point arithmetic means evaluates said maximal points on a plurality of assigned lines extending inside the tomographic surface on the basis of a variation of said scalar quantity in a direction along each of said plurality of assigned lines, it is preferable that outline extracting means is arranged to extract the points on said outline from among said maximal points on the basis of said characteristic quantity and determine said outline through coupling the points on said outline, wherein said characteristic quantity includes at least one or a plural combination selected from among (a) the scalar quantity of the maximal point, or a function taking the scalar quantity as its variable, (b) an average value of the image data associated with a predetermined domain including a point corresponding to the maximal point, or a function taking the average value as it variable, (c) a sign of a scalar product of a vector along the assigned line and a gradient of the maximal point on the assigned line, or a numerical value representative of the sign, (d) an angle formed by gradients on first and second said maximal points located respectively on mutually different first and second said assigned lines, or a function taking the angle as its variable, and (e) a distance between an intersection of a straight line passing through the maximal point located on the first assigned line among mutually different first and second said assigned lines and extending in a direction perpendicular to the direction of the gradient of the maximal point and the second assigned line and the maximal point located on the second assigned line, or a function taking the distance as its variable.

In the system as mentioned above, when the outline extracting means recited in the above item (4) has the characteristic quantity arithmetic means recited in the above item (4–1), it is preferable that the outline extracting means further comprises:

(4–2A) candidate point extracting means for determining an outline candidate point having a probability that it exists on the outline, from among the maximal point, on the basis of said characteristic quantity; and (4–3A) contour point extracting means for adopting the outline candidate point as the point on the outline when a distance between the outline candidate point determined by said candidate point extracting means and a point on the outline adjacent to the outline candidate point is within a predetermined distance.

In the system as mentioned above, when the outline extracting means recited in the above item (4) has the characteristic quantity arithmetic means recited in the above item (4–1), alternatively, it is also preferable that the outline extracting means further comprises:

(4–2B) candidate point extracting means for determining on the basis of the characteristic quantity evaluated on a predetermined frame of a plurality of frames each representative of a same tomographic surface at different time an outline candidate point having a probability that it exists on the outline, from among the maximal point in said predetermined frame; and (4–3B) contour point extracting means for adopting the outline candidate point as the point on the outline in said predetermined frame when a distance between the outline candidate point in said predetermined frame determined by said candidate point extracting means and a point on the outline in a frame different from said predetermined frame of said plurality of frames, which point is associated with said outline candidate point, is within a predetermined distance.

Further, in a case where said subject is the heart of a human body, and said system serves to determine an outline of a left ventricle as said outline, it is also preferable that said system has

(10) valve source detecting means for detecting boundary points between two valves existing the left ventricle and a left atrium and a septum of the left ventricle, appearing on the tomographic surface; and said outline extracting means recited in the above item (4), which is provided with the characteristic quantity arithmetic means recited in the above item (4–1), extracts on the basis of the characteristic quantity the point on the outline in a domain excepting an area formed when the boundary points are coupled to each other, on the tomographic surface.

Specifically, for example, when said outline extracting means recited in the above item (4) comprises the characteristic quantity arithmetic means recited in the above item (4–1), the candidate point extracting means recited in the above item (4–2A), and the contour point extracting means recited in the above item (4–3A), it may be so arranged that said valve source detecting means recited in the above item

(10) adopts it as at least one of criteria that a distance between a first outline candidate point determined by said candidate point extracting means and a point on the outline adjacent to the first outline candidate point is within a predetermined distance, and a distance between the first outline candidate point and a second point adjacent to the first outline candidate point is over a predetermined distance, so that the first outline candidate point is extracted as the boundary point.

It is acceptable that the "predetermined distance" referred to in the valve source detecting means is different from the "predetermined distance" referred to in the contour point extracting means recited in the above item (4–3A).

When said outline extracting means recited in the above item (4) comprises the characteristic quantity arithmetic means recited in the above item (4–1), the candidate point extracting means recited in the above item (4–2B), and the contour point extracting means recited in the above item (4–3B), alternatively, it also may be so arranged that said valve source detecting means recited in the above item (10) adopts it as at least one of criteria that a distance between the outline candidate point in said predetermined frame determined by said candidate point extracting means and a point on the outline in a frame different from said predetermined frame of said plurality of frames, which point is associated with said outline candidate point, is over a predetermined distance, so that the outline candidate point is extracted as the boundary in said predetermined frame.

It is acceptable that the "predetermined distance" referred to in the valve source detecting means is different from the "predetermined distance" referred to in the contour point extracting means recited in the above item (4–3B).

Further, in the system described above, it is preferable that the system further comprises an outline display means for displaying at least one of a contour coupling the points on the outline with a straight line or a curve, and a picture plane in which an inside and an outside of the outline are distinguished from each other by a color, a luminance or a pattern.

Furthermore, in the system described above, it is preferable that the system further comprises area arithmetic means for evaluating an area of an inside of the outline extracted by said outline extracting means recited in the above item (4), and area display means for displaying the area evaluated by said area arithmetic means. In this case, it is preferable that said area display means displays the area with at least one of figures representative of the area and a graph indicative of variation in time of the area.

Still further, in the system described above, it is preferable that the system further comprises volume arithmetic means for evaluating volume of an inside of the outline extracted by said outline extracting means recited in the above item (4), and volume display means for displaying the volume evaluated by said volume arithmetic means. In this case, it is preferable that said volume display means displays the volume with at least one of figures representative of the volume and a graph indicative of variation in time of the volume.

To attain the objects of the present invention, according to the second ultrasonic diagnostic system of the present invention, there is provided an ultrasonic diagnostic system wherein ultrasonic waves reflected within a subject are received, whereby image data corresponding to each point inside a tomographic surface spreading within the subject is obtained, said system comprising:

(12) outline arithmetic means for evaluating an outline of a predetermined tissue within the subject on the basis of the image data;

(13) gradient arithmetic means for evaluating gradients of the image data on a plurality of points inside the tomographic surface; and

(14) arithmetic effective domain detecting means for determining an arithmetic effective domain including said predetermined tissue within the tomographic surface on the basis of directions of said gradients, wherein said outline arithmetic means (item (12)) determines the outline of said predetermined tissue inside the arithmetic effective domain.

In the system as mentioned above, said arithmetic effective domain detecting means (item (14)) may be arranged in such a manner to detect the arithmetic effective domain on the basis of a distribution of binarized image data within the tomographic surface, said binarized image data being produced in such a manner that the image data associated with each point within the tomographic surface is binarized on the basis of an angle formed with a direction of the assigned line starting from a predetermined central point within the tomographic surface and extending through the point on which the gradient is evaluated within the tomographic surface and a direction of the gradient at the point on which the gradient is evaluated.

The second ultrasonic diagnostic system of the present invention may be arranged in such a manner that the first ultrasonic diagnostic system of the present invention is incorporated thereinto without any changes. In such a case, the outline arithmetic means (item (12)) in the second ultrasonic diagnostic system of the present invention may basically comprise:

(12–1) scalar quantity arithmetic means for evaluating scalar quantities each corresponding to an associated one of said gradients on a plurality of points within the tomographic surface;

(12–2) maximal point arithmetic means for evaluating a plurality of maximal points within the arithmetic effective domain so that said scalar quantity assumes a maximal value;and (12–3) outline extracting means for determining an outline of said predetermined tissue on the basis of said plurality of maximal points.

It is preferable, similar to the outline extracting means (item (4)) in the first ultrasonic diagnostic system of the present invention, that said outline extracting means (item (12–3)) has characteristic quantity arithmetic means for evaluating characteristic quantity representative of a probability such that said maximal points are points on said outline, and said outline extracting means is arranged to extract the points on said outline from among said maximal points on the basis of said characteristic quantity and determine said outline through coupling the points on said outline.

When the maximal point arithmetic means (item (12–2)) evaluates said maximal point on a plurality of assigned lines extending inside the tomographic surface on the basis of a variation of said scalar quantity in a direction along each of said plurality of assigned lines, similar to the case of the first ultrasonic diagnostic system of the present invention, it is preferable that outline extracting means is arranged to extract the points on said outline from among said maximal points on the basis of said characteristic quantity and determine said outline through coupling the points on said outline, wherein said characteristic quantity includes at least one or a plural combination selected from among (a) the scalar quantity of the maximal point, or a function taking the scalar quantity as its variable, (b) an average value of the image data associated with a predetermined domain including a point corresponding to the maximal point, or a function taking the average value as it variable, (c) a sign of a scalar product of a vector along the assigned line and a gradient of the maximal point on the assigned line, or a numerical value representative of the sign, (d) an angle formed by gradients on first and second said maximal points located respectively on mutually different first and second said assigned lines, or a function taking the angle as its variable, and (e) a distance between an intersection of a straight line passing through the maximal point located on the first assigned line among mutually different first and second said assigned lines and extending in a direction perpendicular to the direction of the gradient of the maximal point and the second assigned line and the maximal point located on the second assigned line, or a function taking the distance as its variable.

The second ultrasonic diagnostic system of the present invention may be arranged in a different way from the first ultrasonic diagnostic system of the present invention. In this case, it is permissible to adopt, as the outline arithmetic means (item (12)), for example, the outline arithmetic means for extracting an outline through binarizing image data, as explained referring to FIG. 46.

It is preferable that the second ultrasonic diagnostic system of the present invention further comprises

(15) display means for displaying the outline.

Further, it is preferable that the second ultrasonic diagnostic system of the present invention further comprises

(16) induced quantity calculating means for evaluating induced quantity to be calculated on the basis of the outline determined by said outline arithmetic means.

In this case, it is preferable that the said induced quantity calculating means is arranged to evaluate, as said induced quantity, at least one selected from among an area of an inside of the outline, a position of the center of gravity of the outline and a volume of the inside of the outline.

In a case where the second ultrasonic diagnostic system of the present invention is provided with the induced quantity calculating means (item (16)), it is preferable that the system further comprises

(17) display means for displaying at least one of the induced quantity and variable quantity over a plurality of frames of the induced quantity.

To attain the objects of the present invention, according to the third ultrasonic diagnostic system of the present invention, there is provided an ultrasonic diagnostic system wherein ultrasonic waves reflected within a subject are received, whereby image data corresponding to each point inside a tomographic surface spreading within the subject is obtained, said system comprising:

(18) movement calculating means for calculating movements on a plurality of points within the tomographic surface on the basis of the image data as to a plurality of frames;

(19) outline arithmetic means for evaluating an outline of a predetermined tissue within the subject on the basis of the image data; and

(20) outline modifying means for providing an outline modified from the outline evaluated by said outline arithmetic means on the basis of the movements detected by said movement calculating means.

In the third ultrasonic diagnostic system of the present invention, it is preferable that said movement calculating means is arranged to calculate, as said movement, any of a vector of a two-dimensional movement within the tomographic surface and a magnitude of movement with respect to a predetermined direction within the tomographic surface, using any of an optical flow method and a cross correlation method. In this case, said predetermined direction may be involved in directions of a plurality of assigned lines extending radially inside the tomographic surface taking a predetermined central point of inside of the outline as a starting point.

It is preferable that said movement calculating means (item (18)) calculates the movements on the plurality of points as to each of a plurality of domains set up within the tomographic surface, extracts the movement thus calculated, which is deemed to have a high probability that an exact movement is represented, as to each of said plurality of domains, and determines a representative of the movement thus extracted as to each of said plurality of domains.

Further, it is preferable that the third ultrasonic diagnostic system of the present invention is provided with

(21) preprocessing means for practicing one of a smoothing treatment and a binarizing treatment for the image data, and said movement calculating means (item (18)) calculates the movements on the basis of the image data subjected to the one of the treatments by said preprocessing means.

The third ultrasonic diagnostic system of the present invention may be arranged in such a manner that the first ultrasonic diagnostic system of the present invention is incorporated thereinto without any changes, alternatively both the first and second ultrasonic diagnostic system of the present invention are incorporated thereinto without any changes. In such a case, the outline arithmetic means (item (19)) in the third ultrasonic diagnostic system of the present invention may basically comprise:

(19-1) gradient arithmetic means for evaluating gradients of the image data on a plurality of points within the tomographic surface;

(19-2) scalar quantity arithmetic means for evaluating scalar quantities each corresponding to an associated one of said gradients on the plurality of points within the tomographic surface;

(19-3) maximal point arithmetic means for evaluating a plurality of maximal points within the tomographic surface so that said scalar quantities assume each a maximal value; and (19-4) outline extracting means for determining an outline of a predetermined tissue within the subject on the basis of said plurality of maximal points.

The third ultrasonic diagnostic system of the present invention may be arranged in a different way from the first and second ultrasonic diagnostic systems of the present invention. In this case, it may be so arranged that the system is provided with

(22) a contour point designation handler for designating a contour point located on the outline of said predetermined tissue, and said outline arithmetic means (item (19)) evaluates the outline on the basis of the contour point designated by said contour point designation handler.

It is preferable that the third ultrasonic diagnostic system of the present invention is provided with

(23) synchronizing signal generating means for generating a beat synchronizing signal synchronized with a beat of the heart of the subject, and said outline arithmetic means (item (19)) evaluates the outline on the basis of the beat synchronizing signal.

Further, it is preferable that the third ultrasonic diagnostic system of the present invention is provided with

(24) memory means for storing the image data of a plurality of frames on an overwrite-feasible basis, and

(25) freeze means for inhibiting an overwrite to said memory means, wherein said outline arithmetic means (item (19)) evaluates the outline as to at least one sheet of predetermined frame among a plurality of frames stored in said memory means (item (24)) in a freeze state that the overwrite is inhibited by said freeze means (item (25)), said movement detecting means (item (18)) calculates the movement as to the other frames except the predetermined frame among the plurality of frames stored in said memory means (item (24)) in the freeze state, and said outline modifying means (item (20)) evaluates an outline modified from the outline which is determined by said outline arithmetic means.

It is preferable, similar to the second ultrasonic diagnostic system of the present invention, that the third ultrasonic diagnostic system of the present invention is provided with

(25) display means for displaying the outline.

It is also preferable that the third ultrasonic diagnostic system of the present invention is provided with

(26) induced quantity calculating means for evaluating induced quantity to be calculated on the basis of at least one of the outline determined by said outline arithmetic means and the outline modified by said outline modifying means.

In this case, it is preferable that said induced quantity calculating means (item (26)) is arranged to evaluate, as said induced quantity, at least one selected from among an area of an inside of the outline, a position of the center of gravity of the outline and a volume of the inside of the outline.

In a case where the third ultrasonic diagnostic system of the present invention is provided with the induced quantity calculating means (item (26)), it is preferable that the system is provided with

(27) display means for displaying at least one of the induced quantity and variable quantity over a plurality of frames of the induced quantity.

The first ultrasonic diagnostic system of the present invention is provided with the structural elements (1)–(4) referenced above. Consequently, according to the present invention, it is possible to perform the objective extraction of an outline of the tissue without any manual operation or a very simple manual operation such that a point or a single segment on a display screen for a tomographic image for example is designated.

Further, in the first ultrasonic diagnostic system of the present invention, if a conception such as the assigned lines described in the above item (5), it is sufficient for detection of maximal points of scalar quantity to perform arithmetic on difference between scalar quantity-to-scalar quantity on the adjacent points on the assigned line. Thus, according to the present invention, it is possible to readily find the maximal point. And as those assigned lines, if the assigned lines, which are extending radially from a predetermined central point, are adopted, it means to locate points on the outline radially from the central point. Thus, it is possible to adopt the same algorithm with respect to any directions (any assigned lines) to locate the points on the outline.

If the system is provided with the maximal point arithmetic means which satisfies the condition of the above item (6), there will be reduced a possibility such that the maximal point is erroneously detected owing to the noise and the like included in the image data.

The gradient arithmetic means of the above item (1) may be constituted of means for performing a two-dimensional differentiation, for example, as shown in the above item (7). In this case, it is sufficient for such a differentiating operation to perform a differentiation with respect to, for example, the longitudinal direction and the lateral direction of the tomographic image, using a well known differentiating filter. Thus, it is possible to implement the gradient arithmetic means with a relatively simple structure.

In such a case, as described in the above item (8), it is preferable to adopt a differentiating filter having a width between 0.5 times and twice as long as a width of one which is narrower in width with respect to a differentiating direction than that of another of two tissues.

The reason why such a differentiating filter as mentioned above is adopted is as follow:

In case of the use of a differentiating filter having its width less than 0.5 times as long as a width of the narrower one of two tissues, it unfavorably happens that a small differential value (a component of gradient in its differential direction) is evaluated even on the outline to be extracted, and as a result, the outline cannot be favorably extracted. On the other hand, in case of the use of a differentiating filter having its width exceeding twice as long as a width of the narrower one of two tissues, the difference between a differential value on the point of the outline and a differential value on the peripheral point is small, so that the evaluated differential values vary gently as a whole. This causes a hazy outline.

With respect to the scalar quantity arithmetic means of the above item (2) in the first ultrasonic diagnostic system of the present invention, anyone is acceptable, as the scalar quantity, which is involved in the quantity, among a direction and a magnitude (absolute value of the gradient) which constitute the gradient, corresponding to the magnitude. It is possible to select any of the quantities set forth in the above item (9) for example.

In the first ultrasonic diagnostic system of the present invention, when the outline is determined using the outline extracting means of the above item (4), as mentioned above, it is preferable to arrange the system in such a manner that the system is provided with characteristic quantity arithmetic means for evaluating characteristic quantity representative of a probability such that said maximal points are points on said outline, and the outline is determined on the basis of the characteristic quantity thus evaluated. In such a case, it is preferable that at least one or a plural combination of the above-mentioned items (a)–(e) is included in the above-mentioned characteristic quantity. When the above-mentioned items (a)–(e) are adopted as the characteristic quantity, respectively, the associated effect on each is as follows.

(a) A scalar quantity of the maximal point

The scalar quantity is, as mentioned above, a quantity corresponding to the magnitude of the gradient of the maximal point, and is representative of a degree of variation of the image data at the maximal point. Thus, it is possible to adopt the scalar quantity as the characteristic quantity.

(b) An average value of the image data at a point corresponding to the maximal point An average value of the image data of two tissues, which are adjacent to each other across the outline, is usually remarkably varied. Accordingly, it is possible to use also the value of the image data itself as the characteristic quantity. It is noted that what is meant by the corresponding point is a point which is away from the maximal point in a gradient direction of the maximal point at a distance of about half of the width of the tissue (for example, the myocardium) to which the corresponding point belongs. The reason why taking an average is performed is that the value of the image data may vary owing to the influence of the noise and the like, if only one point is involved in determination of the image data.

(c) A sign of a scalar product of gradient-to-gradient

As described above, an average value of the image data of two tissues, which are adjacent to each other across the outline, is usually remarkably varied. Accordingly, in the outline section, a vector direction of the gradient is always directed from one of the tissues to the other. Thus, it is possible to adopt the above-mentioned sign as the characteristic quantity.

(d) An angle

An outline is continuous. Therefore, for example, the gradients of the contour points on the neighboring assigned lines are directed to the approximately same direction. In other words, it is considered that the angle of the gradient-to-gradient is small. Thus, it is possible to adopt the angle mentioned above as the characteristic quantity.

(e) A distance

As mentioned above, an outline is continuous. Therefore, there is a high probability such that the shorter distance is involved in the point on the outline. Thus, it is possible to adopt the distance as the characteristic quantity.

In the first ultrasonic diagnostic system of the present invention, when the outline extracting means recited in the above item (4) has the characteristic quantity arithmetic means recited in the above item (4–1), and in addition the candidate point extracting means of the above item (4–2A) and the contour point extracting means of the above item (4–3A), or when the outline extracting means recited in the above item (4) has the characteristic quantity arithmetic means recited in the above item (4–1), and in addition the candidate point extracting means of the item (4–2B) and the contour point extracting means of the item (4–3B), it is possible to prevent the adjacent contour points from being erroneously detected on positions which are far away from each other, thereby performing extraction of the outline with greater accuracy.

Further, in a case where said subject is the heart of a human body, and said system serves to determine an outline of a left ventricle as said outline, if the system is provided with the valve source detecting means of the above item (10), and said outline extracting means recited in the above item (4), which is provided with the characteristic quantity arithmetic means recited in the above item (4–1), extracts on the basis of the characteristic quantity the point on the outline in a domain excepting an area formed when the boundary points are coupled to each other, on the tomographic surface; in other words, if the system is arranged in such a manner that even if the point, which is deemed to be a point on the outline, is extracted within the area formed when the boundary points are coupled to each other, such a point is not regarded as the point on the outline and be omitted, it is possible to avoid an erroneous extraction of the outline due to the movement of the value.

As the valve source detecting means recited in the above item (10), in a similar fashion to the case of the above item(4–2A) and the above item (4–3A), or the above item (4–2B) and the above item (4–3B), it is possible to adopt means for extracting the boundary point located at the source of the valve taking it as at least one of criteria whether the adjacent outline candidate point is over a predetermined distance.

Further, according to the system described above, there is provided an outline display means for displaying at least one of a contour coupling the points on the outline with a straight line or a curve, and a picture plane in which an inside and an outside of the outline are distinguished from each other by a color, a luminance or a pattern. Furthermore, according to the system described above, an area of an inside of the outline and volume of the same are evaluated, and the evaluated area and volume massages are displayed. Thus, it is possible to obviously provide information effective for observation and diagnostic. Still further, in the system described above, while it is acceptable to display the area or volume with figures, the display of the area or volume with a graph indicative of variation in time of the volume makes it possible for an operator to see at once the behavior of the tissue in expansion and contraction due to the beat of the heart and the like, and thus it is more effective.

The second ultrasonic diagnostic system of the present invention comprises the elements of the above items (12)–(14), wherein the outline is determined inside the arithmetic effective domain. Thus, for example, in the method explained referring to FIG. 46, there in no need to manually designate the approximate area 3. According to the present invention, there is solved such a problem, which is involved in a case where the approximate area 3 is manually designated, that an unnecessary domain is included, or a necessary domain is excluded, owing to the expansion and contraction of the heart for example, thereby determining the outline with great accuracy.

The second ultrasonic diagnostic system of the present invention determines, as described above, an outline within an arithmetic effective domain. Thus, when the second ultrasonic diagnostic system of the present invention is applied to the first ultrasonic diagnostic system of the present invention in which an outline is detected on the basis of a maximal point of the scalar quantity corresponding to the gradient, even if a point, which is deemed to be a contour point, is extracted at the position out of the arithmetic effective domain, such a point is not regarded as the contour point and be omitted, and the contour point is detected only inside the arithmetic effective domain. Thus, it is possible to perform extraction of the outline with greater accuracy.

In the second ultrasonic diagnostic system of the present invention, as said arithmetic effective domain detecting means (item (14)), it may be arranged in such a manner to detect the arithmetic effective domain on the basis of a distribution of binarized image data within the tomographic surface, said binarized image data being produced in such a manner that the image data associated with each point within the tomographic surface is binarized on the basis of an angle formed with a direction of the assigned line starting from a predetermined central point within the tomographic surface and extending through the point on which the gradient is evaluated within the tomographic surface and a direction of the gradient at the point on which the gradient is evaluated. In such a case, specifically, when the outline of the left ventricle is extracted, the arithmetic effective domain, which may cover completely the left ventricle, is determined. Thus, it is possible to extract the outline of the left ventricle with greater accuracy.

The third ultrasonic diagnostic system of the present invention is provided with the structural elements of the above items (18)–(20). Consequently, it is possible to determine the outlines as to the series of frames, respectively, through modifying the outline determined as to a certain frame according to the movement of plural points within the tomographic image, without performing from the beginning arithmetic to determine the outline on each frame. Incidentally, when the outline is modified, it is acceptable to directly modify the outline determined by the outline arithmetic means, or to further modify the outline thus modified.

The movement on each point within the tomographic image can be determined using, for example, an optical flow method or a cross correlation method.

Next, there will be explained the optical flow method and the cross correlation method.

Optical flow method

The optical flow method is a method in which apparent velocity of dynamic image is calculated. With respect to details, refer to Koga, Miike, "Dynamic Image Process by Personal Computer" published by Molikita.

Assuming that spatial coordinates on a tomographic surface is expressed by (x, y); time t; luminance on image P(x, y, t), a movement involving no luminance variation is expressed by the following equation.

$$P(x, y, t) = P(x+\delta x, y+\delta y, t+\delta t) \quad (1)$$

Now, let the right side member be Taylor-expanded, and neglect the term of second degree and et eqq., then the following expression is given:

$$\left. \begin{array}{l} Px \cdot u + Py \cdot v + Pt = 0 \\ \text{where} \\ Px = \partial P/\partial x, Py = \partial P/\partial y, Pt = \partial P/\partial t \\ u = dx/dt, v = dy/dt \end{array} \right\} \quad (2)$$

In the above expression, Px and Py denote spatial gradients as to an x-direction and a y-direction, respectively; Pt a gradient on a time basis; and alphabetical letters u and v each an optical flow velocity to be calculated. To solve the expression (2), there is needed at least one additional restriction condition. A precision of the velocity (u, v) to be calculated is determined, according as how the restriction condition is applied. It does not directly concern the essence of the present invention as to how the restriction condition is applied. Hence, the typical scheme will be described hereinafter.

To provide an image which is smooth in spatially, or to minimize the spatial variation, the following condition is added, $$(\partial u/\partial x)^2 + (\partial u/\partial y)^2 + (\partial v/\partial x)^2 + (\partial v/\partial y)^2 \to \min. \quad (3)$$

and then the optical flow is determined so that the error function of the following expression is minimum.

$$E = \iint [\{Px \cdot u + Py \cdot v + Pt\}^2 + \quad (4)$$
$$\alpha^2 \{ux^2 + uy^2 + vx^2 + vy^2\}]dxdy$$

where $ux = \partial u/\partial x$, $uy = \partial u/\partial y$, $vx = \partial v/\partial x$, $vy = \partial v/\partial y$ Applying the expression (4) as the restriction condition permits the velocity (u, v) to be calculated to be spatially sufficiently smooth and to be the value satisfying the expression (2). Incidentally, $\alpha$ is to provide a relative weight between the expressions (2) and (3).

Through the calculus of variations, the following partial differential simultaneous equations are obtained.

$$\left. \begin{array}{l} Px^2 u + PxPy \ v = \alpha^2 \nabla^2 u - PxPt \\ Px^2 u + PxPy \ v = \alpha^2 \nabla^2 u - PxPt \end{array} \right] \quad (5)$$

Solving the above equations permits the optical flow velocity (u, v) to be obtained.

Alternatively, as another restriction condition, let us consider the following:

Apply such a condition that the optical flow is approximately constant in a local domain S, and consider minimization of the following expression in the spatial coordinates (i, j) included in the domain S.

$$E = \Sigma\Sigma[Px(i,j,k)u + Py(i,j,k)v + Pt(i,j,k)]^2 \quad (6)$$

In this case, the velocity components may be calculated, under conditions of $\partial E/\partial u = 0$, $\partial E/\partial v = 0$, in accordance with the following expressions:

$$\left. \begin{array}{l} u = -\frac{1}{\Delta} (\Sigma\Sigma Py^2 \Sigma\Sigma PtPx - \Sigma\Sigma PxPy \Sigma\Sigma PyPt) \\ v = -\frac{1}{\Delta} (-\Sigma\Sigma PxPy \Sigma\Sigma PtPx + \Sigma\Sigma Px^2 \Sigma\Sigma PyPt) \\ \text{where } \Delta = \Sigma\Sigma Py^2 \Sigma\Sigma Px^2 - (\Sigma\Sigma PxPy)^2 \end{array} \right] \quad (7)$$

Incidentally, while the two-dimensional optical flow velocity is calculated in accordance with the above examples, it is also acceptable to calculate the optical flow velocity with respect to only a predetermined one-dimensional direction.

Cross correlation method

With respect to the cross correlation method, when the cross correlation coefficient is given by r (m, n), it is acceptable to calculate, for example, the following expression:

$$r(m, n) = \Sigma\Sigma[P(i,j,t) - avP(i,j,t)][P(i + m, j + n, t + \Delta t) - \quad (8)$$
$$avP(i + m, j + n, t + \Delta t)]/sqrt[\Sigma\Sigma\{P(i,j,t) - avP(i,j,t)\}^2 \{P(i + m, j + n, t + \Delta t) - avP(i + m, j + n, t + \Delta t)\}^2]$$

And also it is acceptable that images are binarized beforehand and the cross correlation coefficient is calculated with respect to the binarized image data Q (i, j, t) in accordance with the following expression:

$$r(m,n) = \Sigma\Sigma Q(i,j,t)Q(i+m, j+n, t+\Delta t) \quad (9)$$

When the maximum value is retrieved from among the cross correlation coefficient r (m, n), m and n of concern are involved in the movement. In a case where the movement as to only a predetermined direction is detected, a replacement of the above-mentioned two-dimensional correlation function by a one-dimensional correlation function makes it possible to calculate a one-dimensional movement.

In any of the optical flow method and the cross correlation method, in a case where the movement as to only a predetermined direction is detected, adopting each direction of a plurality of assigned lines extending radially from a predetermined central point within the outline makes it possible to know the movement of the outline with greater accuracy through the one-dimensional operation. In this case, it is acceptable that the above-referenced "predetermined central point" is manually entered. On the other hand, it is also acceptable to determine the "predetermined central point" in such a manner that the center of gravity or the like of the inside of the outline regarding the frame on which the outline is already determined is evaluated, and the center of gravity or the like thus evaluated is adopted as the "predetermined central point".

Further, in a case where the movement calculating means (item (18)) calculates the movements on the plurality of points as to each of a plurality of domains set up within the tomographic surface, extracts the movement thus calculated, which is deemed to have a high probability that an exact movement is represented, as to each of said plurality of domains, and determines a representative of the movement thus extracted as to each of said plurality of domains, it is possible to exactly detect the movement of each domain within the tomographic surface thereby modifying exactly the outline.

Further, if the third ultrasonic diagnostic system of the present invention is provided with the preprocessing means of the above item (21), it is possible to detect the movement with more exact or simple arithmetic in the movement calculating means (item (18)). In this case, specifically, in a case where the movement calculating means adopts the optical flow method to calculate the movement, the use of the preprocessing means for practicing the smoothing treatment makes it possible to detect the movement with greater accuracy. On the other hand, in a case where the movement calculating means adopts the cross correlation method to calculate the movement, the use of the preprocessing means for practicing the binarizing treatment serves to simplify arithmetic, as shown in the expression (9), thereby detecting the movement at higher speed.

In the third ultrasonic diagnostic system of the present invention, if the outline arithmetic means (item(19)) is provided with the gradient arithmetic means, the scalar quantity arithmetic means, the maximal point arithmetic means, and the outline extracting means, as recited in the above items (19-1) to (19-4), respectively, these means as recited in the above items (19-1) to (19-4) are substantially the same as those as recited in the above items (1) to (4) in the first ultrasonic diagnostic system of the present invention, respectively. Thus, the third ultrasonic diagnostic system of the present invention may be arranged in such a manner that the first ultrasonic diagnostic system of the present invention is incorporated thereinto without any changes. According to the third ultrasonic diagnostic system of the present invention, in a case where a plurality of frames exist, the outline on each frame is not determined in the similar fashion to that of the first ultrasonic diagnostic system of the present invention. More in details, according to the third ultrasonic diagnostic system of the present invention, the outline as to a certain frame is determined in the similar fashion to that of the first ultrasonic diagnostic system of the present invention, whereas outlines as to the other frames are determined through modifying the outline.

In a case where the outline is determined in the similar fashion to that of the first ultrasonic diagnostic system of the present invention, it is acceptable to restrict the domain in which the outline is determined into the arithmetic effective domain, in a similar fashion to that of the second ultrasonic diagnostic system of the present invention. In this case, it is equivalent to such a situation that the third ultrasonic diagnostic system of the present invention incorporates thereinto the both the first and second ultrasonic diagnostic systems of the present invention.

The third ultrasonic diagnostic system of the present invention may be arranged in a different way from the first and second ultrasonic diagnostic systems of the present invention. In this case, for example, it may be so arranged that the system is provided with a contour point designation handler of the above item (22). It is acceptable that the outline arithmetic means (item (19)) evaluates the outline in any of such various fashions that the outlines entered through operation of the contour point designation handler are smoothly coupled to each other with the use of, for example, the spline function; when there are many entered contour points, for example, those contour points are simply coupled to each other with the broken line, without substantial arithmetic; and the outline entered manually or half-manually is modified taking account of the outline determined by the outline arithmetic means comprising, for example, means as recited in the above items (19-1) to (19-4). The outline arithmetic means referred to in the present invention stands for a technical concept including all the aspects as mentioned above.

In a case where the third ultrasonic diagnostic system of the present invention is provided with the synchronizing signal generating means (23), and the outline arithmetic means (item (19)) evaluates the outline as to the designated frame on the basis of the beat synchronizing signal, it may be so arranged that a frame synchronized with the beat, on which the outline can be determined exactly, is designated to determine the outline on the frame, whereas the outline as to another frame synchronized with the beat is determined through modifying the outline of the frame on which the outline has been determined. Thus, since the exact outline can be determined as the initial value, it is possible to determine the outlines as to all the frames with greater accuracy.

As the beat synchronizing signal, it is possible to adopt, for example, the electrocardiogram waveform signal, the Doppler waveform signal and the like.

Further, it is acceptable that the third ultrasonic diagnostic system of the present invention is provided with the memory means (item (24)) and the freeze means (item(25)), and is arranged so as to determine the outline as to a certain frame among a plurality of frames in a freeze state, whereas the outlines as to other frames are determined through modifying their outlines. In this case, when the outline is not determined with accuracy, it is permitted to implement fine work such that the outline is manually modified, or detailed observation such that the outline on each frame is carefully reviewed.

According to the second ultrasonic diagnostic system of the present invention and the third ultrasonic diagnostic system of the present invention, similar to the first ultrasonic diagnostic system of the present invention, for example, the display means recited in the above items (15) and (25) are used to display the outline. In addition, the display means recited in the above items (17) and (27) are used to display the induced quantity, which is evaluated by the induced quantity calculating means recited in the above items (16) and (26), for example, an area of an inside of the outline, a position of the center of gravity of the outline and a volume of the inside of the outline, or variable quantity over a plurality of frames of the induced quantity.

Incidentally, a technique of calculating a volume of the inside of the outline is not restricted to the specified one. For example, it is acceptable that the outline is approximated by a circle or an ellipse, and volume of the sphere or the ellipsoidal body of revolution, which will be formed through rotation of the sphere or the ellipse, is evaluated. Alternatively, it is also acceptable that the outline is approximated by a plurality of cuboid lamination layers, and the sum of volumes of the circular disks, which will be formed through rotation the cubes, is evaluated.

BRIEF DESCRIPTION OF THE DRAWINGS

FIGS. 13(A), 13(B) and 13(C) are each an explanatory view for an operation for an angle difference;

FIG. 16 is an arithmetic block diagram for evaluation of a distance r and coordinates (Xr, Yr) of an intersection;

FIG. 17 is an arithmetic block diagram for evaluation of a distance dr;

DESCRIPTION OF THE PREFERRED EMBODIMENTS

Hereinafter, there will be described embodiments of the present invention.

First, the first ultrasonic diagnostic system according to an embodiment of the present invention will be described. Since the basic structure of the ultrasonic diagnostic system is well known, there will be omitted redundant description and illustration as to the basic structure itself of the ultrasonic diagnostic system.

Figure 1:
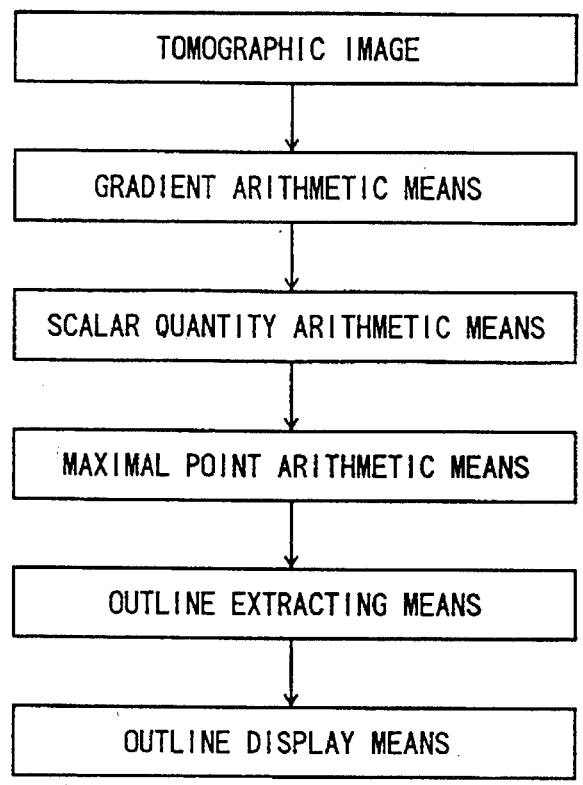
FIG. 1 is a flowchart, in which an outline is extracted and displayed, useful for understanding the first ultrasonic diagnostic system according to an embodiment of the present invention.
Figure 2:
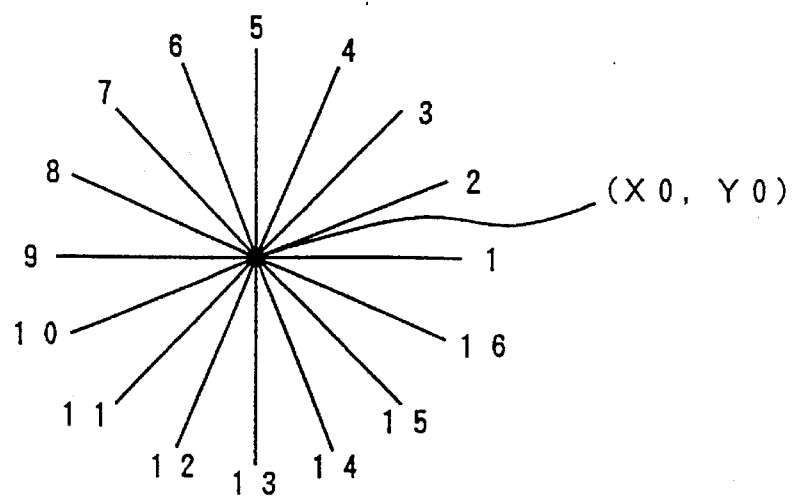
FIG. 2 is a view showing a plurality of assigned lines (e.g. 16 lines) radially extending from a predetermined central point (XO, YO)

FIG. 1 is a flowchart, in which an outline is extracted and displayed, useful for understanding the first ultrasonic diagnostic system according to an embodiment of the present invention. FIG. 2 is a view showing a plurality of assigned lines (e.g. 16 lines) radially extending from a predetermined central point (XO, YO).

First, ultrasonic waves are transmitted to the inside of the subject and the ultrasonic waves reflected within the subject are received, thereby obtaining image data representative of a tomographic image of the inside of the subject. Hereinafter, the image data may be referred to as the image or the tomographic image, without a particular distinction between the image data and the image.

Next, the tomographic image stored in an image memory of the ultrasonic diagnostic system is read with respect to both the horizontal direction and the vertical direction of a field and then subjected to the processing by a differential filter, so that components x and y of the gradient are obtained. This processing is implemented by a gradient arithmetic means.

When the gradient is evaluated, it is desired that the width of the differential filter is between T/2 and 2T (T is thickness of the myocardium). If the width of the differential filter is less than T/2, a weak boundary cannot be emphasized, and it causes snatches of image when magnitude of the gradient is displayed. On the other hand, if the width of the differential filter is more than 2T, magnitude of the gradient near the outline is slow in variation, and it causes the peak to be smoothed. As a result, it would be difficult for both the cases to specify the boundary.

Next, a scalar quantity (magnitude of the gradient) is evaluated by scalar quantity arithmetic means. As magnitude of the gradient, there are considered the sum of the square of the x-component and the square of the y-component of the gradient, namely, the absolute value of the gradient, the square root of such a sum, namely, the absolute value of the gradient, or the sum of the absolute values of the x-component and the y-component.

Next, as shown in FIG. 2, performed is a radial scan from the manually entered central point (XO, YO) or the beforehand designated central point (XO, YO) along the respective assigned lines. A maximal point of magnitude of the gradient is detected through evaluating the difference of magnitude of the gradient on each of the assigned lines. This processing is implemented by a maximal point arithmetic means. The maximal point denotes a point at which a sign of the difference changes from plus to minus. A slow variation of magnitude of the gradient permits a plurality of maximal points to be extracted on a mountain. When a sign of the difference changed, the data of concern is replaced by the average value of the data before and after the data of concern, and the sign is confirmed once more. In this manner, it is possible to select a typical maximal point. The details will be described later.

It is usual that there are found a plurality of maximal points on a line, which are extracted in accordance with the above-mentioned method. Consequently, it is necessary to select an optimum one as a point on the outline. An outline extracting means performs arithmetic on each maximal point as to several characteristic quantities, performs arithmetic as to the general characteristic quantity for each maximal point through synthesizing all the characteristic quantities, and extracts a point on the outline (contour point) from among the maximal points in accordance with the general characteristic quantity. As to the characteristic quantity, the details will be described later.

In this manner, the contour points can be determined. Those contour points are linked together by a straight line or a curved line so as to form an outline. The thus obtained outline is displayed by an outline display means.

There are considered in several ways means for determining an area from the above-mentioned contour points, the straight line, the curved line, the outline and the like. For example, there is considered a method of determining the area by means of calculating the sum of areas of triangles each formed through linking the adjacent two contour points and the central point together.

Now, the respective means mentioned above will be described in detail hereinafter.

Figure 3A:
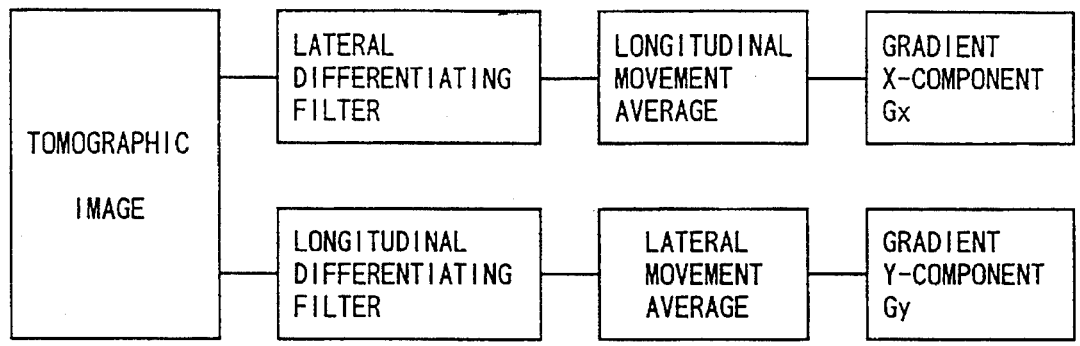
FIGS. 3(A) and 3(B) are each a view showing an example of gradient arithmetic means.
Figure 3B:
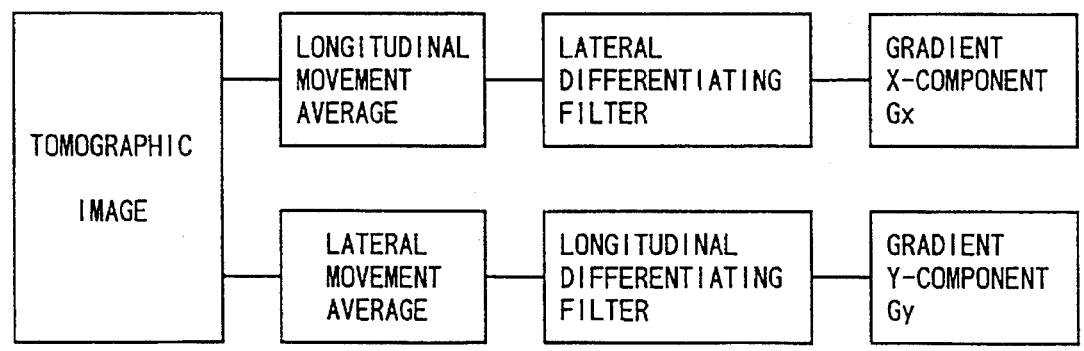

FIGS. 3(A) and 3(B) are each a view showing an example of gradient arithmetic means. FIGS. 4(A)–4(D) are views useful for understanding differentiating filters.

Figures 4A, 4B, 4C, 4D:
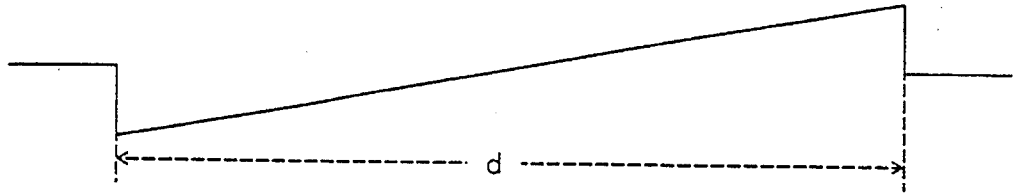
FIGS. 4(A)–4(D) are views useful for understanding differentiating filters.

FIG. 4(A) shows the operators of a one-dimensional differentiating filter in a lateral direction (X-direction). FIG. 4(B) illustrates graphically the differentiating filter. Applying to the tomographic image the differential operators having a certain inclination over the width d as illustrated permits an image to be obtained, which image is involved in the differentiation of the tomographic image in the lateral direction (X-direction).

In the gradient arithmetic means shown in FIG. 3(A), the lateral differentiating filter having the configuration shown in FIGS. 4(A) and 4(B) and the longitudinal differentiating filter having the configuration obtained through rotating by 90° the lateral differentiating filter are used to differentiate the tomographic image in its entirety on a lateral and longitudinal basis. Among the images obtained through the differentiation, the images involved in the differentiation in the lateral direction (X-direction) are subjected to the moving average in the longitudinal direction (Y-direction), and the images involved in the differentiation in the longitudinal direction (Y-direction) are subjected to the moving average in the lateral direction (X-direction).

The reason why the moving average process is applied is as follows. The differentiating process alone may induce a great variation in differential value owing to the noise or the like included in the tomographic image. The moving average process serves to suppress such a variation. Through the operation as mentioned above, it is possible to evaluate the X-component $G_x$ and the Y-component $G_y$ of the gradient of the respective points of the tomographic image.

The gradient arithmetic means shown in FIG. 3(B) performs first the moving average process and then performs the differentiation operation. It is acceptable to reverse the sequence of the moving average process and the differentiation operation.

FIGS. 4(C) and 4(D) show differential operators in which the differentiation in the X-direction is performed, whereas the equalizing operation in the Y-direction is performed, and differential operators in which the differentiation in the Y-direction is performed, whereas the equalizing operation in the X-direction is performed, respectively.

Instead of the separate performance of the differential operation and the moving average process, it is acceptable to apply these differential equalizing operators to the tomographic image.

Figure 5A:
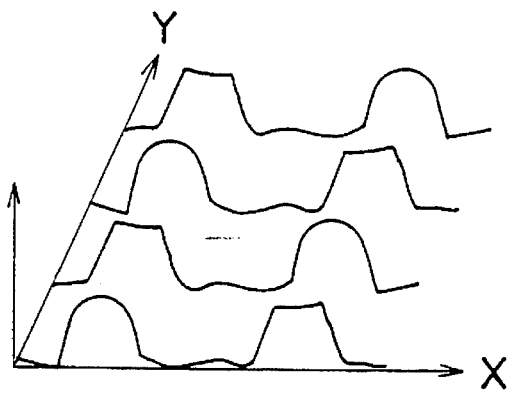
FIGS. 5(A)–5(D) are each a typical illustration in which values of image data of the respective points (X, Y) on tomographic images are graphically illustrated.
Figure 5B:
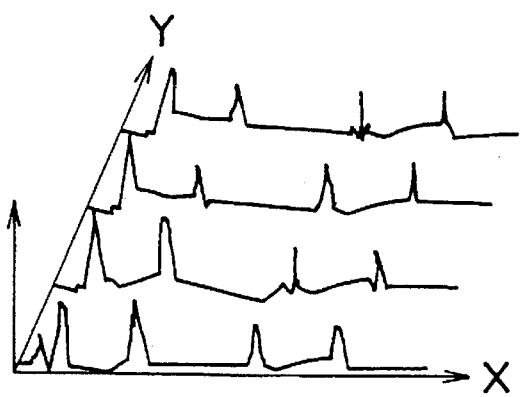
Figure 5C:
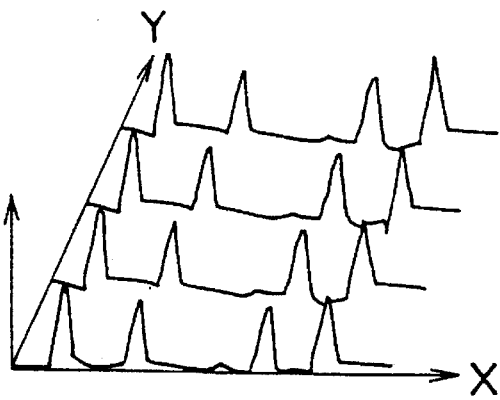
Figure 5D:
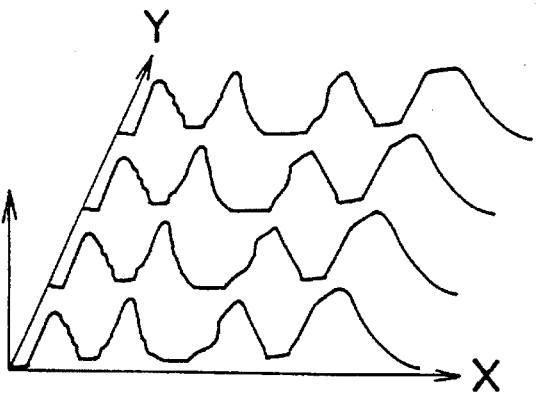

FIGS. 5(A)–5(D) are each a typical illustration in which values of image data of the respective points (X, Y) on tomographic images are graphically illustrated. FIG. 5(A) shows image data before the differential operation, and FIGS. 5(B)–5(D) show each image data after the differential operation.

Let us consider such a case that image data varying in value in the X-direction, as shown in FIG. 5(A), is differentiated. In this case, if the width d of the differentiating filter shown in FIG. 4(B) is too narrow, as shown in FIG. 5(B), only the small value of differential data can be obtained on the points wherein image data of the outline involved in the left ventricle and the myocardium slowly vary. On the other hand, if the width d is too wide, the differential peaks would be vague as shown in FIG. 5(D). According to the experiments by the applicants, it has become clear that the suitable differential data as shown in FIG. 5(C) are obtained when the width d of the differentiating filter is selected to be between 0.5 times and twice as long as the width of the myocardium which is narrower in width than the left ventricle adjacent to the myocardium across the outline to be determined.

According to the present embodiment, by way of example, an image of 640×480 dots, 8 bits per dot (256 gradations), as the tomographic image, is taken in, and the width (2n+1 dots) of the differential data shown in FIGS. 4(A)–4(D) is given by 21 dots which is substantially the same as the thickness of the myocardium. As shown in FIGS. 4(C) and 4(D), according to the present embodiment, the width of the moving average is also given by 2n+1=21 dots.

Figure 6A:
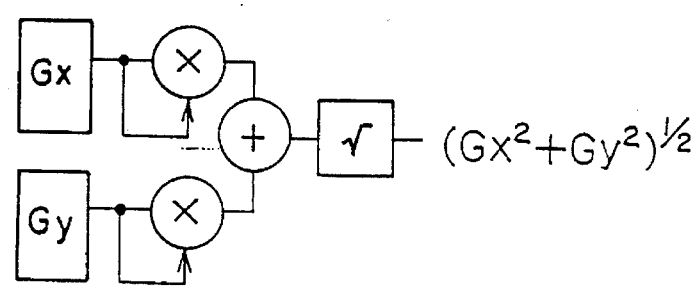
FIGS. 6(A)–6(C) are each a view showing an example of scalar quantity arithmetic means.
Figure 6B:
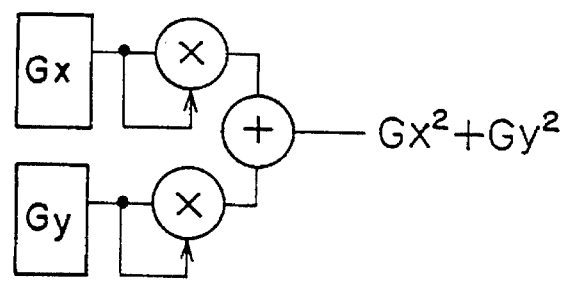
Figure 6C:
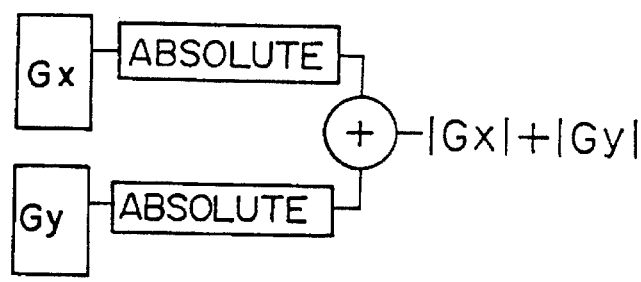

FIGS. 6(A)–6(C) are each a view showing an example of scalar quantity arithmetic means.

According to the example shown in FIG. 6(A), the X-component $G_x$ and the Y-component $G_y$ of the gradient are squared, respectively, so that $G_x^2$ and $G_y^2$ are calculated, and they are added and further the square root of the sum is calculated. That is, the absolute value $(G_x^2+G_y^2)^{1/2}$ of the gradient is calculated.

According to the example shown in FIG. 6(B), comparing with the example shown in FIG. 6(A), the operation of the square root is omitted. That is, the square of the gradient, namely, $G_x^2+G_y^2$ is calculated.

Further, according to the example shown in FIG. 6(C), the absolute values $|G_x|$ and $|G_y|$ of the X-component $G_x$ and the Y-component $G_y$ of the gradient are calculated, respectively, and they are added. That is, $|G_x|+|G_y|$ is calculated.

As will be seen from the examples, it is possible to adopt, as the scalar quantity referred to in the present invention, the various operational quantities corresponding to the magnitude of the gradient.

Figure 7:
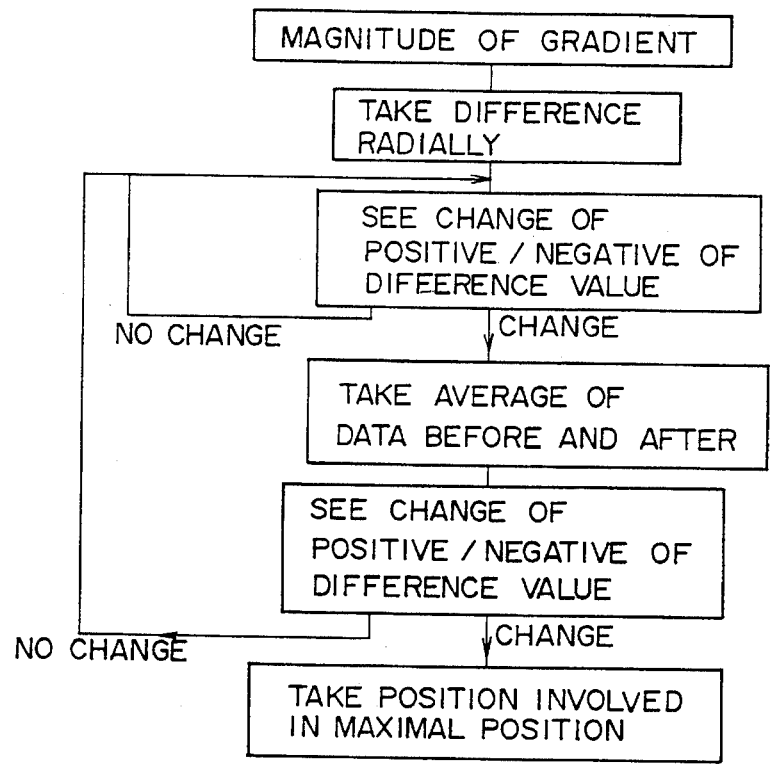
FIG. 7 is a flowchart useful for understanding data processing in maximal point arithmetic means.
Figure 8:
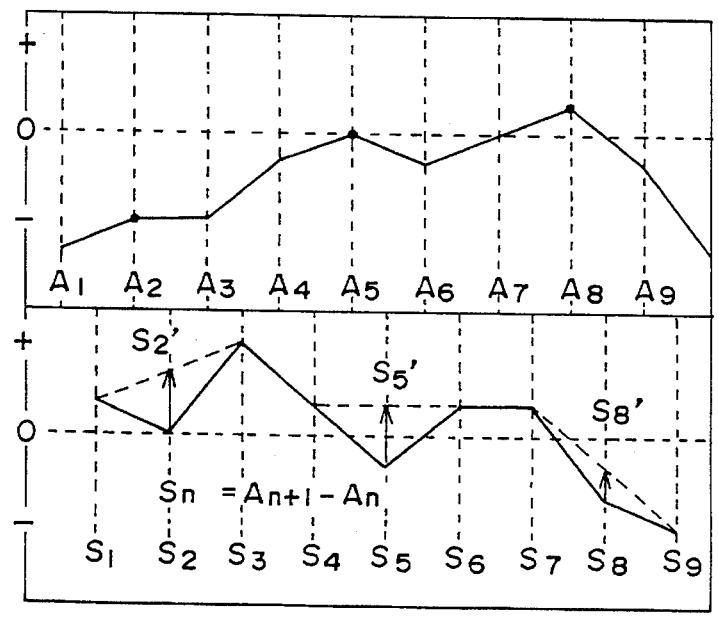
FIG. 8 is an explanatory view for the data processing shown in FIG. 7 with the flowchart.

FIG. 7 is a flowchart useful for understanding data processing in maximal point arithmetic means. FIG. 8 is an explanatory view for the data processing shown in FIG. 7.

In the maximal point arithmetic means, first, making reference to the magnitude of the gradient calculated in the scalar quantity arithmetic means, the difference is evaluated radially along the respective assigned lines, and looking the change of the positive and negative of the evaluated difference value, detected is a position at which the magnitude of the gradient becomes maximal, in other wards, a position at which the sign of the difference of the magnitude of the gradient changes from the positive to the negative, thereby detecting a candidate point of the maximal point which is deemed to be on the outline of the left ventricle. However, if the magnitude of the gradient varies, this involves such a problem that even the point, which is not apparently involved in the outline, will be selected as the candidate point. In order to avoid this drawback, the extraction of the candidate point is performed in such a manner that when the difference value of magnitude of the gradient changed from the positive to the negative, the candidate point extracted owing to such a change is replaced by the average value of the difference value of magnitude of the gradient as to the points before and after the point of concern in the form of the new difference value, and then the determination as to the positive and negative is performed again, and as a result, only when the change of the sign is detected again, it is extracted as the candidate point.

For example, in FIG. 8, $A_n$ denotes magnitude of the gradient; and $S_n=A_{n+1}-A_n$ the difference of magnitude of the gradient. $A_5$ is temporarily extracted as the candidate of the maximal point, since $S_4$ and $S_5$ are different in sign from each other. However, if $S_5$ is replaced by $S_5'=(S_4+S_6)/2$, then $S_4$ and $S_5'$ are the same in sign. Thus, this candidate point is not extracted as the maximal point. On the other hand, with respect to $A_8$, $S_7$ and $S_8$ are different in sign from each other. Further, even if $S_8$ is replaced by $S_8'=(S_7+S_9)/2$, $S_7$ and $S_8'$ are different in sign from each other. Thus, $S_8$ is extracted as the maximal point.

Figure 9:
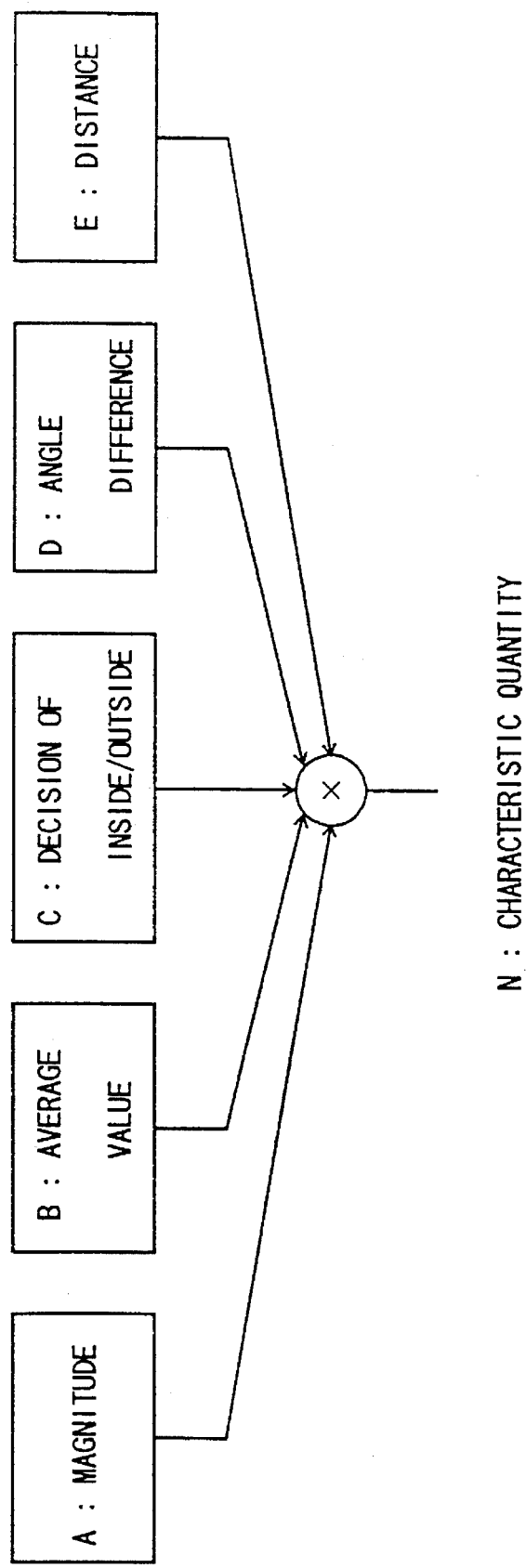
FIG. 9 is a view showing various kinds of characteristic quantity which are evaluated by outline extraction means.

FIG. 9 is a view showing various kinds of characteristic quantity which are evaluated by outline extraction means.

In the outline extracting means, when the outline of the left ventricle is extracted, 5 characteristic quantities of "A: magnitude", "B: average", "C: inside/outside determination", "D: angle difference" and "D: distance", as shown in FIG. 9, are determined and they are multiplied by each other so that the general characteristic quantity is calculated with respect to the respective maximal points.

The characteristic quantity "A: magnitude" denotes magnitude of the gradient. Here, for example, there is adopted the square of the absolute value of the gradient: $G_x^2+G_y^2$, which is operated in accordance with the operators shown in FIG. 6(B).

Figure 10A:
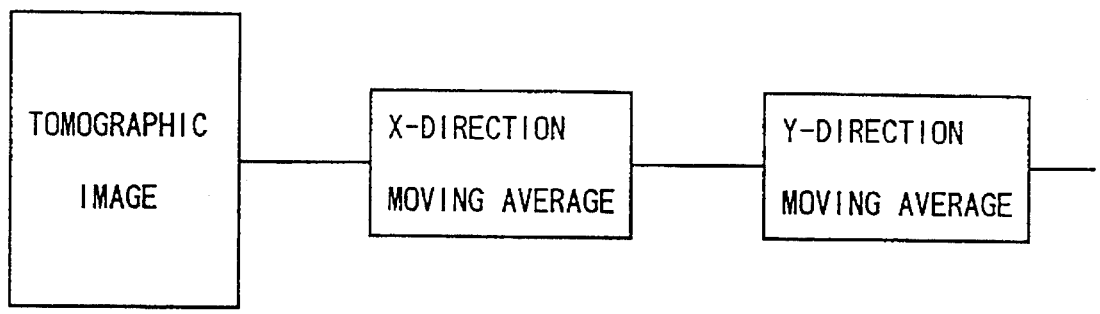
FIGS. 10(A) and 10(B) are each an arithmetic block diagram for calculating an average.
Figure 10B:
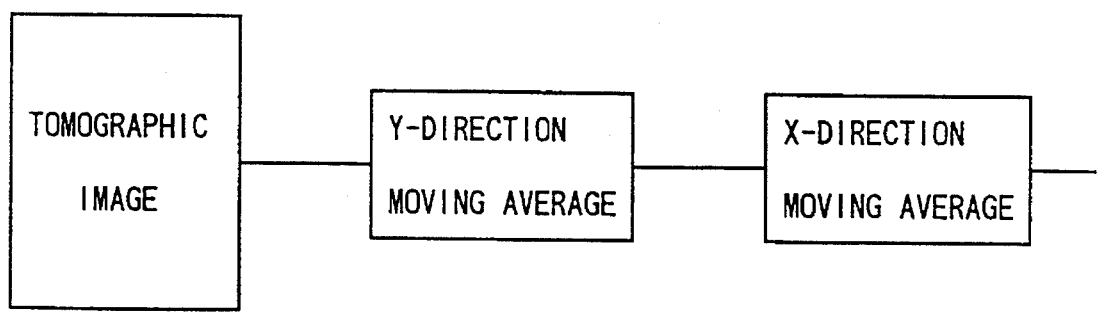

FIGS. 10(A) and 10(B) are each an arithmetic block diagram for calculating the characteristic quantity "B: average".

Image data of the tomographic image are subjected to the moving average process as to the corresponding 21 dots, which is equivalent to the width d of the differentiating filter (cf. FIG. 4(B)), with respect to both the X-direction and the Y-direction. Regarding the order of the moving average process, it is acceptable that as shown in FIG. 10(A), the moving average process is performed first with respect to the X-direction, alternatively, as shown in FIG. 10(B), first with respect to the Y-direction.

That is, with respect to the respective pixels, as shown in the equation (10) set forth below, ±10 dots in the X-direction around the pixels of interest and ±10 dots in the Y-direction around the pixels of interest of image data are added.

$$B = \sum_{x=1}^{10} \sum_{y=1}^{10} \text{(image signal)} \tag{10}$$

Incidentally, to obtain the average, it is needed mathematically to divide the above equation by the number of pixels. However, since the number of pixels as an object of operation is fixed, it may be considered that the added value is equivalent to the average on a data processing basis. Thus, in the present embodiment, the division by the number of pixels is omitted for the purpose of reduction of an amount of calculation.

Figure 11A:
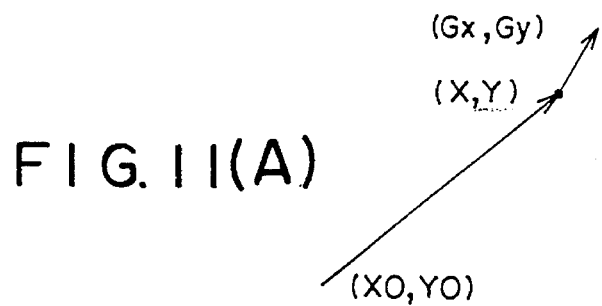
FIGS. 11(A) and 11(B) are each an explanatory view for an operation for determination of the inside and outside.
Figure 11B:
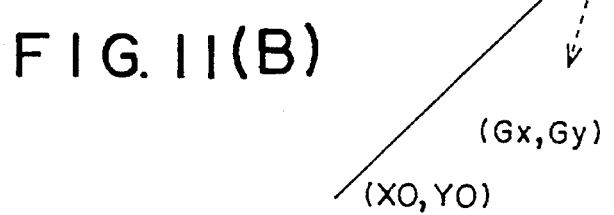

FIGS. 11(A) and 11(B) are each an explanatory view for an operation of the characteristic quantity "C: inside/outside determination".

Determination as to whether the gradient vector is directed inside or outside looking from the central point (X0, Y0) (cf. FIG. 2) is performed according as the inner product (scalar product) of the gradient vector ($G_x$, $G_y$) of the maximal point and the direction vector (X-X0, Y-Y0) toward the position (X, Y) of the maximal point from the central point (X0, Y0) is of the positive or negative.

$$\text{(inner product)} = (X-X0) \cdot G_x + (Y-Y0) \cdot G_y \tag{11}$$

Now, the inner product given by the equation (11) is calculated. If (inner product) >0, the gradient vector is directed outside as shown in FIG. 11(A), and thus the characteristic quantity C=1. On the other hand, if (inner product) $\geq 0$, the gradient vector is directed inside as shown in FIG. 11(B), and thus the characteristic quantity C=0.

Finally, in order to determine the general characteristic quantity, all the individual characteristic quantities are multiplied by each other. Thus, the points having the gradient vectors directed inside are omitted. This is intended to extract as the outline only the inner wall of the left ventricle end of the myocardium, but not to extract as the outline the outer wall of the myocardium.

Figure 12:
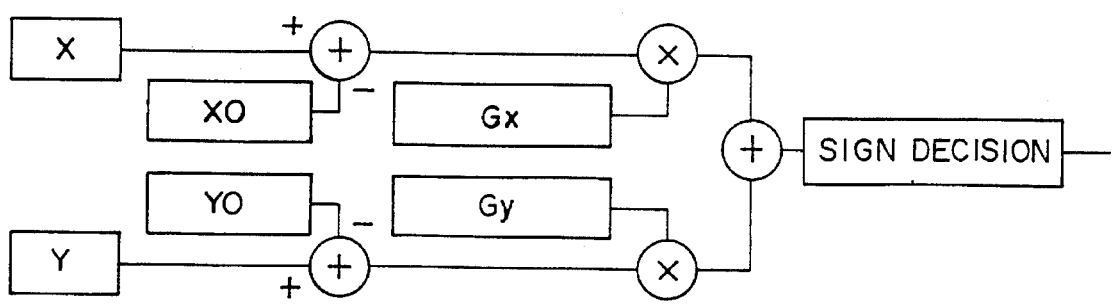
FIG. 12 is an arithmetic block diagram for determination of the inside and outside.

FIG. 12 is an arithmetic block diagram for determination of the characteristic quantity C.

The difference (X-X0, Y-Y0) of coordinates (X, Y) of the maximal point and coordinates (X0, Y0) of the center is evaluated. The X-component X-X0 and the Y-component Y-Y0 are multiplied by the X-component $G_x$ of the gradient and the Y-component $G_y$, respectively, and the multiplication results are added. And the sign of the added value is determined. As a result, if the sign is plus, C=1 is outputted since the gradient is directed to outside, whereas if the sign is minus, C=0 is outputted since the gradient is directed to inside.

FIGS. 13(A), 13(B) and 13(C) are each an explanatory view for an operation for the characteristic quantity "D: angle difference".

Assuming that the operation is performed sequentially with respect to a plurality of assigned lines radially extended as shown in FIG. 2, as shown in FIG. 13(A), there will be evaluated the angle dθ formed with the gradient vector $G1=(G_{x1}, G_{y1})$ of the contour point on the preceding assigned line and the gradient vector $G2=(G_{x2}, G_{y2})$ of the respective maximal points #1 to #5 on the current assigned line. Since it is considered that the directions of the ridge lines of adjacent two points on the contour line are approximately the same as each other, the characteristic quantity D will increase in output with smaller angle difference dθ is smaller.

Assuming that angles of the gradients are given by θ1 and θ2, respectively, as shown in FIG. 13 (B), the associated gradient vectors are respectively expressed by:

$$G1=|G1|\exp(j\theta1)$$

$$G2=|G2|\exp(j\theta2)$$

where j denotes imaginary unit

Multiplying G2 by complex conjugate of G1, $$\begin{aligned} G1^* \cdot G2 &= |G1|\exp(-j\theta1) \times |G2|\exp(j\theta2) \\ &= |G1||G2|\exp(j(\theta2-\theta1)) \end{aligned}$$

Hence, $$d\theta = \theta2 - \theta1 = a\tan \frac{\text{Imag}(G1^* \cdot G2)}{\text{Real}(G1^* \cdot G2)} \tag{12}$$

where * denotes complex conjugate

On the other hand, the gradient vectors are expressed by:

$$G1=Gx1+jGy1$$

$$G2=Gx2+jGy2$$

Hence, $$\begin{aligned} G1^* \cdot G2 &= (Gx1-jGy1)(Gx2+jGy2) \\ &= Gx1 \cdot Gx2 + Gy1 \cdot Gy2 + \\ &\quad j(Gx1 \cdot Gy2 - Gx2 \cdot Gy1) \end{aligned}$$

Real part and imaginary part of the $G1^* \cdot G2$ are respectively expressed by:

$$\text{Real }(G1^* \cdot G2) = Gx1 \cdot Gx2 + Gy1 \cdot Gy2$$

$$\text{Imag }(G1^* \cdot G2) = Gx1 \cdot Gy2 - Gx2 \cdot Gy1$$

The angle dθ to be evaluated is:

$$d\theta = a\tan \frac{Gx1 + Gy1 - Gx1 \times Gy2}{Gx1 + Gx2 + Gy1 \times Gy2} \tag{13}$$

The characteristic quantity D is defined by the following equation in such a manner that as shown in FIG. 13(C) when the angle difference dθ is 0, it takes the maximum value π, and it approaches 0 according as the angle difference dθ approaches π or −π.

$$D=\pi-|d\theta| \tag{14}$$

Figure 14:
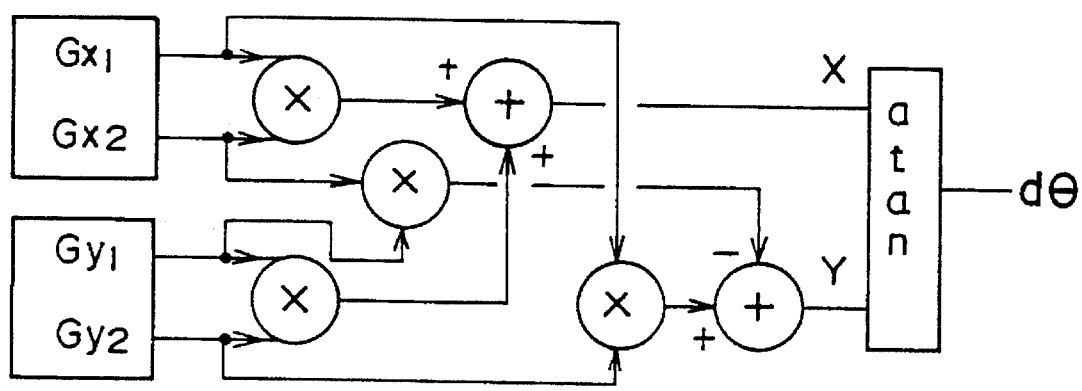
FIG. 14 is an arithmetic block diagram for evaluation of an angle difference.

FIG. 14 is an arithmetic block diagram for evaluation of the characteristic quantity D.

$$X=Gx1 \times Gx2+Gy1 \times Gy2$$

$$Y=Gx1 \times Gy2-Gx2 \times Gy2$$

Arithmetic on the above equations is performed, and then, $$d\theta = a\tan(Y/X)$$

arithmetic on the above equation is performed, so that the angle difference dθ is evaluated according to the equation (13).

Figure 15A:
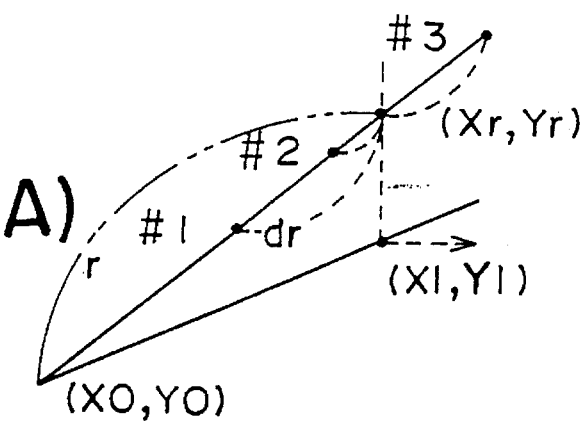
FIGS. 15(A), 15(B) and 15(C) are each an explanatory view for an operation for a distance.
Figure 15B:
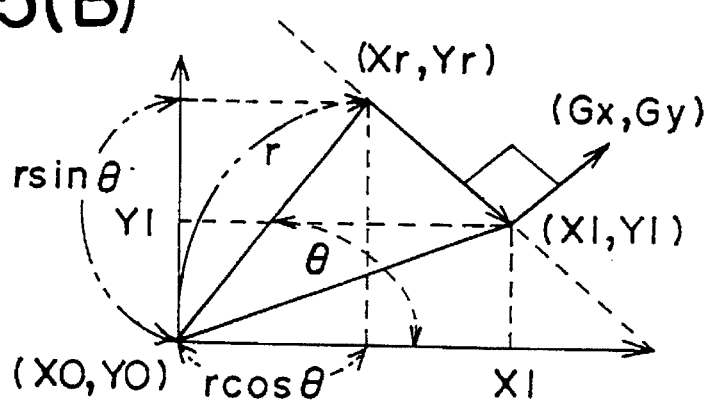
Figure 15C:
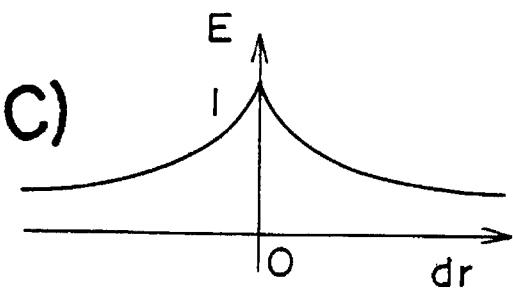

FIGS. 15(A), 15(B) and 15(C) are each an explanatory view for an operation of the characteristic quantity "E: for distance".

As shown in FIG. 15(A), we find the distance dr from the intersection (Xr, Yr) of the line extended from the position (X1, Y1) of the contour point on the preceding assigned line perpendicularly to the gradient of the associated contour point and the current assigned line, up to the position of each the maximal point on the current assigned line. And the characteristic quantity E increases in output with shorter distance dr. For instance, in case of FIG. 15(A), the distance dr of the maximal point #2 is shortest. Hence, the characteristic quantity E on the maximal point #2 assumes the largest value.

First, we find the standard length, that is, the distance between the central point (X0, Y0) and the intersection (Xr, Yr).

In FIG. 15(B), (X0, Y0) denotes the central point of the radial segment; (X1, Y1) a contour point of the preceding assigned line; (Gx, Gy) a gradient vector of the contour point; (Xr, Yr) the intersection of the current assigned line and the straight line passing through the contour point on the preceding assigned line and lying perpendicular to the gradient of the associated contour point; and θ an angle of the current assigned line when the X-axis is selected as the base.

The ratio of the X-component and the Y-component of the vector of thick line directed from (Xr, Yr) to (X1, Y1) is expressed by the following equation:

$$R = \frac{Gy}{-Gx} = \frac{(X1-X0) - r\cos\theta}{(Y1-Y0) - r\sin\theta}$$

This expression may be modified as follows:

$$-Gx(X1 - X0 - r\cos\theta) = Gy(Y1 - Y0 - r\sin\theta)$$
$$r(Gx\cos\theta - Gy\sin\theta) = Gx(X1 - X0) + Gy(Y1 - Y0)$$

Hence, $$r = \frac{Gx(X1-X0) + Gy(Y1-Y0)}{Gx\cos\theta - Gy\sin\theta} \quad (15)$$

The coordinates (Xr, Yr) of the intersection as the basis is expressed by $$Xr = X0 + r\cos\theta, \quad Yr = Y0 + r\sin\theta \quad (16)$$

In the determination of the distance dr from this coordinates on each maximal point (X, Y), $$dr = \{(X-Xr)^2 + (Y-Yr)^2\}^{1/2} \quad (17)$$

In this case, it is deemed that a #2 of candidate point is the nearest point.

The characteristic quantity E is given by such an exponential function that as the distance extends a predetermined dot number dr0 (e.g. dr0=20 dots), the output decreases half as shown in FIG. 15(C). That is, the characteristic quantity E is expressed by $$E = \exp\left(\frac{-dr \cdot \log 2}{dr0}\right) \quad (18)$$

FIG. 16 is an arithmetic block diagram for evaluation of a distance r and coordinates (Xr, Yr) of an intersection. FIG. 17 is an arithmetic block diagram for evaluation of a distance dr.

As shown in FIG. 16, the coordinates (X0, Y0) of the central point, the coordinates (X1, Y1) of a contour point on the preceding assigned line, the gradient (Gx, Gy) of the contour point, and the angle θ of the current assigned line are inputted.

$$A = Gx(X1-X0) + Gy(Y1-Y0)$$

$$B = Gx\cos\theta - Gy\sin\theta$$

Arithmetic on the above equations is performed, and then, $$r = A/B$$

arithmetic on the above equation is performed, so that the distance r is determined according to the expression.

Further, the distance r is multiplied by cos θ and sin θ, respectively, and then X0 and Y0 are added, respectively. Thus, as shown in expression (16), the following is evaluated.

$$Xr = X0 + r\cos\theta$$

$$Yr = Y0 + r\sin\theta$$

Next, as shown in FIG. 17, the coordinates (Xr, Yr) of an intersection determined in the manner as mentioned above and the coordinates (X, Y) of the maximal point on the current assigned line are inputted, so that the following shown in the expression (17) is determined.

$$dr = \{(X-Xr)^2 + (Y-Yr)^2\}^{1/2}$$

The distance dr is transformed in accordance with the expression (18) to find the characteristic quantity E.

All the characteristic quantities A–E determined in the manner as mentioned above are multiplied by each other so that the general characteristic quantity N is calculated for each maximal point. Incidentally, when the general characteristic quantity N is calculated, it is acceptable to omit any of the characteristic quantities A–E, or to add another characteristic quantity.

Figure 18:
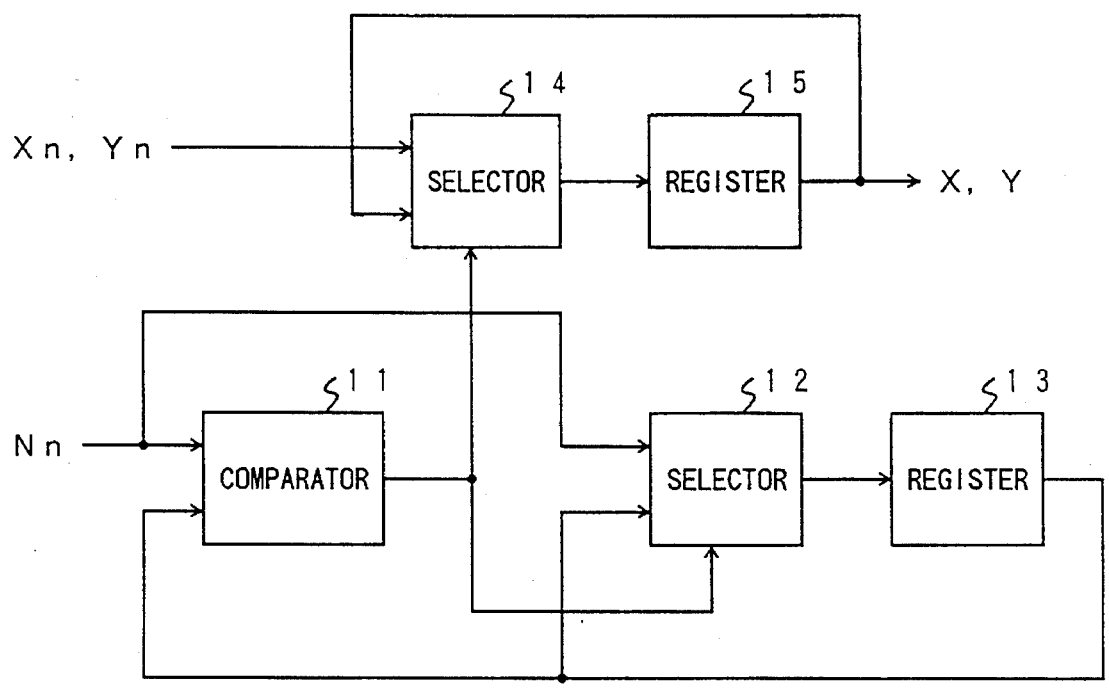
FIG. 18 is a circuit block diagram for extracting a contour point for each assigned line on the basis of the calculated characteristic quantity N.

FIG. 18 is a circuit block diagram for extracting a contour point for each assigned line on the basis of the general characteristic quantity N calculated in the manner as mentioned above.

In FIG. 18, n denotes the number applied to the maximal point for each assigned line.

With respect to a certain assigned line, the coordinates (Xn, Yn) of the maximal point and the characteristic quantity Nn of the associated maximal point are sequentially inputted. The characteristic quantity Nn is inputted to both a comparator 11 and a selector 12. The comparator 11 and the selector 12 receive also the value stored in a register 13. The comparator 11 compares the characteristic quantity Nn with the value supplied from the register 13. The comparison result is supplied to the selector 12 in the form of a control signal. The selector 12 permits the passage of larger one of the two values which are compared in the comparator 11. An output of the selector 12 is stored in the register 13.

The coordinates (Xn, Yn) of the maximal point is applied to a selector 14 which receives also the coordinate value stored in a register 15. The content of the register 15 is updated to the current coordinates (Xn, Yn), or the preceding content of the register 15 is maintained, in accordance with the comparison result of the comparator 11.

In this manner, when the sequential entry of the coordinates (Xn, Yn) of the maximal point and the characteristic quantity Nn of the associated maximal point is completed with respect to a certain assigned line, the register 15 stores the coordinates (X, Y) of the maximal point having the maximum characteristic quantity among a plurality of maximal points on the associated assigned line, and the maximal point having the maximum characteristic quantity is extracted as the contour point.

After the maximal point having the maximum characteristic quantity is extracted on a single assigned line in a manner as described above, a distance between the maximal point thus extracted and the contour point, which has been extracted in a similar fashion and has been determined with respect to another assigned line adjacent to the assigned line of interest, is calculated. As a result, if the distance thus calculated is in excess of a predetermined distance, in other words, in a case where though the contour is continuous, the extracted maximal point is away in excess of a distance which may be regarded as a continuity with respect to the contour point on the adjacent assigned line, it is stopped to adopt the extracted maximal point as the contour point, and the extraction as to the maximal point is performed again in a similar fashion to that mentioned above. It is acceptable to extract the maximal point within a predetermined distance as the contour point through repeatedly performing the above-mentioned process in accordance with the necessity. This arrangement permits the contour to be extracted with greater accuracy.

Incidentally, to determine the contour point on the first assigned line, in a case where the maximal point having the characteristic quantity of which the value is extremely large in comparison with the other maximal points is present on the first assigned line, it is acceptable that such a maximal point is decided as the contour point, and thereafter the contour points on the adjacent assigned lines are sequentially determined in accordance with the above-mentioned technique. Alternatively, it is acceptable that with respect to the first assigned line, the maximal point involved in the maximum characteristic quantity is displayed on the display so that an operator judges whether such a maximal point is present on the outline, and if it is judged that such the maximal point is not present on the outline, the sequence to display on the display the maximal point involved in the next large characteristic quantity is repeated to determine the contour point on the first assigned line. It is also acceptable with respect to the contour point on the first assigned line that an operator designates the contour point without performing arithmetic on the characteristic quantity as described above.

Next, dealing with a plurality of frames each indicative of the same tomographic surface at the different time, the following process is applied. After the contour point as to a certain frame (the preceding frame) is decided, the characteristic quantities on the respective maximal points are evaluated as to the subsequent frame (the current frame) in the manner as described above, the maximal point having the maximum characteristic quantity on each assigned line is evaluated, and a distance between the contour point on the preceding frame already decided and the maximal point having the maximum characteristic quantity evaluated as to the current frame, which are involved in the same assigned line when the preceding and current frames are overlapped, is evaluated. The maximal point having the maximum characteristic quantity is decided as the contour point according as the distance thus evaluated is within a predetermined distance or not. Alternatively, it is acceptable that the sequence to omit the maximal point having the maximum characteristic quantity and evaluate the maximal point having the next large characteristic quantity on the associated assigned line is repeated. This arrangement also permits the contour to be extracted with greater accuracy. Incidentally, with respect to the technique as to how the contour point of the initial frame is decided, in a similar fashion to that of the above case, it is possible to select a desired one from among the various schemes.

As a result of the fact that the maximal point involved in the larger characteristic quantity is omitted in accordance with the manner as described above, when a suitable maximal point within a predetermined distance cannot be located, it is acceptable to determine the contour point in such a manner that the contour points on the adjacent assigned lines are coupled with a straight line, and the intersection of the straight line and the assigned line on which the maximal point cannot be located is found, so that the intersection is decided as the contour point on the assigned line of interest. Alternatively, it is acceptable to determine the outline on the basis of only the decided contour points on the assumption that no contour point is present on the assigned line of interest.

As one of the causes that the accuracy of extraction of the outline is decreased, there is the presence of valve between the left ventricle and the left atrium. As a technique of preventing the accuracy of extraction of the outline from being decreased owing to the presence of the valve, a method of deciding length of the distance as mentioned above may be used.

Figure 19A:
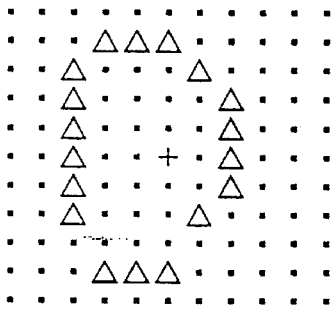
FIGS. 19(A), 19(B) and 19(C) are each an illustration useful for understanding a technique for preventing accuracy of outline extraction from being deteriorated owing to the presence of a valve.
Figure 19B:
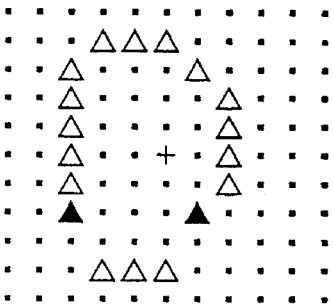
Figure 19C:
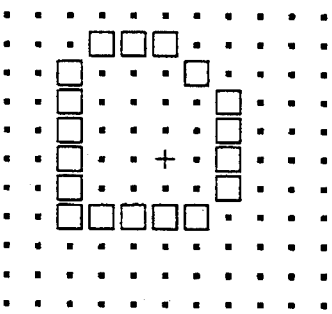

FIGS. 19(A), 19(B) and 19(C) are each an illustration useful for understanding a technique for preventing accuracy of outline extraction from being deteriorated owing to the presence of a valve. In those figures, the mark "+" denotes the central point.

First, assuming that the contour candidate points as shown in FIG. 19(A) are found on the respective assigned lines in accordance with the manner as mentioned above, it is decided whether the distance between the adjacent candidate points is within a predetermined distance. As a result, as shown in FIG. 19(B), the candidate points of both edges corresponding to the sources of two valves are detected, and the candidate points in the domain between the candidate points of both edges are omitted, so that only the candidate points existing in a domain excepting the domain sandwiched is valid. Thus, as shown in FIG. 19(C), according to the present embodiment, the candidate points of both edges are coupled with a straight line to complete the closed curve as the outline.

Thus, it is possible to prevent accuracy of outline extraction from being deteriorated owing to the presence of the valve.

FIGS. 20(A)–20(D) are each an illustration useful for understanding another technique for preventing accuracy of outline extraction from being deteriorated owing to the presence of the valve.

Figure 20A:
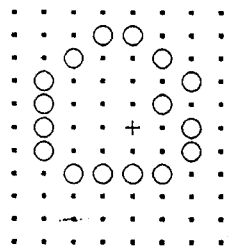
FIGS. 20(A)–20(D) are each an illustration useful for understanding another technique for preventing accuracy of outline extraction from being deteriorated owing to the presence of a valve.
Figure 20B:
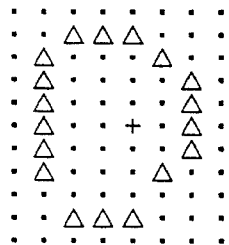
Figure 20C:
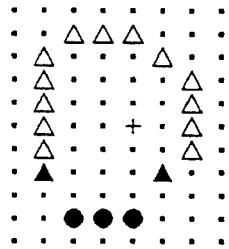
Figure 20D:
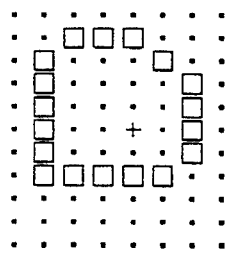

According to this method, a distance between the candidates (FIG. 20(A)) of the preceding frame and the candidates (FIG. 20(B)) of the current frame on the same assigned line is investigated. That is, it is decided whether the distance is within a predetermined distance. As a result, the candidates located away in excess of the predetermined distance are omitted (FIG. 20(C)). In this manner, in a similar fashion to that of FIGS. 19(A), 19(B) and 19(C), it is possible to determine the outline with accuracy.

Figure 21A:
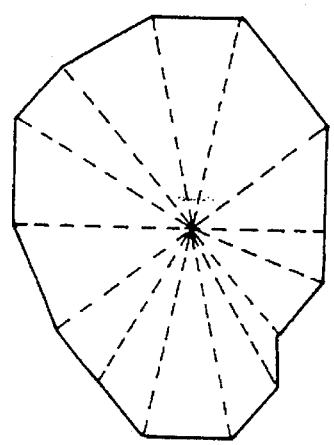
FIGS. 21(A)–21(C) are each an illustration depicting an outline of the left ventricle obtained through coupling the contour points on the respective assigned lines with each other.
Figure 21B:
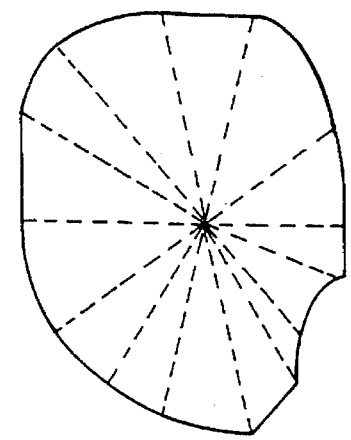
Figure 21C:
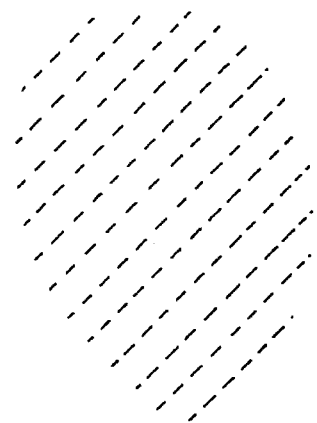

FIGS. 21(A)–21(C) are each an illustration depicting an outline of the left ventricle obtained through coupling the thus determined contour points on the respective assigned lines with each other.

Roughly, as shown in FIG. 21(A), it is acceptable to couple the contour points with straight lines. Alternatively, more exactly, as shown in FIG. 21(B), it is acceptable to smoothly couple the contour points using the spline function.

The outline display means shown in FIG. 1 displays the contours as shown in FIG. 21(A) or FIG. 21(B) superposing on the tomographic image. Alternatively, it is acceptable to perform display drawing a distinction between the inside and outside of the contour by color, luminance or the like, as shown in FIG. 21(C), instead of displaying the contour.

Figure 22A:
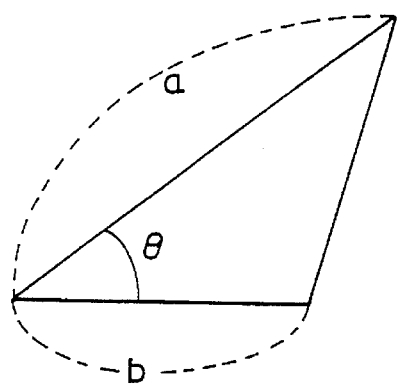
FIGS. 22(A) and 22(B) are each an illustration useful for understanding an example as to how the area of the left ventricle appearing on the tomographic image is evaluated.
Figure 22B:
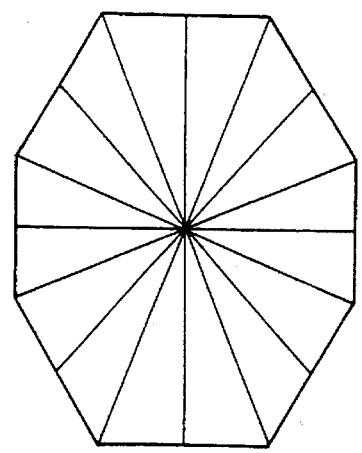

FIGS. 22(A) and 22(B) are each an illustration useful for understanding an example as to how the area of the left ventricle appearing on the tomographic image is evaluated.

Area of a triangle can be determined, as shown in FIG. 22(A), if the length a and b of two sides and the angle therebetween are known. Hence, as shown in FIG. 22(B), adding areas of the triangles once around permits the approximate area of the left ventricle to be evaluated.

While it is acceptable that area of the inside (left ventricle) is evaluated through performing an integral operation on area of the inside surrounded with the contour, it is possible to evaluate area of the left ventricle with great accuracy and at high speed also by the above-mentioned arithmetic method.

Figure 23:
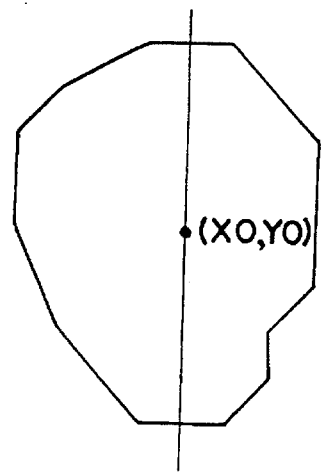
FIG. 23 is an illustration useful for understanding an example as to how the volume of the left ventricle is evaluated.

FIG. 23 is an illustration useful for understanding an example as to how the volume of the left ventricle is evaluated.

After the contour is found in the manner as described above, extracted is two assigned lines each extending to the opposite direction from the central point (X0, Y0) and satisfying such a condition that the sum of distances from the central point (X0, Y0) to the contour points assumes the maximum. And when the contour is rotated on those assigned lines as the axis of rotation, volume of the inside of the solid of revolution is calculated. This is based on a view such that the left ventricle as a whole is approximately elliptical. The volume thus calculated is regarded as the volume of the left ventricle. As a method of calculation of volume, there are known, for example, Teichkolz method, Pombo method, Gibson method and the like. It is acceptable to adopt any of those methods.

Figure 24:
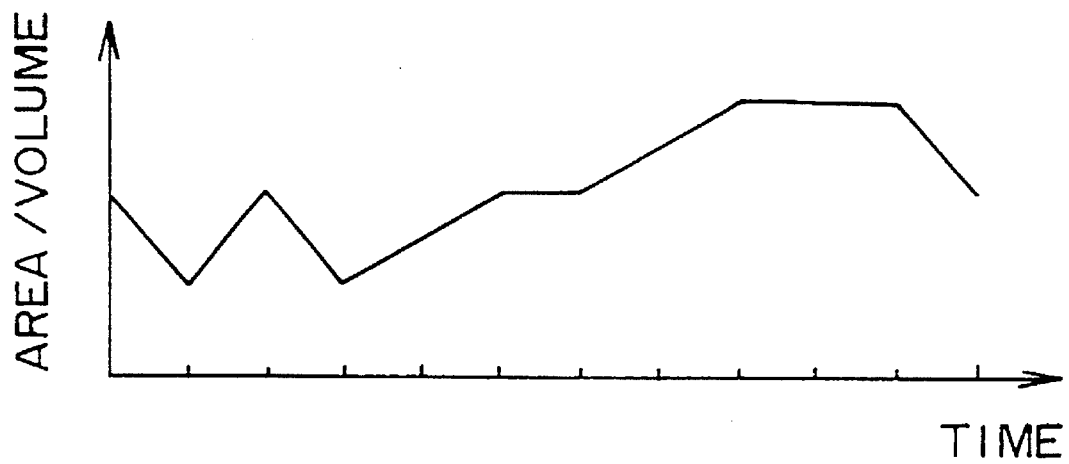
FIG. 24 is an illustration useful for understanding an example as to how the area or the volume is displayed.

FIG. 24 is an illustration useful for understanding an example as to how the area or the volume is displayed.

Tomographic images are sequentially derived at a predetermined frame rate as time passes. Consequently, if area or volume is evaluated on each of the tomographic images and the evaluated area or volume is displayed, as shown in FIG. 24, in the form of function of time, a degree of expansion and contraction of the heart will be apparently grasped. Thus, it is more effective in observation and diagnostic. Of course, it is acceptable to display area or volume in the form of numerical value.

Figure 25A:
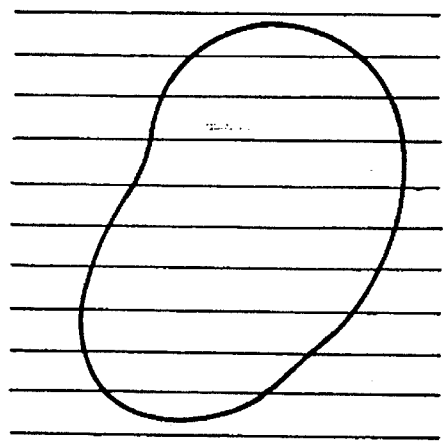
FIGS. 25(A)–25(C) are each an illustration depicting another example of the assigned lines.
Figure 25B:
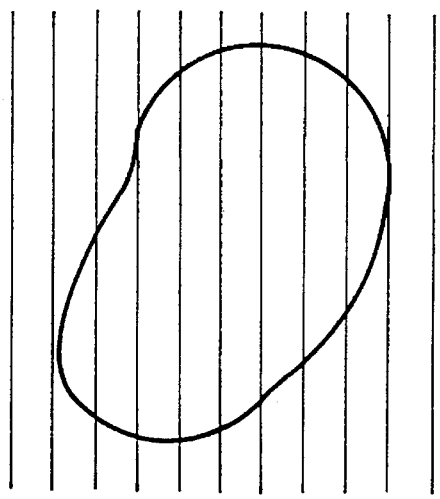
Figure 25C:
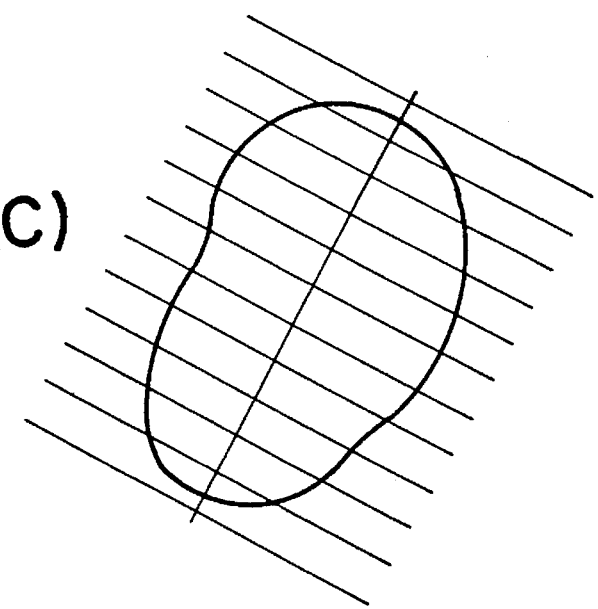

FIGS. 25(A)–25(C) are each an illustration depicting another example of the assigned lines.

According to the embodiments as mentioned above, there are adopted the assigned lines radially extending from the central point (X0, Y0). However, it is not necessarily needed for the present invention to adopt such radial assigned lines. It is acceptable to adopt, for example, the assigned lines extending in parallel to the X-direction as shown in FIG. 25(A), and the assigned lines extending in parallel to the Y-direction as shown in FIG. 25(B).

Adopting the assigned lines parallel to the X-direction or the Y-direction as shown in FIG. 25(A) and as shown in FIG. 25(B) serves to more simplify arithmetic for evaluation of coordinates of the maximal points on the assigned lines in comparison with a case where the radial assigned lines as shown in FIG. 2 is adopted.

Further, it is acceptable to adopt the assigned lines which will be obtained in such a way that an operator designates an approximate major axis on a display field of a tomographic image and the assigned lines are extended in a direction perpendicular to the designated major axis.

In the first ultrasonic diagnostic system according to the present invention, it is not necessarily needed to adopt the assigned lines. It is acceptable to determine the outline in such a manner that the approximate positions of the outline are found with the use of the conventional method or other simple way for example, a lot of small domains are set up on the tomographic image along the approximate outline thus found, maximal points and characteristic quantities within each small domain are evaluated, the maximal point involved in the maximum characteristic quantity is extracted for each small domain, and the maximal points thus extracted are coupled with each other.

Next, there will be explained the embodiment of the second ultrasonic diagnostic system according to the present invention.

Figure 26:
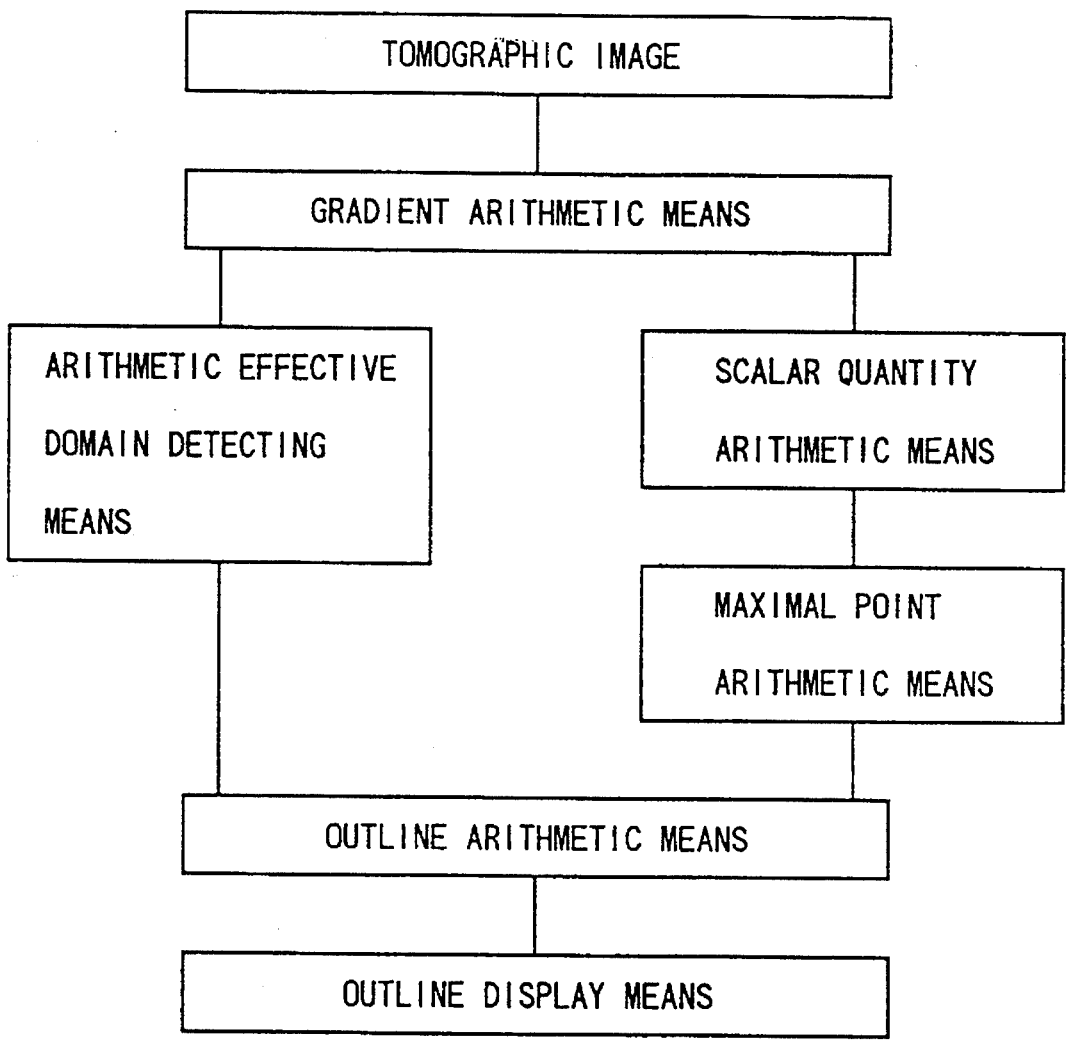
FIG. 26 is a flowchart, in which an outline is extracted and displayed, useful for understanding the second ultrasonic diagnostic system according to an embodiment of the present invention.

FIG. 26 is a flowchart, in which an outline is extracted and displayed, useful for understanding the second ultrasonic diagnostic system according to the embodiment of the present invention.

With respect to the flowchart shown in FIG. 26, the difference between it and that involved in the embodiment of the first ultrasonic diagnostic system shown in FIG. 1 is only the point that arithmetic effective domain detecting means is provided. Thus, the redundant description will be omitted, and the arithmetic effective domain detecting means will be mainly described, hereinafter.

According to the arithmetic effective domain detecting means, in the manner as described referring to FIGS. 11(A)–11(B) and FIG. 12, it is discriminated on the respective pixels over the tomographic image in its entirety whether a direction of the gradient is inward to be directed to a direction approaching the central point (X0, Y0) (FIG. 11(B)) or outward to be directed to a direction being away from the central point (X0, Y0) (FIG. 11(A)). The arithmetic effective domain detecting means produces a binary image on the basis of a discrimination result, so that an arithmetic effective domain is decided on the basis of the binary image.

Figures 27A, 27B, 27C:
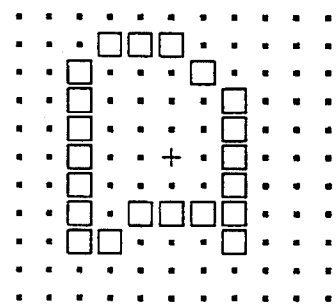
FIGS. 27(A)–27(C) are each an illustration useful for understanding as to how the effective domain for operation is determined.

FIGS. 27(A)–27(C) are each an illustration useful for understanding as to how the effective domain for operation is determined.

FIG. 27(A) is representative of a binary image produced on the basis of the direction of the gradient in the manner as mentioned above. A coupling treatment is performed on the binary image through labelling according to the algorithm set forth below. In the binary image, the mark x denotes the pixel involved in a direction of the gradient being inward.

(1) In applying of a numerical label to a certain pixel, apply the same numerical value of label as the pixel to which the smallest number of label is applied, among pixels having the same value in the adjacent pixels (the same in the direction of the gradient).

(2) When there is no pixel having the same value in the adjacent pixels, or in a case where while there is a pixel having the same value in the adjacent pixels, the adjacent pixel having the same value is not yet labelled, apply a new numerical value of label.

(3) When mutually different numerical values of labels are applied to a plurality of adjacent pixels each having the same value standardize themselves with one smaller in the numerical value.

FIG. 27(B) is representative of a labelling image in which the respective pixels are labelled in accordance with the algorithm of (1)–(3) set forth above. In the labelling image thus produced, the periphery of the coupling portions (labelled "1") which are inward in the gradient direction, surrounding the central point (+), is determined as the boundary line of the arithmetic effective domain, as shown in FIG. 27(C). Even if the portion, which is outward in the gradient direction, is included in the inside of the domain surrounded by the boundary line thus determined, the whole of the domain surrounded by the boundary line is determined as the arithmetic effective domain.

Figure 28A:
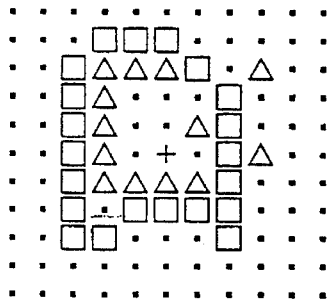
FIGS. 28(A)–28(C) are each an illustration useful for understanding as to how an outline is determined in accordance with outline arithmetic means shown in FIG. 26.
Figure 28B:
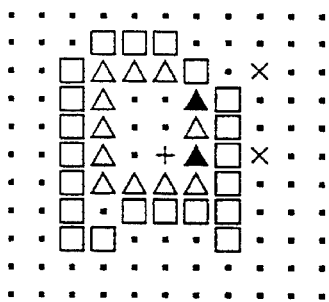
Figure 28C:
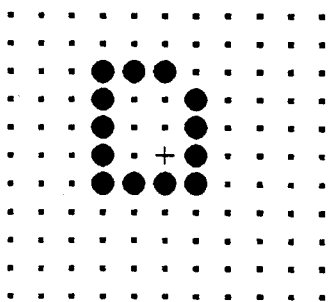

FIGS. 28(A)–28(C) are each an illustration useful for understanding as to how an outline is determined in accordance with outline arithmetic means shown in FIG. 26.

When the contour point (the maximal point having the maximum characteristic quantity) is determined on the respective assigned lines shown in FIG. 2, for the time being, regardless of the arithmetic effective domain, as shown in FIG. 28(A), if the contour point is found out of the arithmetic effective domain, such a contour point is omitted and the new contour point is found within the arithmetic effective domain, as shown in FIG. 28(B), so that the outline as shown in FIG. 28(C) is extracted.

According to the scheme of the flowchart shown in FIG. 26, providing the arithmetic effective domain detecting means permits the outline to be determined with greater accuracy.

Figure 29:
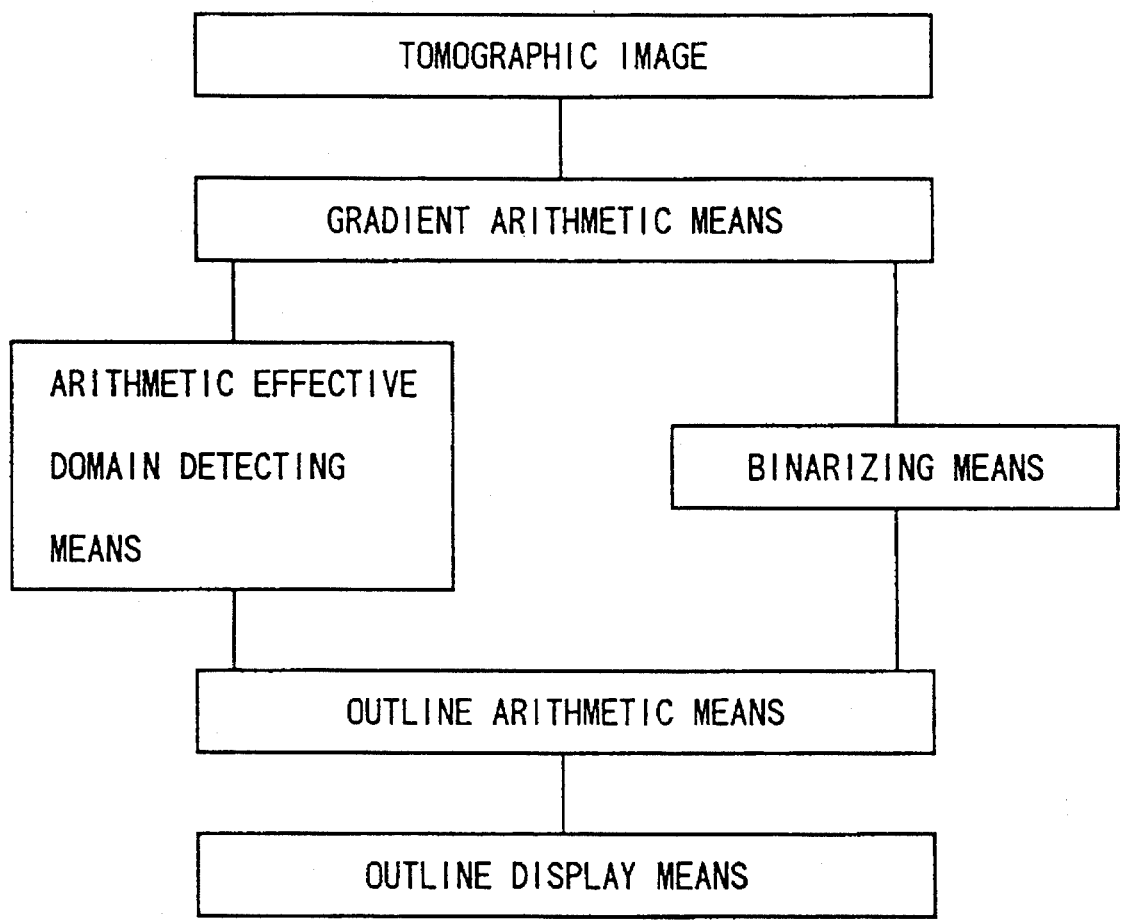
FIG. 29 is another flowchart, in which an outline is extracted and displayed, useful for understanding the second ultrasonic diagnostic system according to an embodiment of the present invention.

FIG. 29 is another flowchart, in which an outline is extracted and displayed, useful for understanding the second ultrasonic diagnostic system according to an embodiment of the present invention.

With respect to the flowchart shown in FIG. 29, the difference between it and that shown in FIG. 26 resides in the point that the flowchart shown in FIG. 26 is provided with the scalar quantity arithmetic means and the maximal point arithmetic means, whereas the flowchart shown in FIG. 29 is provided with binarizing means. According to the binarizing means, image data (luminance) on each pixel is compared with a predetermined threshold and is binarized. The outline is determined on the basis of the binary image thus obtained.

Figure 30A:
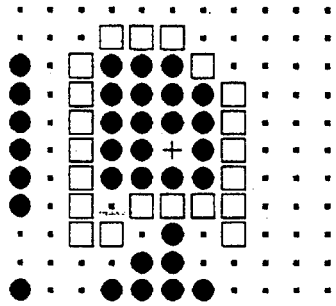
FIGS. 30(A)–30(C) are each an illustration useful for understanding as to how an outline is determined based on the binary image.
Figure 30B:
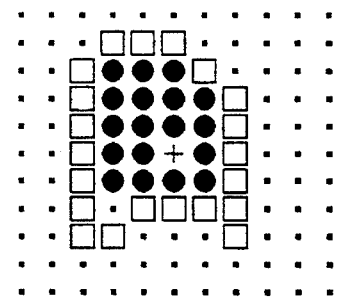
Figure 30C:
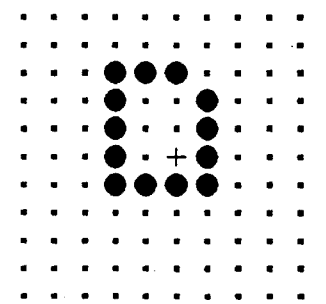

FIGS. 30(A)–30(C) are each an illustration useful for understanding as to how an outline is determined based on the binary image.

As shown in FIG. 30(A), the blood flow portion represented by the binary image spreads inside and outside the boundary line of the arithmetic effective domain. And as shown in FIG. 30(B), only the portion inside the boundary line of the blood flow portion is extracted, and the outline is determined along the periphery of the blood flow portion (FIG. 30(C)).

Figure 46A:
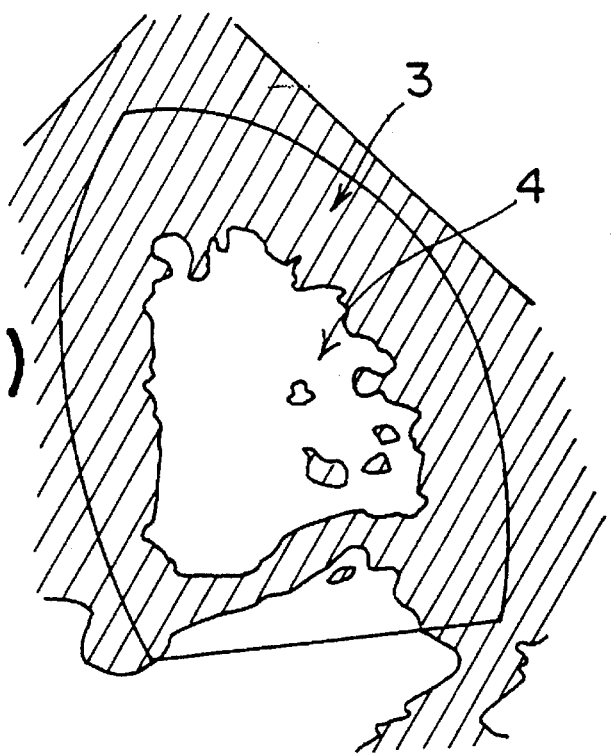
FIGS. 46(A) and 46(B) are each an illustration showing a tomographic image and the designated domain on the tomographic image.
Figure 46B:
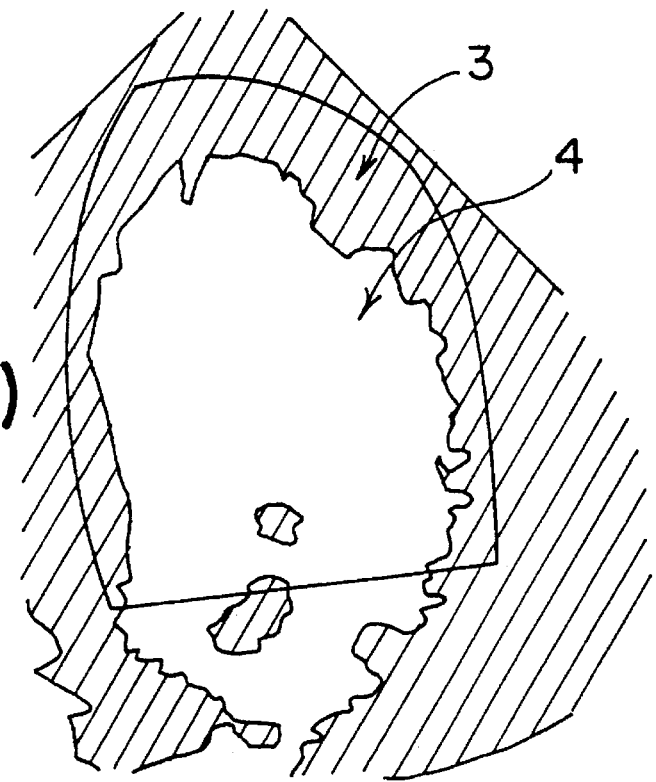

In this manner, determination of the arithmetic effective domain may avoid the necessity of entry of the approximate domain 3 by an operator, as described referring to FIGS. 46(A) and (B). Thus, it is possible to prevent the erroneous extraction of the outline due to a mistake in entry.

Figure 31:
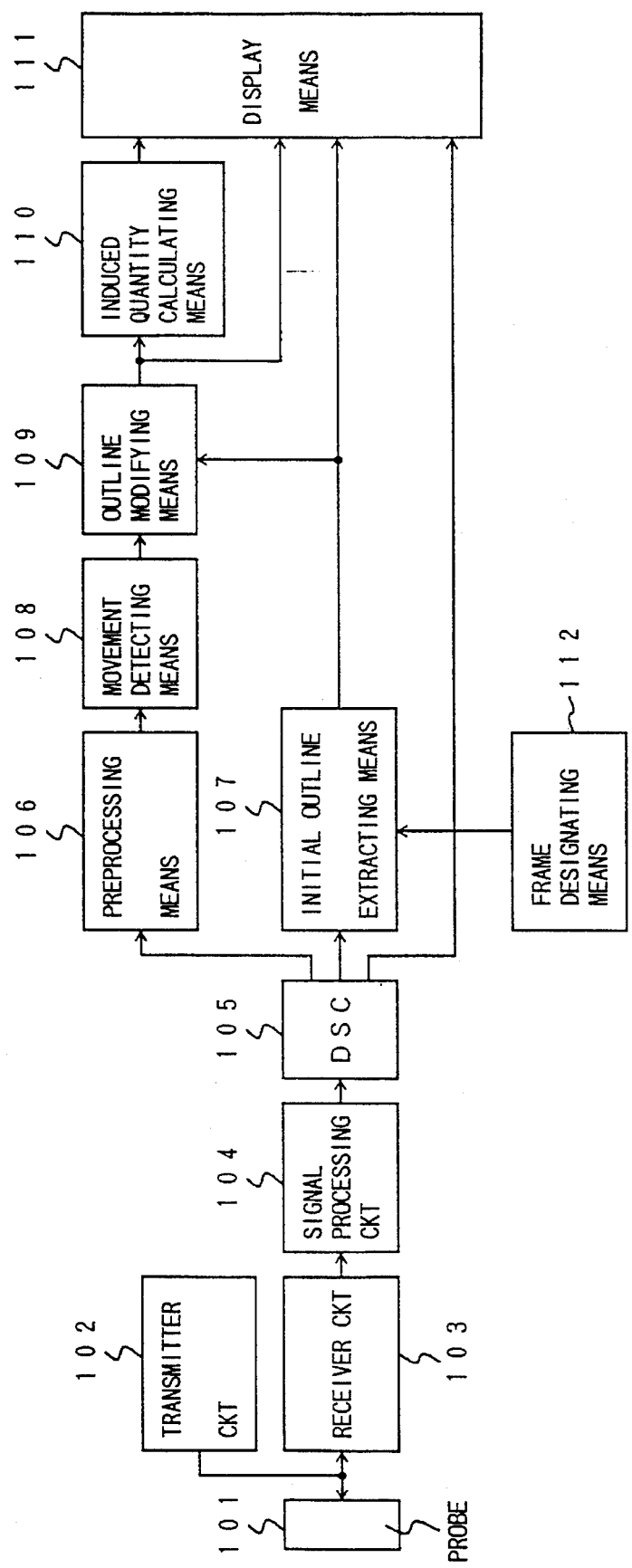
FIG. 31 is a block diagram schematically showing the third ultrasonic diagnostic system embodying the present invention.

FIG. 31 is a block diagram schematically showing the third ultrasonic diagnostic system embodying the present invention.

This ultrasonic diagnostic system is provided with a ultrasonic probe 101 for transmitting and receiving ultrasonic acoustic waves. A transmission circuit 102 transmits a transmission pulse to the ultrasonic probe 101. Upon receipt of the transmission pulse, the ultrasonic probe 101 transmits ultrasonic acoustic waves toward the subject (not illustrated). The ultrasounds reflected from the inside of the subject are received by the ultrasonic probe 101. A receiving circuit 103 receives received signals. In the receiving circuit 103, the received signals are beamformed so that scan lines are formed within the subject. A signal processing circuit 104 receives a signal outputted from the receiving circuit 103. The signal processing circuit 104 comprises a logarithmic amplifier, a detector circuit, a filter processing circuit, an A/D converter and the like. In the signal processing circuit 104, necessary signal processing is implemented and the analog signal is converted into a digital signal (image data) in the form of output. A digital scan converter (DSC) 105 receives the digital signal outputted from the signal processing circuit 104. The digital scan converter (DSC) 105 converts data involved in the scan line direction of the ultrasonic waves into data involved in the scan line of the TV screen. The image data outputted from the DSC 105 is supplied to a display means 111 having a CRT so that a tomographic image is displayed on its display screen. Further, the image data outputted from the DSC 105 is supplied also to an initial outline extracting means 107 (an example of outline arithmetic means referred to in the present invention). The initial outline extracting means 107 serves to determine the outline of the left ventricle of the heart for example, on a frame designated by frame designating means 112, in a similar fashion to that of the outline extracting scheme in the first ultrasonic diagnostic system embodying the present invention mentioned above. In the frame designating means 112, a frame is designated on the basis of the electrocardiogram or Doppler waveform. Alternatively, it is acceptable to freeze the display screen so that an operator directly designates a frame. The outline thus determined in the initial outline extracting means 107 is inputted to the display means 111 so that the outline is displayed superposing on the tomographic image. The outline determined in the initial outline extracting means 107 is inputted also to outline modifying means 109 which will be described later.

The image data outputted from the DSC 105 is supplied also to preprocessing means 106 for performing preprocessing for arithmetic of evaluating movement in movement detecting means 108. The movement detecting means 108 serves to detect movements of the respective points of the subject within a tomographic surface. When the movement detecting means 108 detects movement using an optical flow method, the preprocessing means 106 performs a smoothing process. When the movement detecting means 108 detects movement using a cross correlation method, the preprocessing means 106 performs a binarizing process.

Upon receipt of the image data subjected to the preprocessing in the preprocessing means 106, the movement detecting means 108 detects movement in the tomographic surface of the subject. Information as to the movement thus detected is inputted to the outline modifying means 109. Inputted to the outline modifying means 109 is also the outline determined in the initial outline extracting means 107, as mentioned above. Thus, the outline is modified to meet the outline of the frame which has been processed now in the outline modifying means 109. Incidentally, the outline modifying means 109 determines the outline of the frame in processing through sequentially modifying further the outline modified once in the outline modifying means 109, but not modifying the original outline extracted for each frame by the initial outline extracting means 107. The outline modified by the outline modifying means 109 is supplied to the display means 111 to be displayed on its display screen superposing on the tomographic image of the associated frame. The outline outputted from the outline modifying means 109 is supplied also to induced quantity calculating means 110. The induced quantity calculating means 110 evaluates, on the basis of the entered outline, the induced quantity derived from the outline, such as area inside the outline, position of the center of gravity, volume inside the outline and the like. Further, in case of necessity, it is possible to evaluate the difference value of the induced quantity over a plurality of frames. The induced quantity or the difference value is supplied to the display means 111 to be displayed in the form of numerical values, a graph and the like.

In the arrangement shown in FIG. 31, with respect to the tomographic image outputted from the DSC 105 and inputted to the display means 111, the outline outputted from the initial outline extracting means 107 and inputted to the display means 111, the outline outputted from the outline modifying means 109 and inputted to the display means 111, and the induced quantity or the difference value outputted from the induced quantity calculating means 110 and inputted to the display means 111, a timing control is implemented so that a quantity as to the same frame is simultaneously inputted to the display means 111.

Figure 32:
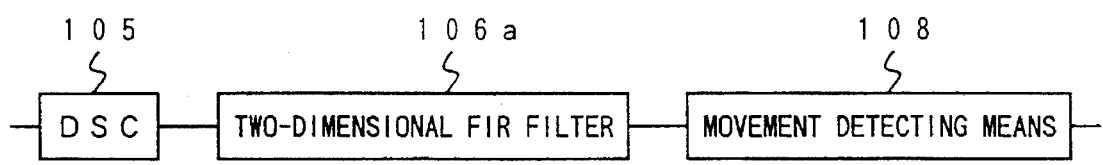
FIG. 32 is a block diagram showing a concrete example of pre-treatment means of the ultrasonic diagnostic system shown in FIG. 31.

FIG. 32 is a block diagram showing a concrete example of preprocessing means 106 of the ultrasonic diagnostic system shown in FIG. 31.

The image data outputted from the DSC 105 is supplied to a two-dimensional FIR filter 106a as an example of the preprocessing means 106 to be smoothed. In a case where the movement detecting means 108 detects movement through performing the two-dimensional cross correlation arithmetic, it is not necessarily needed to perform a smoothing process. However, in a case where the movement detecting means 108 detects movement through performing the optical flow arithmetic, it is preferable to perform a smoothing process as the preprocessing by the two-dimensional FIR filter 106a, since the optical flow method concerns a technique which is implemented on the assumption that the received image is spatially smooth.

Figure 33:
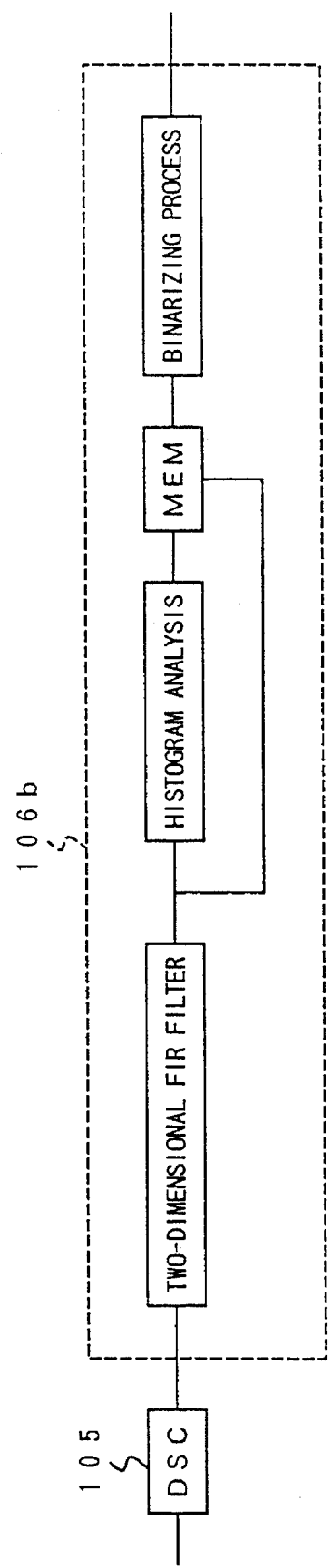
FIG. 33 is a block diagram showing another concrete example of the pre-treatment means.

FIG. 33 is a block diagram showing another concrete example of the preprocessing means 106.

Preprocessing means 106b comprises a two-dimensional FIR filter, a histogram analyzer unit, a memory (MEM) and a binarizing processing unit. The two-dimensional FIR filter is not necessarily needed.

The histogram analyzer unit produces a histogram of image data to analyze how luminance values of an image are distributed, and processes data in such a manner that a luminance distribution is accommodated within a predetermined range, and then the data thus processed is stored in the memory. The binarizing processing unit binarizes the image data thus processed with a predetermined threshold level. Such a binarizing processing unit is useful in the point that the operation speed is enhanced, when the movement detecting means 108 detects movement through performing a cross correlation arithmetic.

Figure 34:
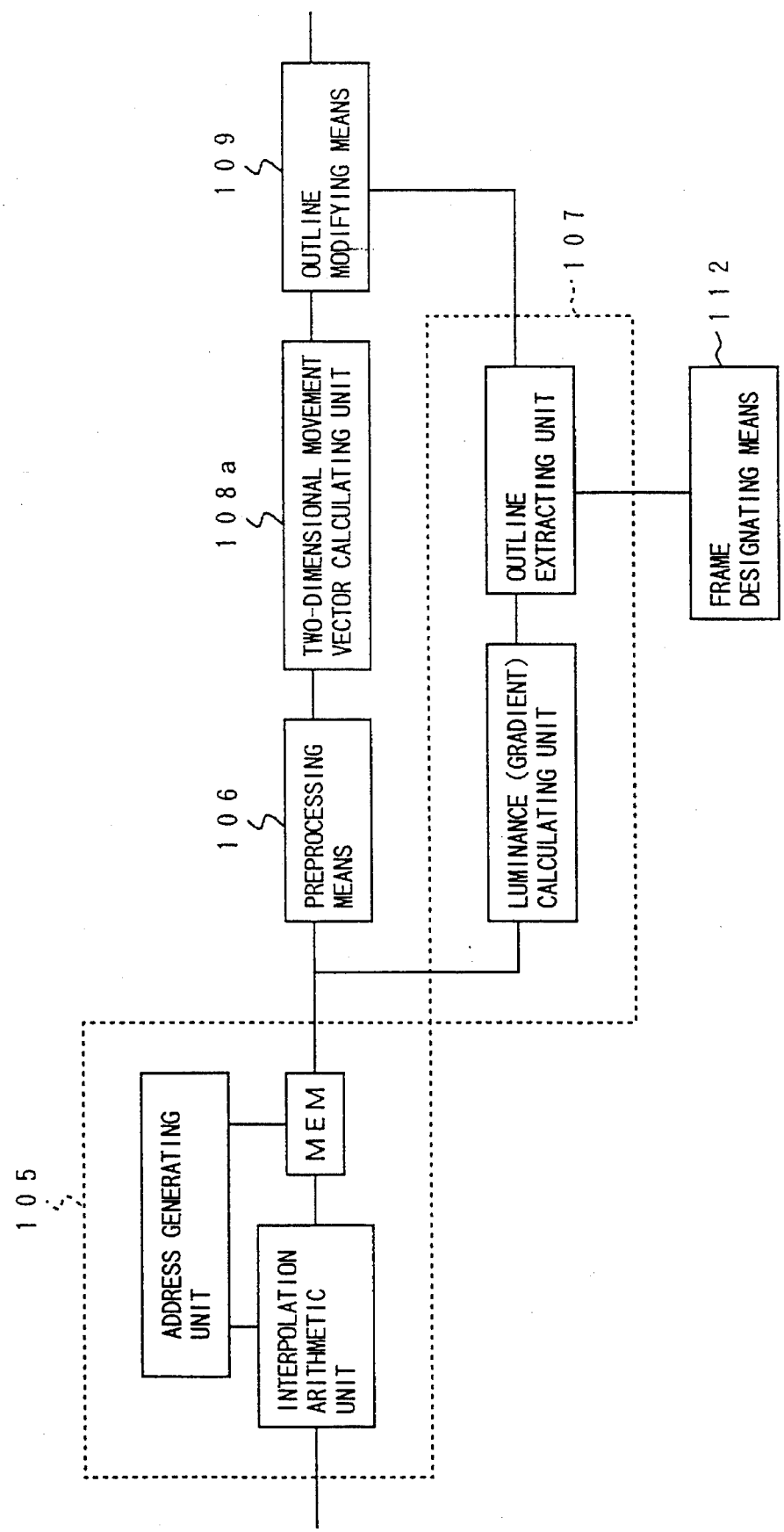
FIG. 34 is a block diagram of an example of a partially detailed functional structure of the ultrasonic diagnostic system shown in FIG. 31.

FIG. 34 is a block diagram of an example of a partially detailed functional structure of the ultrasonic diagnostic system shown in FIG. 31.

The DSC 105 serves, as mentioned above, to convert ultrasound-scan line data to TV-scan line data, and comprises an address generating unit, an interpolation arithmetic unit and a memory (MEM). The address generating unit performs designation of data for use in the interpolation arithmetic and designation of address of the memory. The interpolation arithmetic unit practices the interpolation arithmetic on ultrasound-scan line data to produce the TV-scan line data. The TV-scan line data thus produced is temporarily stored in the memory. This memory has a storage capacity capable of storing, for example, 64 frames of image data, and is arranged in such a way that when data exceeding the number of frames of its capacity is inputted, it permits data to be sequentially overwritten, and data are sequentially erased in the order of oldest one.

The preprocessing means 106 performs a suitable space filtering process and the like. A two-dimensional movement vector calculating means 108a, as an example of the movement detecting means shown in FIG. 31, calculates a two-dimensional movement vector on each of a plurality of points within a tomographic surface using image data of frames which are adjacent on a time basis.

The initial outline extracting means 107 comprises a luminance gradient calculating unit and an outline extracting unit. The luminance gradient calculating unit calculates spatial luminance gradient on each of the points within the frame (referred to as "initial frame" hereinafter) which is designated by the frame designating means 112. The outline extracting unit extracts an outline of a predetermined tissue, for example, the left ventricle, in the initial frame on the basis of the gradient thus calculated. Incidentally, the outline in the initial frame is referred to as "initial frame".

The outline modifying means 109 sequentially determines the outline in a frame adjacent to the initial frame in turn using the calculated initial outline and two-dimensional movement vector.

Figure 35:
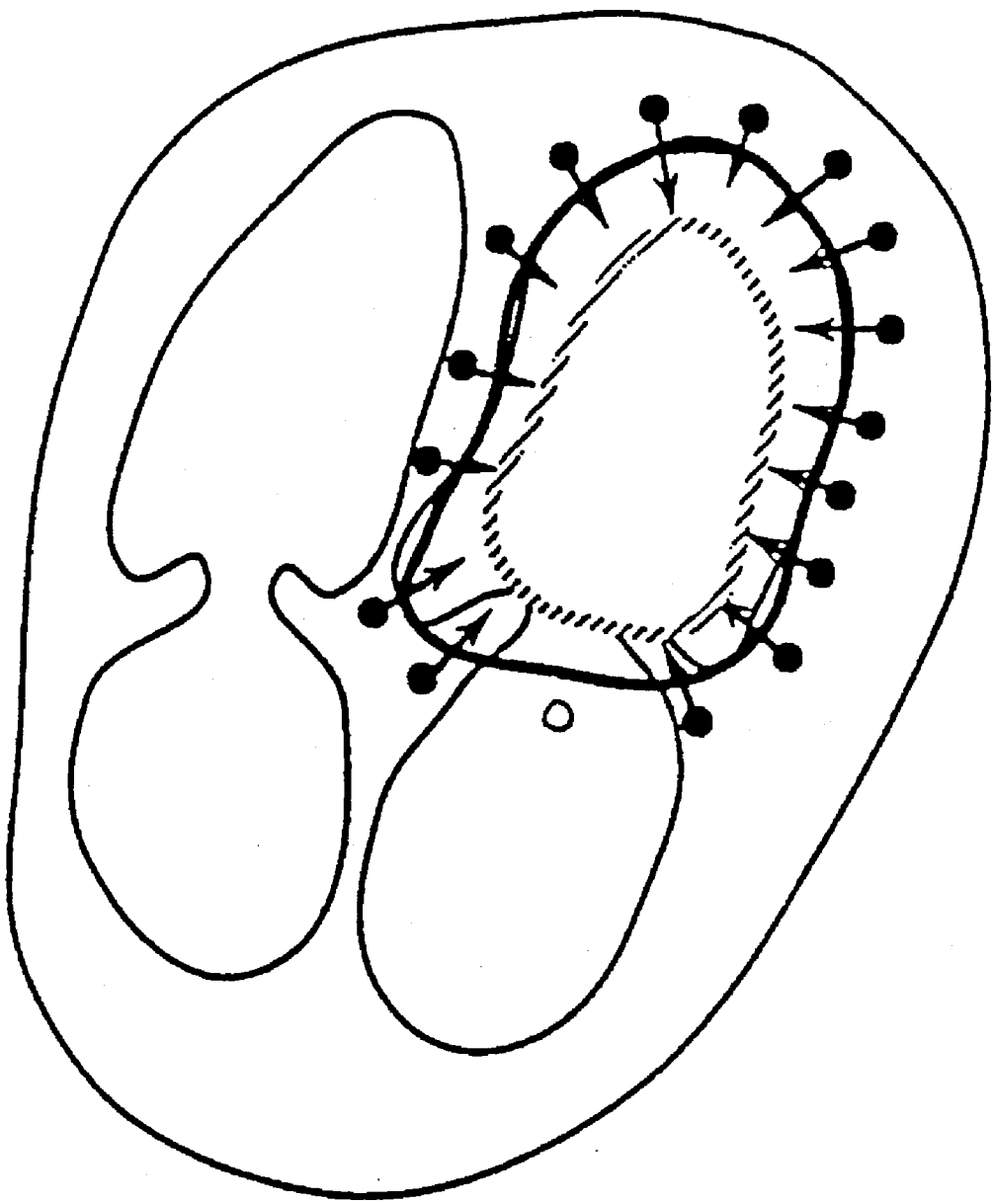
FIG. 35 is a typical illustration showing a tomographic image of the heart to illustrate arithmetic contents in two-dimensional movement vector calculating unit and outline modification means which are shown in FIG. 34.

FIG. 35 is a typical illustration showing a tomographic image of the heart to illustrate arithmetic contents in two-dimensional movement vector calculating unit 108a and outline modification means 109 which are shown in FIG. 34.

The outline depicted by the thick line in FIG. 35 is the initial outline or the modified outline in the frame immediately before it. The points marked with black-dots denote points inside the myocardium near to the outline on which a two-dimensional movement vector is calculated by the two-dimensional movement vector calculating unit 108a. The arrows extending from the points marked with black-dots denote each the calculated two-dimensional movement vector. The outline depicted by the broken line is representative of the outline modified on the basis of the calculated two-dimensional movement vector. The point marked with a white-dot is out of the myocardium and is of extremely weak in reflected ultrasound. Thus, there is a high possibility such that the two-dimensional movement vector determined with respect to this white-dot is not representative of the exact movement. Consequently, it is so arranged that this point does not take part in modification of the outline on the basis of image luminance information. With respect to the outline after modification, it is preferable to determine it fitting the spline function and the like.

Figure 36:
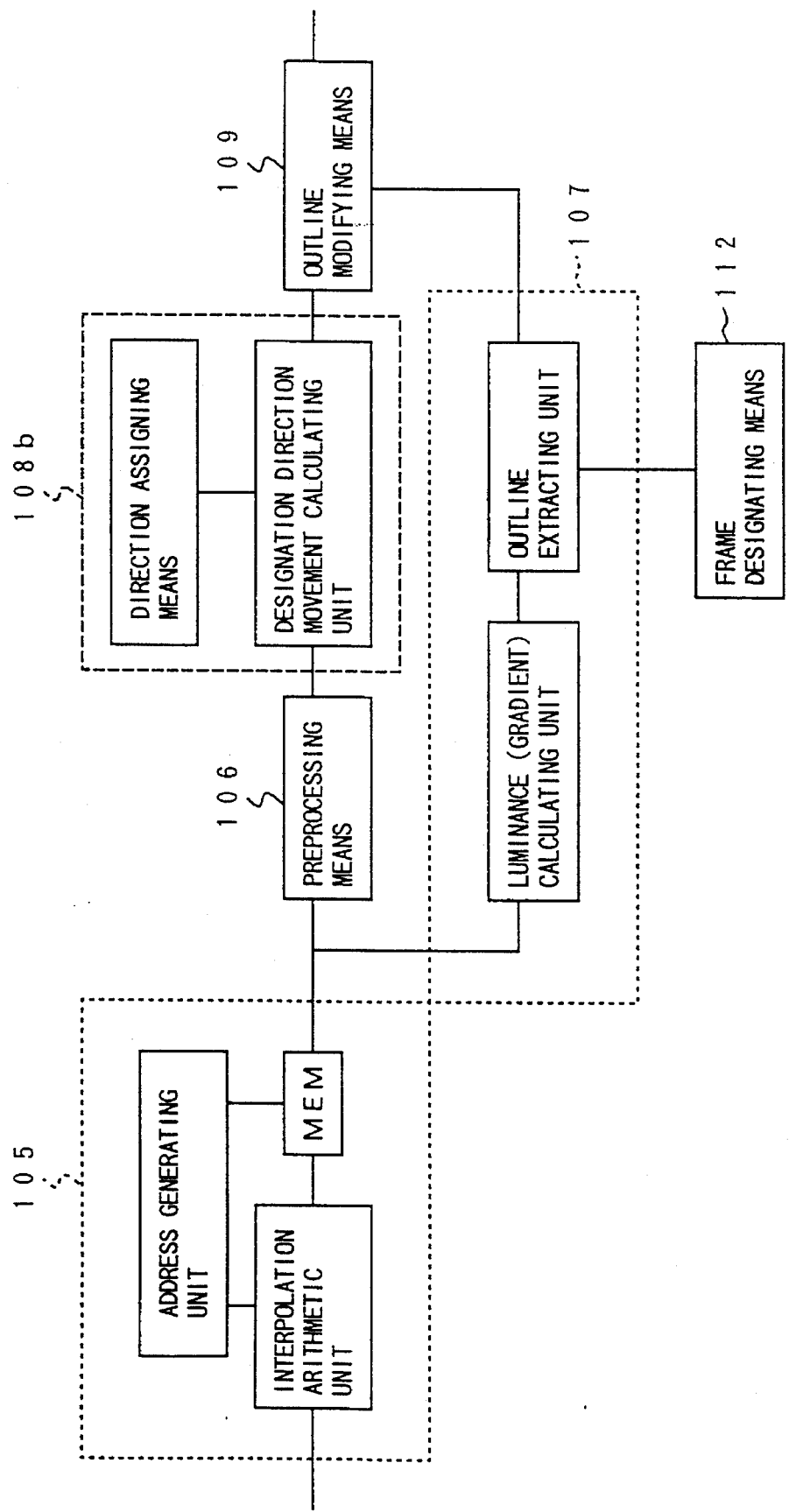
FIG. 36 is a block diagram of another example of a partially detailed functional structure of the ultrasonic diagnostic system shown in FIG. 31.
Figure 37:
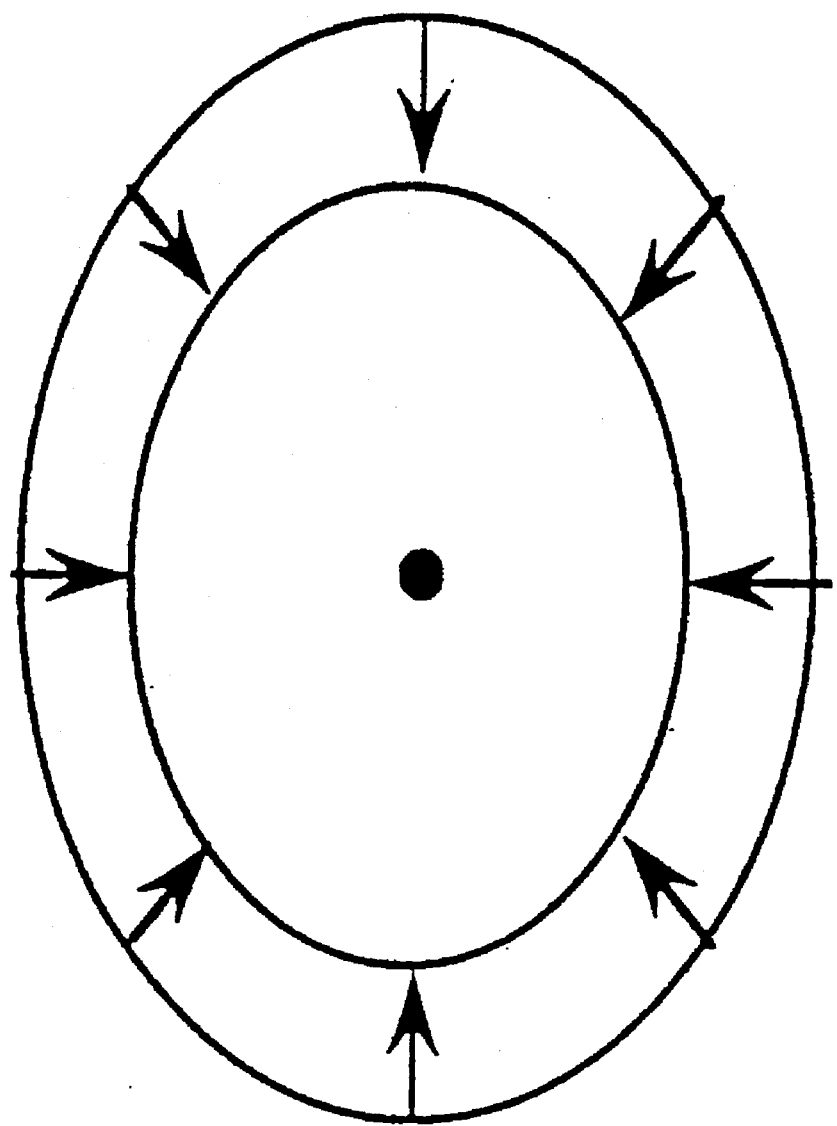
FIG. 37 is an explanatory view useful for understanding a method of assigning beforehand a detecting direction for a movement.

FIG. 36 is a block diagram of another example of a partially detailed functional structure of the ultrasonic diagnostic system shown in FIG. 31. FIG. 37 is an explanatory view useful for understanding a method of assigning beforehand a detecting direction for a movement.

With respect to the arrangement shown in FIG. 36, the difference between it and that shown in FIG. 31 is that the movement detecting means 108d comprises a direction assigning means and an assigned direction movement calculating unit.

The direction assigning means assigns, as shown in FIG. 37, a predetermined central point inside the outline. It is acceptable to perform manually the assignment of the central point. Alternatively, it is also acceptable to perform automatically the assignment of the central point in such a manner that a point of the center of gravity of the initial outline already determined or the outline of the frame immediately before it is determined and the point of the center of gravity is selected as the central point.

The assigned direction movement calculating unit evaluates, as shown in FIG. 37, a magnitude of a movement of the direction directed toward the assigned central point. In the case, it is sufficient to perform a one-dimensional arithmetic in the direction directed to the central point, different from the calculation of the two-dimensional movement vector by the two-dimensional movement vector calculating unit 108a shown in FIG. 34. With respect to the manner as to how the outline is modified, it is similar to the fashion mentioned above.

Figure 38:
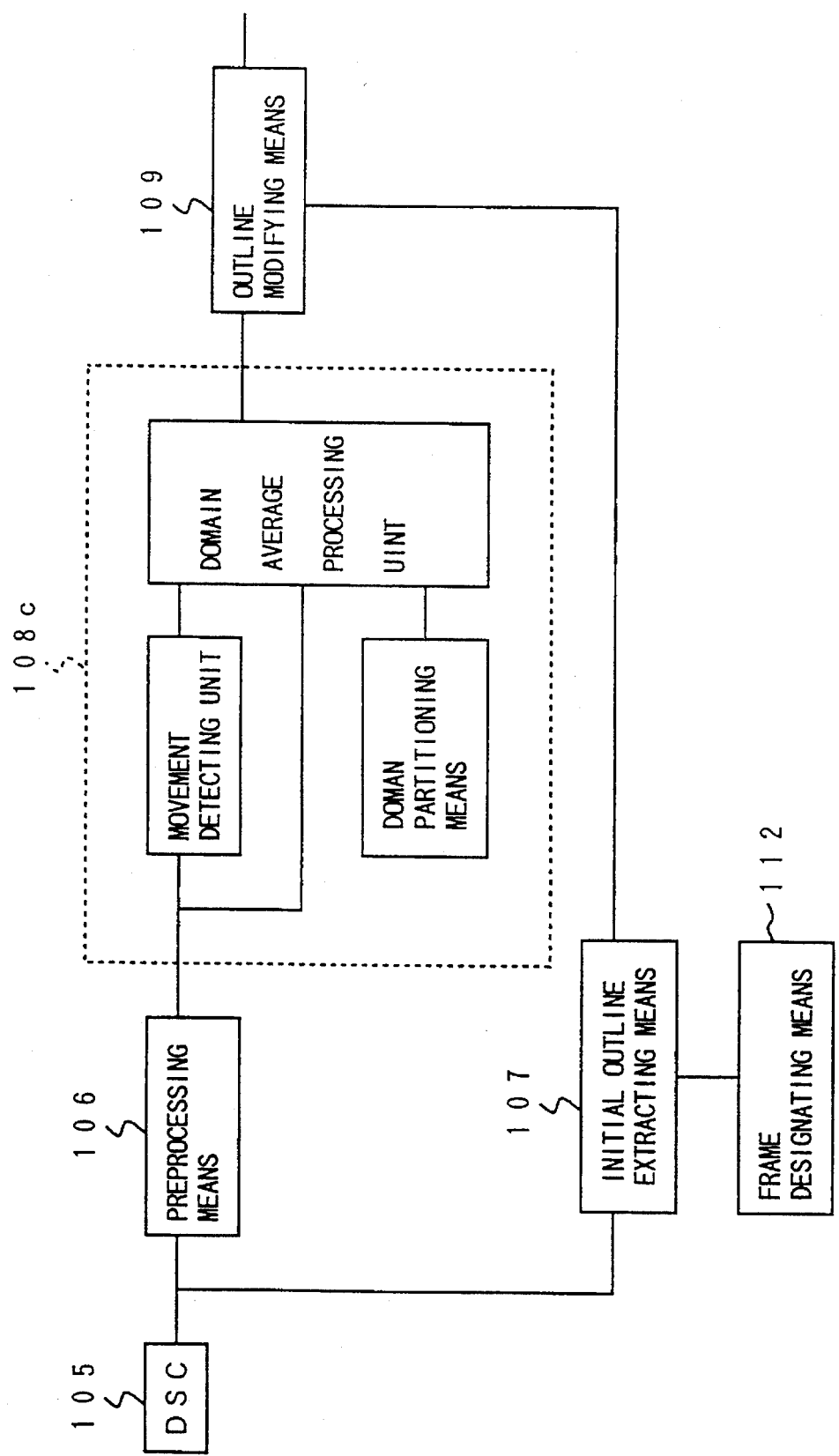
FIG. 38 is a block diagram of another example of movement detecting means shown in FIG. 31.
Figure 39:
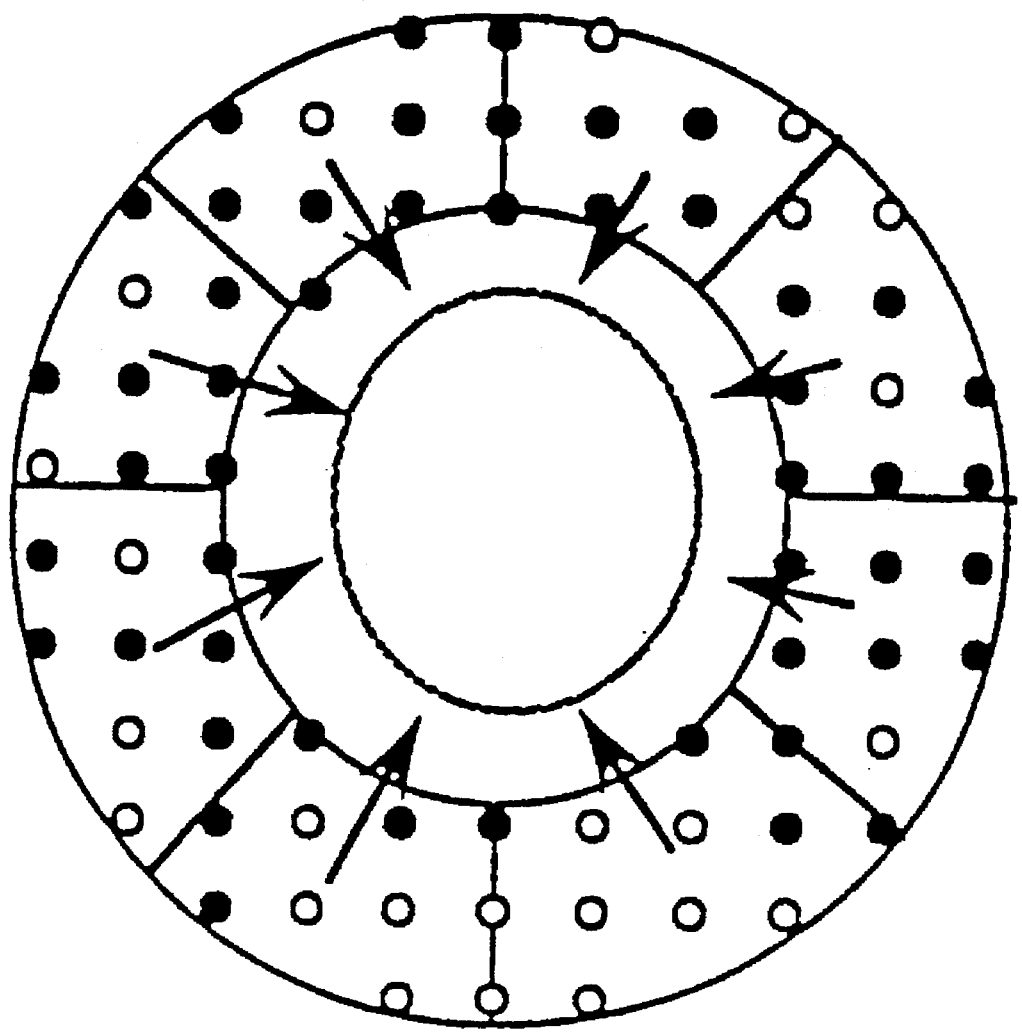
FIG. 39 is an explanatory view useful for understanding the movement detecting means shown in FIG. 38.

FIG. 38 is a block diagram of another example of movement detecting means 108 shown in FIG. 31. FIG. 39 is an explanatory view useful for understanding the movement detecting means shown in FIG. 38.

Movement detecting means 108c comprises a movement detecting unit, domain partitioning means and a domain average processing unit. The domain partitioning means performs, for example, as shown in FIG. 39, a designation such that the neighborhood of the outline is partitioned into 8 segments in a radial direction. The movement detecting unit calculates movement vectors from the adjacent frames on a plurality of points on each domain. The domain average processing unit refers to image data outputted from the preprocessing means 106 (or image data directly outputted from the DSC 105 without passing through the preprocessing means 106), and determines an average movement vector of the effective movement vectors in such a manner that if a luminance value at the point on which a movement vector is calculated is larger than a predetermined value, it is decided that the movement vector on that point is valid (corresponding to the points marked with black-dots in FIG. 39), whereas if the luminance value is smaller than the predetermined value, it is decided that the movement vector on that point is invalid (corresponding to the point marked with a white-dot in FIG. 39). The outline modifying means 109 modifies the initial outline or an outline of the frame immediately before that of interest to determine the outline suitable for the frame of interest.

Figure 40:
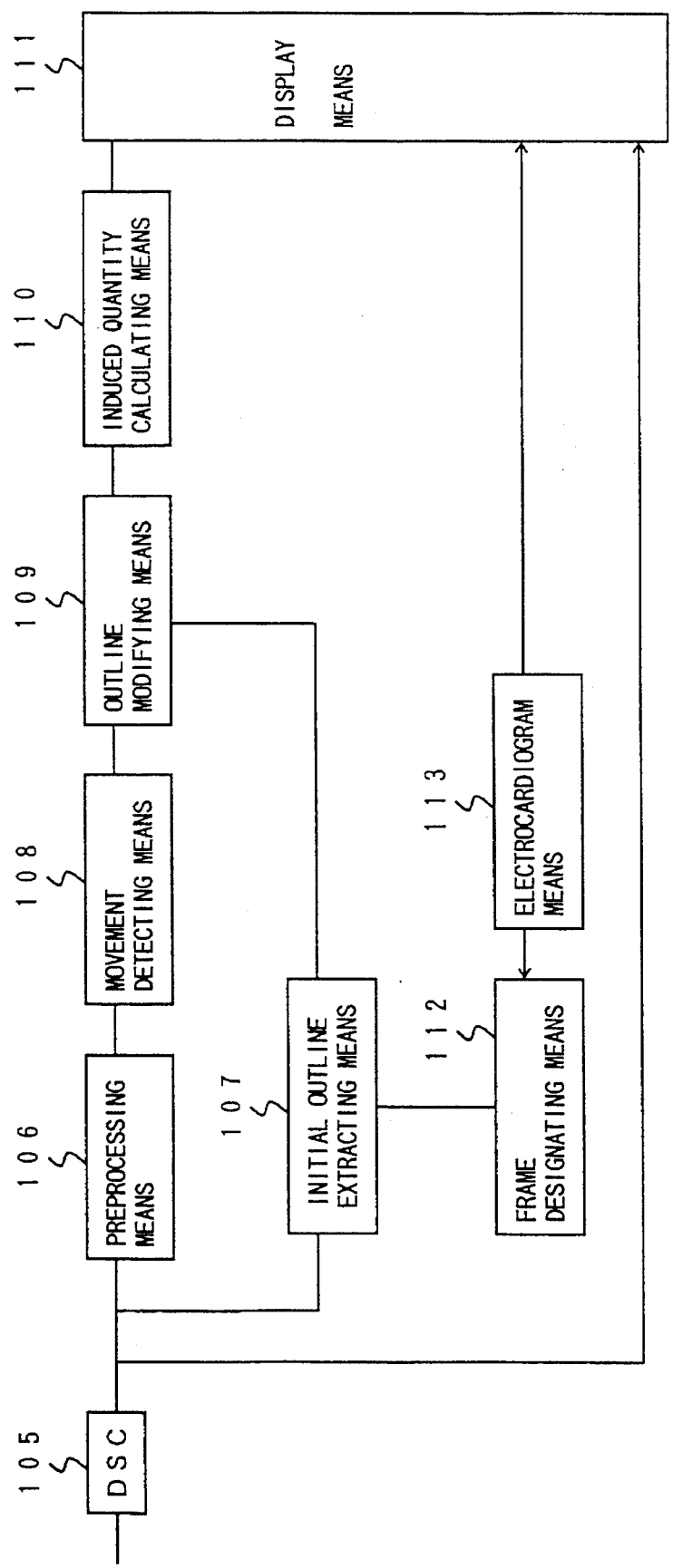
FIG. 40 is a partial block diagram showing a functional structure of the ultrasonic diagnostic system shown in FIG. 31, into which electrocardiogram means for inputting an electrocardiogram of a patient (subject) is incorporated.
Figure 41:
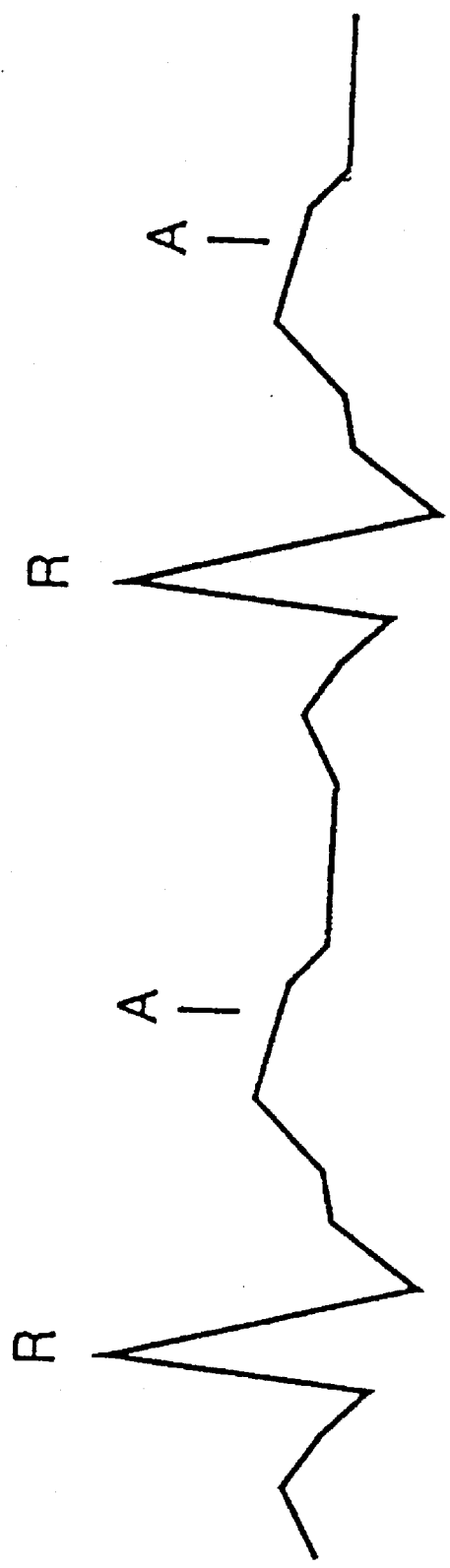
FIG. 41 is a typical illustration of an electrocardiogram waveform.

FIG. 40 is a partial block diagram showing a functional structure of the ultrasonic diagnostic system shown in FIG. 31, into which electrocardiogram means for inputting an electrocardiogram of a patient (subject) is incorporated. FIG. 41 is a typical illustration of an electrocardiogram waveform.

The electrocardiogram means 113 shown in FIG. 40 receives an electrocardiogram as shown in FIG. 41 and transmits the same to the display means 111 which displays on its display screen the electrocardiogram as shown in FIG. 41 along with the usual ultrasonic tomographic image.

The electrocardiogram entered through the electrocardiogram means 113 is supplied also to the frame designating means 112. The frame designating means 112 detects R-waves (cf. FIG. 41) on the electrocardiogram, and designates the frames on A points which appear each after a predetermined time passes since occurrence of the R-wave. The initial outline extracting means 107 determines, as mentioned above, the initial outline of the frame designated by the frame designating means 112.

Figure 42:
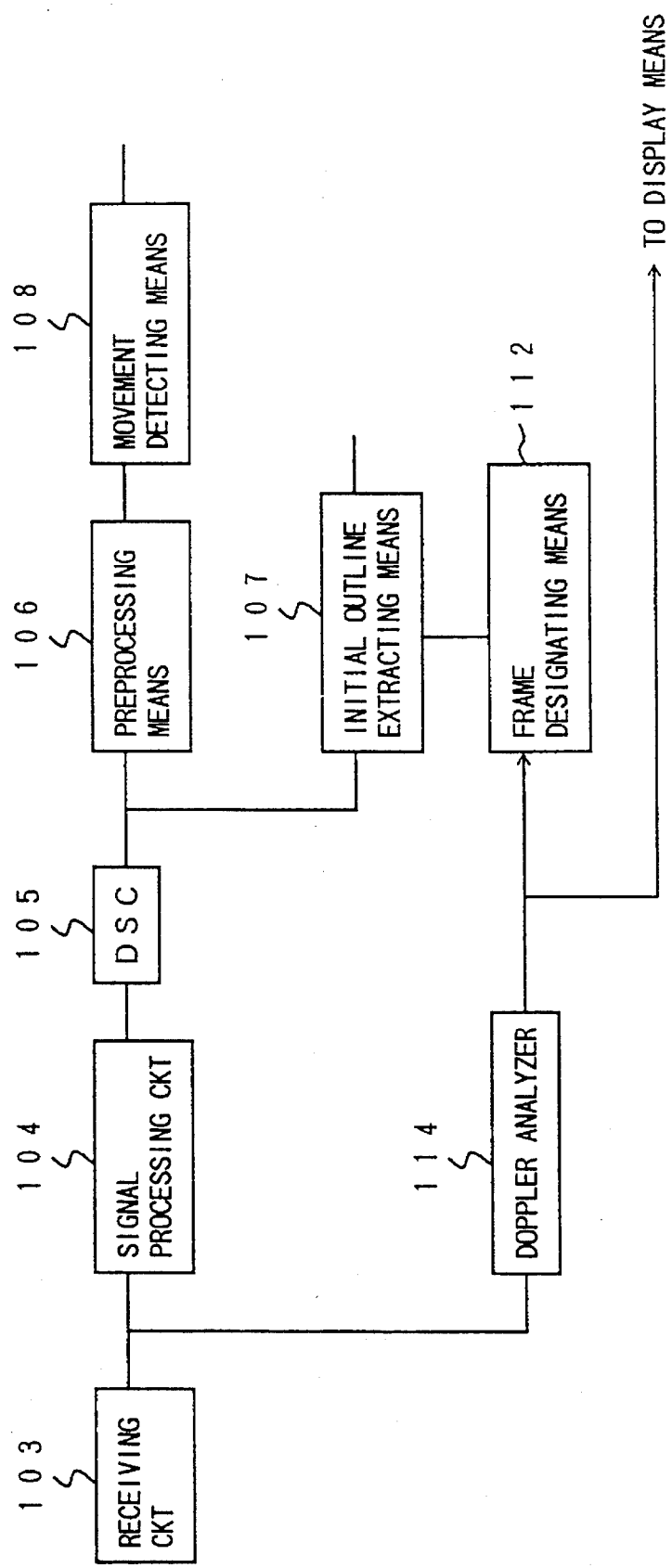
FIG. 42 is a partial block diagram showing a functional structure of the ultrasonic diagnostic system shown in FIG. 31, into which a Doppler analyzer unit is incorporated.

FIG. 42 is a partial block diagram showing a functional structure of the ultrasonic diagnostic system shown in FIG. 31, into which a Doppler analyzer unit is incorporated.

Usually, the ultrasonic diagnostic system is provided with the function (Doppler analyzer unit 114) of calculating, for example, a blood flow velocity or the like in accordance with Doppler operation. The Doppler analyzer unit 114 outputs information representative of time variation of the blood flow velocity. The time variation of the blood flow velocity is synchronized with the beat of the heart. Information as to the blood flow velocity is supplied to the frame designating means 112. The frame designating means 112 designates the frame, on which the initial outline is to be extracted, on the basis of the received information as to the blood flow velocity, instead of the electrocardiogram in FIG. 40.

Figure 43:
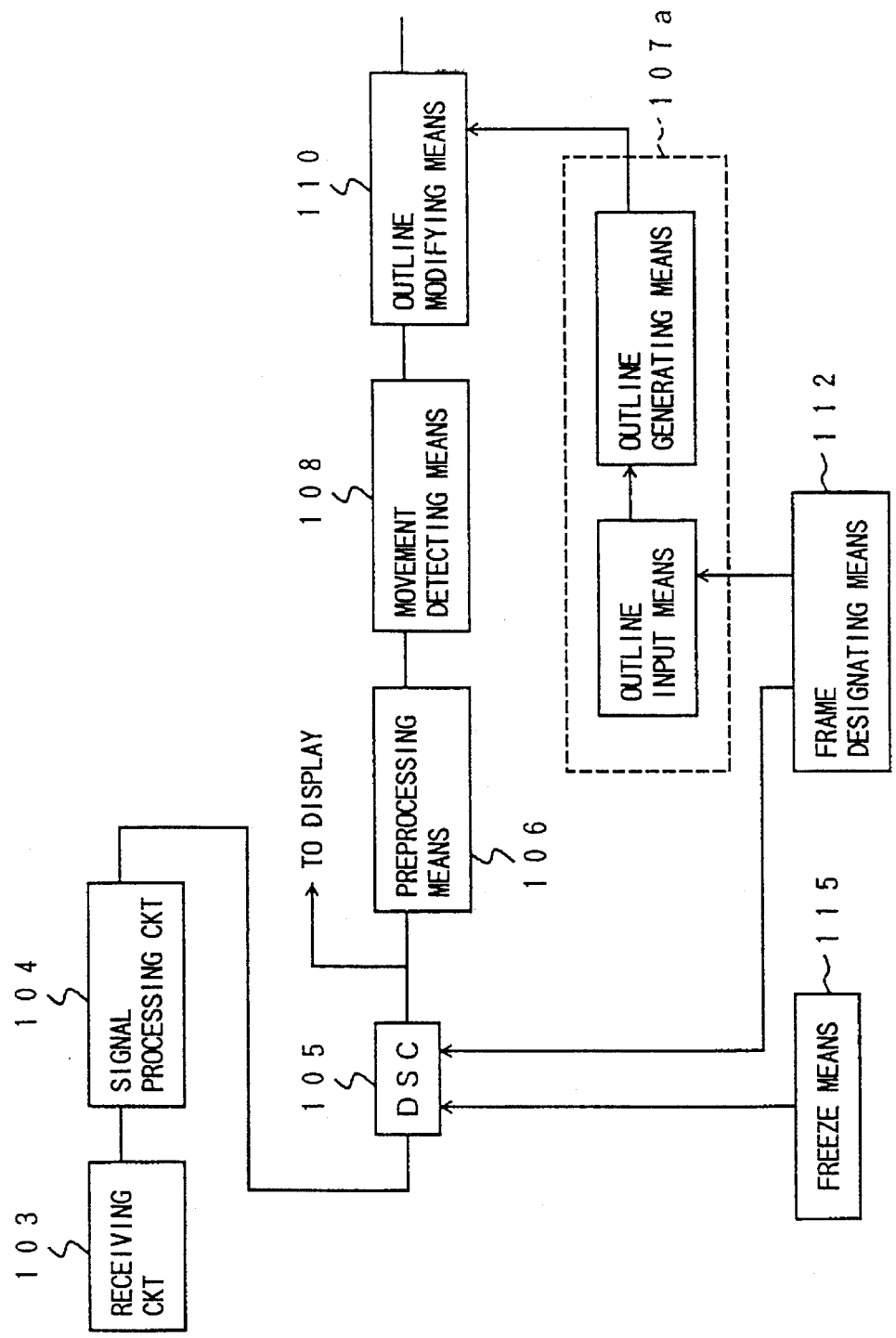
FIG. 43 is a block diagram showing a functional structure of the ultrasonic diagnostic system shown in FIG. 31, into which freeze means is incorporated, wherein an example of initial outline extracting means is schematically shown with blocks.

FIG. 43 is a block diagram showing a functional structure of the ultrasonic diagnostic system shown in FIG. 31, into which freeze means is incorporated, wherein an example of initial outline extracting means is schematically shown with blocks.

As mentioned before, the DSC 105 is provided with a memory for storing, for example, 64 frames of image data (cf. FIG. 34). When an operator performs a predetermined operation, the freeze means 115 outputs to the DSC 105 a freeze command to save the image data now stored in the memory and inhibit overwrite of any new image data. The frame designating means 112 designates the frame, on which the initial outline is to be determined, in accordance with an instruction of an operator, or on the basis of the electrocardiogram or the blood flow velocity information as described referring to FIGS. 40 and 42. The DSC 105 outputs image data involved in the initial frame to the display means 111 to display on its display screen the tomographic image of the initial frame. An operator may input points (contour points) on the outline in the initial frame using the outline input means constituting the initial outline extracting means 107a.

The contour line thus entered is supplied to the outline producing means. The outline producing means determines the initial outline with, for example, the broken line, the spline curve or the like, on the basis of the entered contour points. The initial outline thus determined is supplied to the outline modifying means 110. The outline modifying means 110. The outline modifying means 110 determines the outline on the frame other than the initial frame among 64 frames for example stored in the DSC 105.

Figure 44A:
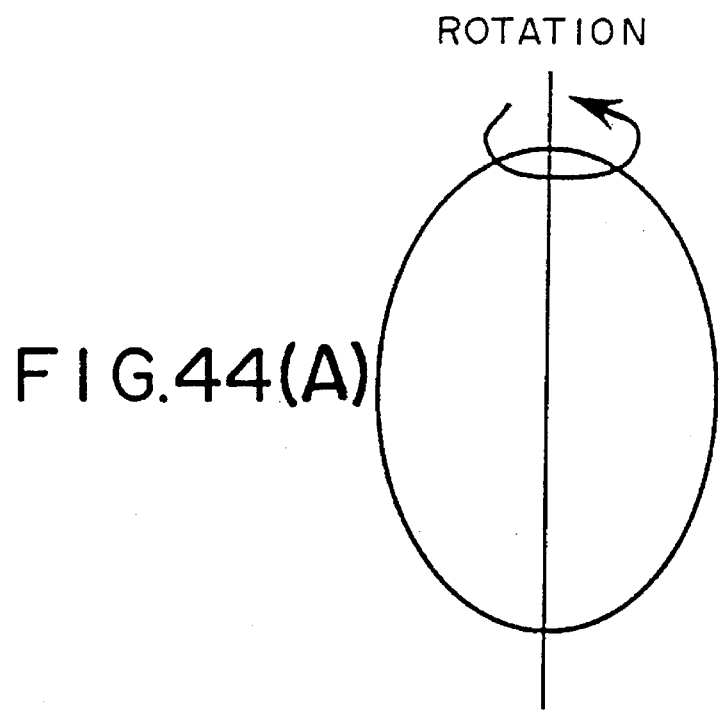
FIGS. 44(A) and 44(B) are each a typical illustration showing an example as to how the volume of the inside of the outline is evaluated by induced quantity calculating means of the ultrasonic diagnostic system shown in FIG. 31.
Figure 44B:
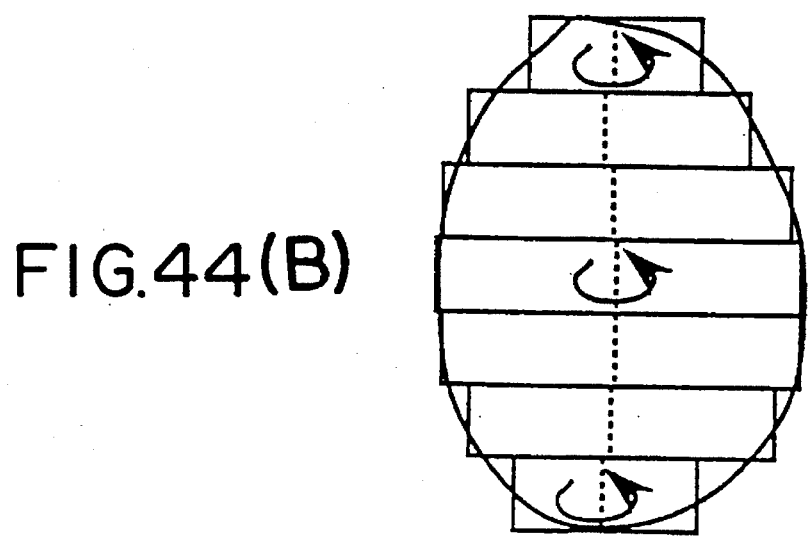
Figure 45:
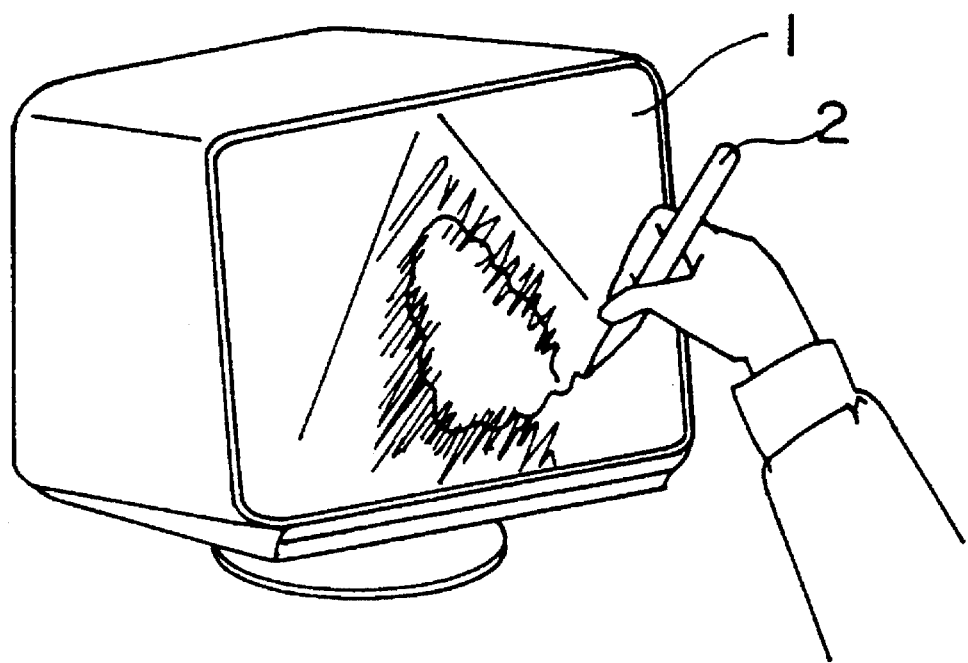
FIG. 45 is an illustration showing the state that the tomographic image displayed on a display is traced with a light-pen.

FIGS. 44(A) and 44(B) are each a typical illustration showing an example as to how the volume of the inside of the outline is evaluated by induced quantity calculating means of the ultrasonic diagnostic system shown in FIG. 31.

FIG. 44(A) shows an ellipse approximating to the outline of the left ventricle. Rotation of the ellipse may form an ellipsoidal body of revolution, so that volume of the ellipsoidal body of revolution can be evaluated.

FIG. 44(B) shows an example in which the outline inside of left ventricle is approximated by a lot of rectangles. Rotation of each rectangle on its center axis may form the associated circular disk. Thus, the sum of volumes of their circular disks can be evaluated.

In this manner, for instance, volume of the outline inside is evaluated for each frame, and the variation of the volume is displayed, for example, as shown in FIG. 24, on the display screen.

As described above, according to the present invention, it is possible to objectively extract an outline of the tissue without a manual work, or with only a simple manual work.

Further, according to the second ultrasonic diagnostic system of the present invention, it is possible to extract an outline of the tissue with greater accuracy through deciding the arithmetic effective domain.

Furthermore, according to the third ultrasonic diagnostic system of the present invention, the outline determined on a certain frame is modified in accordance with movements on a plurality of points inside the tomographic surface, thereby determining the respective outlines on a plurality of frames in series, without performing arithmetic for determining the outline for each frame going back to the first.

The present invention is not limited to the particular embodiments described above. Various changes and modifications may be made within the spirit and scope of the invention.

We claim:

1. An ultrasonic diagnostic system wherein ultrasonic waves reflected within a subject are received, whereby image data corresponding to each point inside a tomographic surface spreading within the subject is obtained, comprising:

gradient arithmetic means for evaluating gradients of the image data on a plurality of points within the tomographic surface;

scalar quantity arithmetic means for evaluating scalar quantities each corresponding to an associated one of said gradients on the plurality of points within the tomographic surface;

maximal point arithmetic means for evaluating a plurality of maximal points within the tomographic surface so that said scalar quantities assume each a maximal value; and outline extracting means for determining an outline of a predetermined tissue within the subject on the basis of said plurality of maximal points.

2. A system according to claim 1, wherein said maximal point arithmetic means evaluates said maximal points on a plurality of assigned lines extending inside the tomographic surface on the basis of a variation of said scalar quantity in a direction along each of said plurality of assigned lines.

3. A system according to claim 2, wherein said maximal point arithmetic means adopts, as said plurality of assigned lines, a plurality of assigned lines extending radially inside the tomographic surface taking a predetermined central point within the tomographic surface as a starting point.

4. A system according to claim 2, wherein said maximal point arithmetic means comprises means for sequentially performing arithmetic on a difference between the scalar quantities on a plurality of points adjacent to each other along said assigned line to detect a variable point at which a sign of the difference is varied, means for correcting the scalar quantity on the variable point on the basis of the scalar quantity on a point near to the variable point, and means for deciding whether the variable point is to be extracted as the maximal point on the basis of a sign of the difference on the variable point when the scalar quantity corrected on the variable point is used.

5. A system according to claim 2, wherein said outline extracting means has characteristic quantity arithmetic means for evaluating characteristic quantity representative of a probability such that said maximal points are points on said outline, and said outline extracting means is arranged to extract the points on said outline from among said maximal points on the basis of said characteristic quantity and determine said outline through coupling the points on said outline, wherein said characteristic quantity includes at least one or a plural combination selected from among the scalar quantity of the maximal point, a function taking the scalar quantity as its variable, an average value of the image data associated with a predetermined domain including a point corresponding to the maximal point, a function taking the average value as its variable, a sign of a scalar product of a vector along the assigned line and a gradient of the maximal point on the assigned line, a numerical value representative of the sign, an angle formed by gradients on first and second said maximal points located respectively on mutually different first and second said assigned lines, a function taking the angle as its variable, a distance between an intersection of a straight line passing through the maximal point located on the first assigned line among mutually different first and second said assigned lines and extending in a direction perpendicular to the direction of the gradient of the maximal point and the second assigned line and the maximal point located on the second assigned line, and a function taking the distance as its variable.

6. A system according to claim 1, wherein said gradient arithmetic means is arranged to perform a differentiation in two directions mutually different inside the tomographic surface.

7. A system according to claim 1, wherein said gradient arithmetic means is arranged to perform a two-dimensional differentiating operation using a differentiating filter having a width between 0.5 times and twice as long as a width of one which is narrower in width with respect to a differentiating direction than that of another of two tissues contacting with said outline to be extracted, said two tissues appearing on the tomographic surface.

8. A system according to claim 1, wherein said scalar quantity arithmetic means is arranged to evaluate, as said scalar quantity, at least one selected from among an absolute value of the gradient, a function taking the absolute value as its variable, a sum of absolute values of the gradient as to components with respect to mutually different two directions on the tomographic surface, a function taking said sum as its variable.

9. A system according to claim 1, wherein said outline extracting means has characteristic quantity arithmetic means for evaluating characteristic quantity representative of a probability such that said maximal points are points on said outline, and said outline extracting means is arranged to extract the points on said outline from among said maximal points on the basis of said characteristic quantity and determine said outline through coupling the points on said outline.

10. A system according to claim 8, wherein said outline extracting means comprises:

candidate point extracting means for determining an outline candidate point having a probability that it exists on the outline, from among the maximal point, on the basis of said characteristic quantity; and contour point extracting means for adopting the outline candidate point as the point on the outline when a distance between the outline candidate point determined by said candidate point extracting means and a point on the outline adjacent to the outline candidate point is within a predetermined distance.

11. A system according to claim 10, wherein said subject is a heart of a human body, and said system serves to determine an outline of a left ventricle as said outline;

said system has valve source detecting means for detecting boundary points between two valves existing the left ventricle and a left atrium and a septum of the left ventricle, appearing on the tomographic surface; and said valve source detecting means adopts it as at least one of criteria that a distance between a first outline candidate point determined by said candidate point extracting means and a point on the outline adjacent to the first outline candidate point is within a predetermined distance, and a distance between the first outline candidate point and a second point adjacent to the first outline candidate point is over a predetermined distance, so that the first outline candidate point is extracted as the boundary point.

12. A system according to claim 9, wherein said outline extracting means comprises:

candidate point extracting means for determining on the basis of the characteristic quantity evaluated on a predetermined frame of a plurality of frames each representative of a same tomographic surface at different time an outline candidate point having a probability that it exists on the outline, from among the maximal point in said predetermined frame; and contour point extracting means for adopting the outline candidate point as the point on the outline in said predetermined frame when a distance between the outline candidate point in said predetermined frame determined by said candidate point extracting means and a point on the outline in a frame different from said predetermined frame of said plurality of frames, which point is associated with said outline candidate point, is within a predetermined distance.

13. A system according to claim 12, wherein said subject is a heart of a human body, and said system serves to determine an outline of a left ventricle as said outline;

said system has valve source detecting means for detecting boundary points between two valves existing the left ventricle and a left atrium and a septum of the left ventricle, appearing on the tomographic surface; and said valve source detecting means adopts it as at least one of criteria that a distance between the outline candidate point in said predetermined frame determined by said candidate point extracting means and a point on the outline in a frame different from said predetermined frame of said plurality of frames, which point is associated with said outline candidate point, is over a predetermined distance, so that the outline candidate point is extracted as the boundary in said predetermined frame.

14. A system according to claim 8, wherein said subject is a heart of a human body, and said system serves to determine an outline of a left ventricle as said outline;

said system has value source detecting means for detecting boundary points between two valves existing the left ventricle and a left atrium and a septum of the left ventricle, appearing on the tomographic surface; and said outline extracting means extracts the point on the outline in a domain excepting an area formed when the boundary points are coupled to each other, on the tomographic surface.

15. A system according to claim 1, further comprising outline display means for displaying at least one of a contour coupling the points on the outline with a straight line or a curve, and a picture plane in which an inside and an outside of the out, line are distinguished from each other by a color, a luminance or a pattern.

16. A system according to claim 1, further comprising area arithmetic means for evaluating an area of an inside of the outline extracted by said outline extracting means, and area display means for displaying the area evaluated by said area arithmetic means.

17. A system according to claim 16, wherein said area display means displays the area with at least one of figures representative of the area and a graph indicative of variation in time of the area.

18. A system according to claim 1, further comprising volume arithmetic means for evaluating volume of an inside of the outline extracted by said outline extracting means, and volume display means for displaying the volume evaluated by said volume arithmetic means.

19. A system according to claim 18, wherein said volume display means displays the volume with at least one of figures representative of the volume and a graph indicative of variation in time of the volume.

20. An ultrasonic diagnostic system wherein ultrasonic waves reflected within a subject are received, whereby image data corresponding to each point inside a tomographic surface spreading within the subject is obtained, comprising:

outline arithmetic means for evaluating an outline of a predetermined tissue within the subject on the basis of the image data;

gradient arithmetic means for evaluating gradients of the image data on a plurality of points inside the tomographic surface; and arithmetic effective domain detecting means for determining an arithmetic effective domain including said predetermined tissue within the tomographic surface on the basis of directions of said gradients, wherein said outline arithmetic means determines the outline of said predetermined tissue inside the arithmetic effective domain.

21. A system according to claim 20, wherein said arithmetic effective domain detecting means detects the arithmetic effective domain on the basis of a distribution of binarized image data within the tomographic surface, said binarized image data being produced in such a manner that the image data associated with each point within the tomographic surface is binarized on the basis of an angle formed with a direction of the assigned line starting from a predetermined central point within the tomographic surface and extending through the point on which the gradient is evaluated within the tomographic surface and a direction of the gradient at the point on which the gradient is evaluated.

22. A system according to claim 20, wherein said outline arithmetic means comprises:

scalar quantity arithmetic means for evaluating scalar quantities each corresponding to an associated one of said gradients on a plurality of points within the tomographic surface;

maximal point arithmetic means for evaluating a plurality of maximal points within the arithmetic effective domain so that said scalar quantity assumes a maximal value; and outline extracting means for determining an outline of said predetermined tissue on the basis of said plurality of maximal points.

23. A system according to claim 22, wherein said outline extracting means has characteristic quantity arithmetic means for evaluating characteristic quantity representative of a probability such that said maximal points are points on said outline, and said outline extracting means is arranged to extract the points on said outline from among said maximal points on the basis of said characteristic quantity and determine said outline through coupling the points on said outline.

24. A system according to claim 22, wherein said outline extracting means has characteristic quantity arithmetic means for evaluating characteristic quantity representative of a probability such that said maximal points are points on said outline, and said outline extracting means is arranged to extract the points on said outline from among said maximal points on the basis of said characteristic quantity and determine said outline through coupling the points on said outline, wherein said characteristic quantity includes at least one or a plural combination selected from among the scalar quantity of the maximal point, a function taking the scalar quantity as its variable, an average value of the image data associated with a predetermined domain including a point corresponding to the maximal point, a sign of a scalar product of a vector along the assigned line and a gradient of the maximal point on the assigned line, a numerical value representative of the sign, an angle formed by gradients on first and second said maximal points located respectively on mutually different first and second said assigned lines, a function taking the angle as its variable, a distance between an intersection of a straight line passing through the maximal point located on the first assigned line among mutually different first and second said assigned lines and extending in a direction perpendicular to the direction of the gradient of the maximal point and the second assigned line and the maximal point located on the second assigned line, and a function taking the distance as its variable.

25. A system according to claim 20, further comprising display means for displaying the outline.

26. A system according to claim 20, further comprising induced quantity calculating means for evaluating induced quantity to be calculated on the basis of the outline determined by said outline arithmetic means.

27. A system according to claim 26, wherein said induced quantity calculating means is arranged to evaluate, as said induced quantity, at least one selected from among an area of an inside of the outline, a position of the center of gravity of the outline and a volume of the inside of the outline.

28. A system according to claim 26, further comprising display means for displaying at least one of the induced quantity and variable quantity over a plurality of frames of the induced quantity.

29. An ultrasonic diagnostic system wherein ultrasonic waves reflected within a subject are received, whereby image data corresponding to each point inside a tomographic surface spreading within the subject is obtained, comprising:

movement calculating means for calculating movements on a plurality of points within the tomographic surface on the basis of the image data as to a plurality of frames;

outline arithmetic means for evaluating an outline of a predetermined tissue within the subject on the basis of the image data; and outline modifying means for providing an outline modified from the outline evaluated by said outline arithmetic means on the basis of the movements detected by said movement calculating means.

30. A system according to claim 29, wherein said movement calculating means is arranged to calculate, as said movement, any of a vector of a two-dimensional movement within the tomographic surface and a magnitude of movement with respect to a predetermined direction within the tomographic surface, using any of an optical flow method and a cross correlation method.

31. A system according to claim 30, wherein said predetermined direction is involved in directions of a plurality of assigned lines extending radially inside the tomographic surface taking a predetermined central point of inside of the outline as a starting point.

32. A system according to claim 29, wherein said movement calculating means calculates the movements on the plurality of points as to each of a plurality of domains set up within the tomographic surface, extracts the movement thus calculated, which is deemed to have a high probability that an exact movement is represented, as to each of said plurality of domains, and determines a representative of the movement thus extracted as to each of said plurality of domains.

33. A system according to claim 29, further comprising preprocessing means for practicing one of a smoothing treatment and a binarizing treatment for the image data, wherein said movement calculating means calculates the movements on the basis of the image data subjected to the one of the treatments by said preprocessing means.

34. A system according to claim 29, wherein said outline arithmetic means comprises:

gradient arithmetic means for evaluating gradients of the image data on a plurality of points within the tomographic surface;

scalar quantity arithmetic means for evaluating scalar quantities each corresponding to an associated one of said gradients on the plurality of points within the tomographic surface;

maximal point arithmetic means for evaluating a plurality of maximal points within the tomographic surface so that said scalar quantities assume each a maximal value; and outline extracting means for determining an outline of a predetermined tissue within the subject on the basis of said plurality of maximal points.

35. A system according to claim 29, further comprising a contour point designation handler for designating a contour point located on the outline of said predetermined tissue, wherein said outline arithmetic means evaluates the outline on the basis of the contour point designated by said contour point designation handler.

36. A system according to claim 29, further comprising synchronizing signal generating means for generating a beat synchronizing signal synchronized with a beat of the heart of the subject, wherein said outline arithmetic means evaluates the outline on the basis of the beat synchronizing signal.

37. A system according to claim 29, further comprising memory means for storing the image data of a plurality of frames on an overwrite-feasible basis, and freeze means for inhibiting an overwrite to said memory means, wherein said outline arithmetic means evaluates the outline as to at least one sheet of predetermined frame among a plurality of frames stored in said memory means in a freeze state that the overwrite is inhibited by said freeze means, said movement detecting means calculates the movement as to the other frames except the predetermined frame among the plurality of frames stored in said memory means in the freeze state, and said outline modifying means evaluates an outline modified from the outline which is determined by said outline arithmetic means.

38. A system according to claim 29, further comprising display means for displaying the outline.

39. A system according to claim 29, further comprising induced quantity calculating means for evaluating induced quantity to be calculated on the basis of at least one of the outline determined by said outline arithmetic means and the outline modified by said outline modifying means.

40. A system according to claim 39, wherein said induced quantity calculating means is arranged to evaluate, as said induced quantity, at least one selected from among an area of an inside of the outline, a position of the center of gravity of the outline and a volume of the inside of the outline.

41. A system according to claim 39, further comprising display means for displaying at least one of the induced quantity and variable quantity over a plurality of frames of the induced quantity.

* * * * *

UNITED STATES PATENT AND TRADEMARK OFFICE
CERTIFICATE OF CORRECTION

PATENT NO. : 5,469,850
DATED : November 28, 1995
INVENTOR(S) : Miyuki IIZUKA et al.

It is certified that error appears in the above-indentified patent and that said Letters Patent is hereby corrected as shown below:

Column 1, line 5, delete "1."; and line 12, delete "2.".

Column 13, line 11, underline "Optical flow method".

Column 14, line 32, underline "Cross correlation method".

Column 17, line 40, change "r" to $-\underline{r}-$.

Column 20, line 39, change "d" to $-\underline{d}-$.

Column 21, lines 22, 27, and 31, change "d" to $-\underline{d}-$.

Column 22, line 58, change "d" to $-\underline{d}-$.

Column 23, line 30, change "$\geq 0$" to $-\leq 0-$....

Column 25, line 58, change "r" to $-\underline{r}-$.

Column 26, lines 7 and 8, change "r" to $-\underline{r}-$.

Column 29, line 7, change "a" and "b" to $-\underline{a}-$ and $-\underline{b}-$.

UNITED STATES PATENT AND TRADEMARK OFFICE
CERTIFICATE OF CORRECTION

PATENT NO. : 5,469,850
DATED : November 28, 1995
INVENTOR(S) : Miyuki Iizuka, et. al.

It is certified that error appears in the above-indentified patent and that said Letters Patent is hereby corrected as shown below:

Column 39, line 42, change "out, line" to --outline--.

Signed and Sealed this

Twelfth Day of March, 1996

BRUCE LEHMAN

*Attest:*

*Attesting Officer*    *Commissioner of Patents and Trademarks*